(12) United States Patent
Cook et al.

(10) Patent No.: US 9,745,297 B2
(45) Date of Patent: Aug. 29, 2017

(54) COMPOUNDS AS MODULATORS OF RORC

(71) Applicant: Boehringer Ingelheim International GmbH, Ingelheim am Rhein (DE)

(72) Inventors: Brian Nicholas Cook, Danbury, CT (US); John D. Huber, Trumbull, CT (US); Robert Owen Hughes, Newtown, CT (US); Xiang Li, New Milford, CT (US); Shuang Liang, Roseville, MN (US); Ingo Andreas Mugge, New Haven, CT (US); Michael Robert Turner, Danbury, CT (US); Qiang Zhang, Ridgefield, CT (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 14/907,831

(22) PCT Filed: Jul. 28, 2014

(86) PCT No.: PCT/US2014/048444
§ 371 (c)(1),
(2) Date: Jan. 27, 2016

(87) PCT Pub. No.: WO2015/017335
PCT Pub. Date: Feb. 5, 2015

(65) Prior Publication Data
US 2016/0159791 A1   Jun. 9, 2016

Related U.S. Application Data

(60) Provisional application No. 61/871,480, filed on Aug. 29, 2013, provisional application No. 61/859,983, filed on Jul. 30, 2013.

(51) Int. Cl.
*C07D 471/04* (2006.01)
*C07D 519/00* (2006.01)

(52) U.S. Cl.
CPC ......... *C07D 471/04* (2013.01); *C07D 519/00* (2013.01)

(58) Field of Classification Search
CPC .............................. C07D 471/04; C07D 519/00
USPC ....................................................... 546/113
See application file for complete search history.

(56) References Cited

U.S. PATENT DOCUMENTS

| | | | |
|---|---|---|---|
| 2006/0100230 A1* | 5/2006 | Bischoff | C07D 209/08 514/300 |
| 2007/0135408 A1 | 6/2007 | Cassayre et al. | |
| 2012/0165322 A1 | 6/2012 | Cook et al. | |
| 2016/0251310 A1* | 9/2016 | Cook | C07D 401/02 |

FOREIGN PATENT DOCUMENTS

| | | | |
|---|---|---|---|
| WO | 2005063734 A2 | 7/2005 | |
| WO | 2007026920 A2 | 3/2007 | |
| WO | 2012006203 A1 | 1/2012 | |
| WO | WO2012106995 | * | 8/2012 |
| WO | 2014086894 A1 | 6/2014 | |
| WO | WO2014179564 | * | 11/2014 |
| WO | WO2015116904 | * | 8/2015 |

OTHER PUBLICATIONS

Solt; ACS Chem. Biol., 2012, 7, 1515-1519.*
Khan; Bioorganic & Medicinal Chemistry Letters 2013, 23, 532-536.*
Miossec; Nature Drug Discovery 2012, 11, 763-776.*
Huang; Expert Opin Ther Targets 2007, 11, 737-743.*
Huh; Eur. J. Immunol 2012, 42, 2232-2237.*
Chang; J. Exp. Pharmacol. 2012, 4, 141-148.*
Zhang; Molecular Pharmacology 2012, 82, 583-590.*
Vitae Pharmaceuticals. (Jun. 4, 2013). Progress Update of Vitae's RORgammat inhibitor Program [Press release]. Retrieved from http://ir.vitaepharma.com/phoenix.zhtml?c=219654&p=irol-newsArticle&ID=1963476 (accessed Oct. 5, 2016).*
Japan Tobacco Inc. Clinical Development as of Jul. 30, 2013. http://www.jt.com/investors/results/S_information/pharmaceuticals/pdf/P.L.20130730_E.pdf (accessed Oct. 5, 2016).*
Patani; Chem. Rev. 1996, 96, 3147-3176.*
Huh; ACS Med Chem Lett 2013, 4, 79-84.*
Williams; Nature Medicine 2013, 19, 1078.*
Biswas, Journal of Clinical Investigation, vol. 120, No. 9, 2010, Phosphorylation of IRF4 by ROCK2 regulates IL-17 and IL-21 production and the development of autoimmunity in mice:, p. 3280-3295.
Khan, Bioorganic and Medicinal Chemistry Letters, vol. 23, No. 2, 2013, "Small molecule amides as potent ROR-(gamma) selective modulators", p. 532-536.
International Search Report for PCT/US2014/048444, Form PCT/ISA 210, mailed Oct. 21, 2014.

* cited by examiner

*Primary Examiner* — Noble Jarrell
*Assistant Examiner* — Daniel Carcanague
(74) *Attorney, Agent, or Firm* — Paula K. Wittmayer; Usha R. Patel

(57) ABSTRACT

The present invention encompasses compounds of the formula (I), wherein the variables are defined herein which are suitable for the modulation of RORC and the treatment of diseases related to the modulation of RORC. The present invention also encompasses processes of making compounds of formula (I) and pharmaceutical preparations containing them.

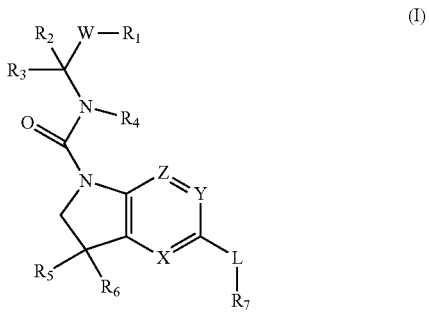

13 Claims, No Drawings

COMPOUNDS AS MODULATORS OF RORC

BACKGROUND OF THE INVENTION

1. Technical Field

The present invention relates to novel compounds which modulate the activity of RORC and their use as medicaments.

2. Background Information

RORγt (retinoid-related orphan receptor γt) (also referred to herein as "RORC") is a transcription factor belonging to the steroid hormone receptor superfamily (reviewed in Jetten 2006. Adv. Dev Biol. 16:313-355.). RORγt has been identified as a transcriptional factor that is required for the differentiation of T cells and secretion of Interluekin 17 (IL-17) from a subset of T cells termed $Th_{17}$ cells (Ivanov, Cell 2006, 126, 1121-1133). The rationale for the use of a RORγt targeted therapy for the treatment of chronic inflammatory diseases is based on the emerging evidence that $Th_{17}$ cells and the cytokine IL-17 contribute to the initiation and progression of the pathogenesis of several autoimmune diseases including psoriasis, ankylosing spondylitis, rheumatoid arthritis, multiple sclerosis and Crohn's disease (reviewed in Miossec, Nature Drug Discovery 2012, 11, 763-776; see also Khan et al., Bioorganic & Medicinal Chemistry Letters 23 (2013), 532-536). The outcome of recent clinical trials with nuetralizing antobodies to IL-17 and its receptor IL-17RA (Leonardi 2012, New England Journal of Medicine, 366, 1190-1199; Papp 2012, New England Journal of Medicine 366, 1181-1189) in psoriasis highlight the role of IL-17 in the pathogenesis of this disease. As such, attenuation of IL-17 secretion from activated Th17 T cells via inhibtion of RORγt may offer similar therapeutic benefit.

SUMMARY OF THE INVENTION

The invention comprises a novel class of heteroaromatic compounds and methods for making and using the same. These compounds are useful for the treatment of autoimmune and allergic disorders in that they exhibit good modulatory effect upon RORC.

DETAILED DESCRIPTION OF THE INVENTION

In the first embodiment of the invention there is provided a compound of formula (I)

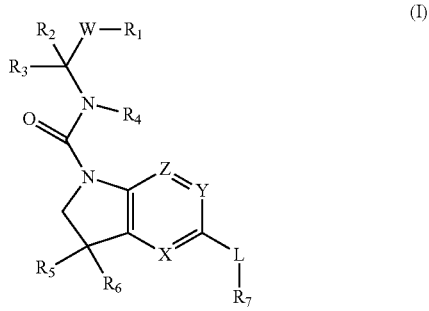

(I)

$R_1$ is: —CN, —S(O)$_m$C$_{1-6}$alkyl, —S(O)$_m$C$_{1-6}$cyanoalkyl —S(O)$_m$C$_{1-6}$haloalkyl, —S(O)$_m$C$_{3-6}$cycloalkyl, —S(O)$_m$C$_{1-6}$ hydroxyalkyl, —S(O)$_m$C$_{1-6}$alkyloxy, —SO$_2$NR$_a$R$_b$, —NR$_a$S(O)$_m$C$_{1-6}$alkyl, —NR$_a$S(O)$_m$C$_{3-6}$cycloalkyl, —S(O)(NRc) C$_{1-6}$alkyl —S(O)(NRc) C$_{3-6}$cycloalkyl or —S(O)(NRc) NR$_a$R$_b$ wherein R$_a$ and R$_b$ are each independently H, NR$_a$R$_b$ C$_{1-6}$alkyl, C$_{3-6}$cycloalkyl, C$_{1-6}$haloalkyl, C$_{1-6}$cyanoalkyl, or C$_{1-6}$alkyloxy or; R$_a$ and R$_b$ taken together with the nitrogen to which they are attached form a C$_{2-6}$ heterocyclic ring optionally containing 1-4 additional groups selected from NH, O and S; and m is 0, 1 or 2; and R$_c$ is each independently H, C$_{1-6}$alkyl, C$_{3-6}$cycloalkyl, or C$_{1-6}$alkyloxy; W is: C$_{6-14}$ aryl, a C$_{2-10}$ heteroaryl containing 1-4 groups selected from N, NH, O and S, saturated and partially saturated C$_{2-10}$ heterocyclyl containing 1-4 groups selected from N, NH, O and S, or saturated and partially saturated C$_{3-12}$ cycloalkyl ring, wherein each W is optionally substituted with 0-4 substituents selected from the group consisting of cyano, halo, hydroxy, C$_{1-6}$alkyl, C$_{1-6}$ haloalkyl, C$_{1-6}$ hydroxyalkyl, C$_{1-6}$ alkenyl, C$_{1-6}$ haloalkenyl, C$_{1-6}$ alkynyl, C$_{1-6}$ haloalkynyl, C$_{3-6}$ cycloalkyl, C$_{3-6}$ heterocycle containing 1-4 groups selected from NH, O and S, C$_{1-6}$ alkoxy, C$_{3-6}$ cycloalkyl-oxy, —S(O)$_m$C$_{1-6}$ alkyl, —S(O)$_m$C$_{3-6}$ cycloalkyl, CN, —C(O)—NR$_c$R$_d$, —C(O)—OR$_c$, —NR$_c$R$_d$, NR$_c$R$_d$—C$_{1-6}$alkyl-, and R$_c$O—C$_{1-6}$alkoxy NR$_c$R$_d$—C$_{1-6}$alkoxy-, wherein R$_c$ and R$_d$ is each independently H, C$_{1-6}$ alkyl, C$_{1-6}$ alkenyl, C$_{1-6}$ alkynyl, C$_{3-12}$ cycloalkyl, C$_{6-14}$ aryl, C$_{2-6}$ heterocycle containing 1-4 groups selected from NH, O and S, or a C$_{2-10}$heteroaryl containing 1-4 groups selected from N, NH, O and S, or Rc and R$_d$ taken together with the nitrogen to which they are attached form a C$_{2-6}$ heterocyclic ring optionally containing 1-4 additional groups selected from NH, O and S;

$R_2$ is: —C$_{1-6}$alkyl, —C$_{3-6}$cylcoalkyl, —C$_{1-6}$alkyloxy, —C$_{1-6}$ hydroxyalkyl, —C$_{1-6}$haloalkyl, —H, —C(O)OR$_e$, or —C(O)NR$_e$R$_f$, wherein R$_e$ and R$_f$ is each independently H or C$_{1-6}$ alkyl;

$R_3$ is: —C$_{1-6}$alkyl, —C$_{3-6}$cylcoalkyl, —C$_{1-6}$alkyloxy; —H, —C(O)OR$_e$, or C(O)NR$_e$R$_f$, wherein R$_e$ and R$_f$ is each independently H or C$_{1-6}$ alkyl; or $R_2$ and $R_3$ taken together with the carbon to which they are attached form a C$_{3-12}$ carbocyclic ring or a C$_{2-10}$ heterocyclic containing 1-4 groups selected from NH, O and S; $R_4$ is: —H, —C$_{1-6}$alkyl, —C$_{1-6}$alkyloxy, or —C$_{3-6}$cylcoalkyl;

X, Y and Z are chosen independently from N and CR, wherein one and only one of X, Y and Z is N and R$_e$ is: —H, -halo, —C$_{1-6}$alkyl, —C$_{1-6}$ haloalkyl, —C$_{1-6}$ haloalkenyl, —C$_{1-6}$ haloalkynyl, —C$_{3-6}$ cycloalkyl, —C$_{1-6}$ alkoxy, —C$_{3-6}$ cycloalkyloxy, —OC$_{1-6}$alkyl, —OC$_{3-6}$ cycloalkyl, —S(O)$_m$C$_{1-6}$ alkyl, —S(O)$_m$C$_{3-6}$ cycloalkyl, CN, —C(O)—NR$_f$R$_g$, —C(O)—OR$_f$, or —NR$_f$R$_g$, wherein R$_f$ and R$_g$ is each independently H or —C$_{1-6}$ alkyl; C$_{1-6}$ alkenyl, C$_{1-6}$ alkynyl, C$_{3-12}$ cycloalkyl, C$_{6-14}$ aryl, C$_{3-6}$ heterocycle containing 1-4 groups selected from N, NH, O and S, or a C$_{2-10}$ heteroaryl containing 1-4 groups selected from N, NH, O and S; $R_5$ is: —H -halo, —C$_{1-6}$ alkyl, C$_{1-6}$ alkenyl, —C$_{1-6}$ alkoxy, —S(O)$_m$C$_{1-6}$alkyl, —C$_{6-14}$ aryl, —C$_{2-10}$ heterocyclyl containing 1-4 groups selected from N, NH, O and S, —C$_{2-10}$ heteroaryl containing 1-4 groups selected from N, NH, O and S, —CN, —C$_3$-C$_6$cycloalkyl, or —C$_{1-6}$haloalkyl, wherein $R_5$ may be optionally substituted with 0-5 halo, C$_{1-6}$ alkyl, C$_{1-6}$ alkoxy, —S(O)$_m$C$_{1-6}$alkyl, C$_{6-14}$ aryl, C$_{2-10}$ heterocyclyl containing 1-4 groups selected from N, NH, O and S, or a C$_{2-10}$ heteroaryl containing 1-4 groups selected from N, NH, O and S, CN, C$_3$-C$_6$cycloalkyl, OH or —C(O)—NR$_a$R$_b$, R$_6$ is: -halo, —C$_{1-6}$ alkyl, C$_{1-6}$ alkenyl, —C$_{1-6}$ alkoxy, —S(O)$_m$C$_{1-6}$alkyl, —C$_{6-14}$ aryl, —C$_{2-10}$ heterocyclyl containing 1-4 groups selected from N, NH, O and S, —C$_{2-10}$ heteroaryl containing 1-4 groups selected from N, NH, O and S, —H, —CN, —C$_3$-C$_6$cycloalkyl, or —C$_{1-6}$haloalkyl, wherein $R_6$ may be optionally substituted with 0-5 halo, $C_{1-6}$ alkyl, $C_{1-6}$ alkoxy, —S(O)$_m$C$_{1-6}$alkyl, $C_{6-14}$ aryl, $C_{2-10}$ heterocyclyl containing 1-4 groups selected from N, NH, O and S, or a $C_{2-10}$ heteroaryl containing 1-4 groups selected from N, NH, O and S, CN, $C_3$-$C_6$cycloalkyl, OH or —C(O)—NR$_a$R$_b$, or R$_5$ and R$_6$ taken together with the carbon to which they attached form a $C_{3-12}$ carbocyclic ring or a $C_{2-10}$ heterocyclic containing 1-4 groups selected from N, NH, O and S; L is: a direct bond, —C=C—

—S(O)$_m$—, —S(O)$_m$NR$_a$—, —C(O)—, —(CH$_2$)$_n$—, —O—(CH$_2$)$_n$—, —N(R$_a$)—, —N(R$_a$)—(CH$_2$)$_n$—, —(CH$_2$)$_n$—N(R$_a$)—, —C(O)—N(R$_a$)—, —C(O)—N(R$_a$)—(CH$_2$)$_n$— or —N(R$_a$)—C(O)—N(R$_b$)—; wherein R$_a$ and R$_b$ is each independently H or C$_{1-3}$ alkyl; R$_7$ is: halo, cycloalkyl, cycloalkenyl,

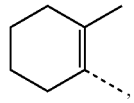

—C$_{6-14}$ aryl, —C$_{2-10}$ heterocyclyl containing 1-4 groups selected from N, NH, O and S, —C$_{2-10}$ heteroaryl containing 1-4 groups selected from N, NH, O and S, wherein R$_7$ may be optionally substituted with 0-5 substituents selected from the group consisting of halogen, hydroxy, C$_{1-6}$alkyl, C$_{1-6}$ haloalkyl, C$_{1-6}$ hydroxyalkyl, C$_{1-6}$ haloalkenyl, C$_{1-6}$ haloalkynyl, C$_{3-6}$ cycloalkyl, C$_{3-7}$ heterocycle containing 1-4 groups selected from N, NH, O and S, C$_{6-14}$ aryl, C$_{2-10}$ heteroaryl containing 1-4 groups selected from N, NH, O and S, C$_{1-6}$ alkoxy, C$_{1-6}$ haloalkoxy, C$_{3-6}$ cycloalkyloxy, —S(O)$_m$C$_{1-6}$ alkyl, —S(O)$_m$C$_{3-6}$ cycloalkyl, CN, —C(O)—NR$_c$R$_d$, —C(O)—OR$_c$, NR$_c$R$_d$ and NR$_c$R$_d$C$_{1-6}$alkyl-, wherein R$_c$ and R$_d$ is each independently H, C$_{1-6}$ alkyl, C$_{1-6}$ alkenyl, C$_{1-6}$ alkynyl, cycloalkyl, —C$_{6-14}$ aryl, C$_{2-10}$ heterocyclyl containing 1-4 groups selected from N, NH, O and S, or a C$_{2-10}$ heteroaryl containing 1-4 groups selected from N, NH, O and S, wherein each heterocyclyl, aryl or heteroaryl is optionally substituted by C$_{1-6}$ alkyl, C$_{1-6}$ alkoxy; or Rc and Rd-together with the nitrogen to which they are attached form a C$_{2-6}$ heterocyclic ring optionally containing 1-4 additional groups selected from N, NH, O and S, wherein the heterocyclic ring is optionally substituted by C$_{1-6}$ alkyl, hydroxy or C$_{1-6}$ alkoxy; each n is independently 1-4; each m is independently 0-2; or a pharmaceutically acceptable salt thereof.

Additional subgeneric embodiments for R$_1$, R$_2$, R$_3$, R$_4$, R$_5$, R$_6$, R$_7$, W, X, Y, Z and L in formula (I) set forth above are as described below:

The compound according to the first embodiment described above and wherein: R$_1$ is: —S(O)$_m$C$_{1-6}$alkyl, —S(O)$_m$C$_{1-6}$haloalkyl, —S(O)$_m$C$_{3-6}$cycloalkyl, —SO$_2$NR$_a$R$_b$ wherein R$_a$ and R$_b$ are each independently H, C$_{1-6}$alkyl, C$_{3-6}$cycloalkyl, or C$_{1-6}$alkyloxy, or R$_a$ and R$_b$ taken together with the nitrogen to which they are attached form a —C$_{2-6}$ heterocyclic ring optionally containing 1-4 additional groups selected from NH, O and S; —S(O)(NRc) C$_{1-6}$alkyl, —S(O)(NRc) C$_{3-6}$cycloalkyl, wherein R$_c$ is each independently H, C$_{1-6}$alkyl, C$_{3-6}$cycloalkyl, or C$_{1-6}$alkyloxy or —CN; and each m is independently 0-2; or a pharmaceutically acceptable salt thereof.

The compound according to the first embodiment described above and wherein: R$_1$ is: —S(O)$_2$C$_{1-6}$alkyl, or —SO$_2$NR$_a$R$_b$ wherein R$_a$ and R$_b$ are independently H and C$_{1-6}$alkyl; or a pharmaceutically acceptable salt thereof.

The compound according to the first embodiment described above and wherein: R$_1$ is: —S(O)$_2$C$_{1-3}$alkyl or —SO$_2$NR$_a$R$_b$ wherein R$_a$ and R$_b$ are independently chosen from H and C$_{1-3}$alkyl; or a pharmaceutically acceptable salt thereof.

The compound according to the first embodiment described above and wherein: W is: C$_{6-14}$ aryl, C$_{2-10}$ heteroaryl containing 1-4 groups selected from N, NH, O and S, or bicyclo[1.1.1] pentane wherein each W is optionally substituted with 0-4 substituents selected from the group consisting of halo, hydroxy, C$_{1-6}$alkyl, C$_{1-6}$ haloalkyl, C$_{1-6}$ haloalkenyl, C$_{1-6}$ haloalkynyl, C$_{3-6}$ cycloalkyl, C$_{1-6}$ alkoxy, C$_{3-6}$ cycloalkyloxy, —S(O)$_m$C$_{1-6}$ alkyl, —S(O)$_m$C$_{3-6}$ cycloalkyl, CN, —C(O)—NR$_c$R$_d$, —C(O)—OR$_c$, and NR$_c$R$_d$ wherein R$_c$ and R$_d$ is each independently H, C$_{1-6}$ alkyl, C$_{1-6}$ alkenyl, C$_{1-6}$ alkynyl, cycloalkyl, —C$_{6-14}$ aryl, C$_{2-10}$ heterocycyl containing 1-4 groups selected from NH, O and S, or a C$_{2-10}$ heteroaryl containing 1-4 groups selected from N, NH, O and S; or a pharmaceutically acceptable salt thereof.

The compound according to the first embodiment described above and wherein: W is: phenyl, or monocyclic C$_{3-5}$ heteroaryl containing 1-2 nitrogens as the only heteroatoms in the ring, wherein each W is optionally substituted with 0-4 substituents selected from the group consisting of halo, C$_{1-6}$alkyl, C$_{1-6}$ haloalkyl, C$_{1-6}$ haloalkenyl, C$_{1-6}$ haloalkynyl, C$_{3-6}$ cycloalkyl, C$_{1-6}$ alkoxy, C$_{3-6}$ cycloalkyloxy, —S(O)$_m$C$_{1-6}$ alkyl, —S(O)$_m$C$_{3-6}$ cycloalkyl, —CN, —C(O)—NR$_c$R$_d$, —C(O)—OR$_c$, and NR$_c$R$_d$, wherein R$_c$ and R$_d$ is each independently H, C$_{1-6}$ alkyl, C$_{1-6}$ alkenyl, C$_{1-6}$ alkynyl, or cycloalkyl; or a pharmaceutically acceptable salt thereof.

The compound according to the first embodiment described above and wherein: W is: phenyl, or C$_{4-5}$ monocyclic heteroaryl containing 1-2 nitrogens as the only heteroatoms in the ring, wherein each W is optionally substituted with 0-4 substituents selected from the group consisting of halo, C$_{1-6}$alkyl, C$_{1-6}$ haloalkyl, C$_{1-6}$ haloalkenyl, C$_{1-6}$ haloalkynyl, C$_{3-6}$ cycloalkyl, C$_{1-6}$ alkoxy, C$_{3-6}$ cycloalkyloxy, —S(O)$_m$C$_{1-6}$ alkyl, —S(O)$_m$C$_{3-6}$ cycloalkyl, —CN, —C(O)—NR$_c$R$_d$, —C(O)—OR$_c$, and NR$_c$R$_d$, wherein R$_c$ and R$_d$ is H, C$_{1-6}$ alkyl, C$_{1-6}$ alkenyl, C$_{1-6}$ alkynyl, or cycloalkyl; or a pharmaceutically acceptable salt thereof.

The compound according to the first embodiment described above and wherein: R$_2$ is: H, or C$_{1-6}$alkyl; and R$_3$ is: H, or C$_{1-6}$alkyl; or R2 and R3 taken together form a cyclopropane-ring or a pharmaceutically acceptable salt thereof.

The compound according to the first embodiment described above and wherein: R$_2$ and R$_3$ are H; or a pharmaceutically acceptable salt thereof.

The compound according to the first embodiment described above and wherein: R$_4$ is: H, or C$_{1-6}$alkyl; or a pharmaceutically acceptable salt thereof.

The compound according to the first embodiment described above and wherein: R$_4$ is H; or a pharmaceutically acceptable salt thereof.

The compound according to the first embodiment described above and wherein: X is N, and both Y and Z are chosen independently from CR$_e$ and R$_e$ is as defined in claim 1; or a pharmaceutically acceptable salt thereof.

The compound according to the first embodiment wherein: Z is N, and both X and Y are chosen independently from $CR_e$; and $R_e$ is:
—H, or —$C_{1-6}$alkyl; or a pharmaceutically acceptable salt thereof.

The compound according to the first embodiment described above and wherein: Y is N and both X and Z are chosen independently from CR, and $R_e$ is as defined in claim 1; or a pharmaceutically acceptable salt thereof.

The compound according to the first embodiment described above and wherein: X is N, and both Y and Z are chosen independently from $CR_e$; and $R_e$ is: H, halo, $C_{1-6}$alkyl, $OC_{1-6}$alkyl, or cycloalkyl; or a pharmaceutically acceptable salt thereof.

The compound according to the first embodiment described above and wherein: Y is N and both X and Z are chosen independently from $CR_e$; and $R_e$ is: H, halo, $C_{1-6}$alkyl, O $C_{1-6}$alkyl, or cycloalkyl; or a pharmaceutically acceptable salt thereof.

The compound according to the first embodiment described above and wherein: X is N, and both Y and Z are chosen independently from $CR_e$; and $R_e$ is: —H, or —$C_{1-6}$ alkyl; or a pharmaceutically acceptable salt thereof.

The compound according to the first embodiment described above and wherein: Y is N, and both X and Z are chosen independently from $CR_e$; and $R_e$ is: —H, or —$C_{1-6}$ alkyl; or a pharmaceutically acceptable salt thereof.

The compound according to the first embodiment described above and wherein: $R_5$ is: H; $C_{1-6}$ alkyl, or $C_3$-$C_6$cycloalkyl; wherein $R_5$ may be optionally substituted with 0-5 halo, $C_{1-6}$ alkyl, $C_{1-6}$ alkoxy, —$S(O)_mC_{1-6}$alkyl, —$S(O)_mC_{1-6}$alkyl, —$C_{6-14}$ aryl, $C_{2-10}$ heterocycyl containing 1-4 groups selected from NH, O and S, $C_{2-10}$ heteroaryl containing 1-4 groups selected from N, NH, O and S; CN, or $C_3$-$C_6$cycloalkyl; $R_6$ is: H; $C_{1-6}$ alkyl, or $C_3$-$C_6$cycloalkyl;
wherein $R_6$ may be optionally substituted optionally substituted with 0-5 substituents selected from the group consisting of halogen, $C_{1-6}$ haloalkyl, $C_{1-6}$ haloalkenyl, $C_{1-6}$ haloalkynyl, $C_{3-6}$ cycloalkyl, $C_{1-6}$ alkoxy, $C_{3-6}$ cycloalkyloxy, —$S(O)_mC_{1-6}$ alkyl, —$S(O)_mC_{3-6}$ cycloalkyl, —CN, —C(O)—$NR_cR_d$, —C(O)—$OR_c$, and $NR_cR_d$ wherein $R_c$ and $R_d$ is H, $C_{1-6}$ alkyl, $C_{1-6}$ alkenyl, $C_{1-6}$ alkynyl, cycloalkyl, —$C_{6-14}$ aryl, $C_{2-10}$ heterocycyl containing 1-4 groups selected from NH, O and S, $C_{2-10}$ heteroaryl containing 1-4 groups selected from N, NH, O and S; or $R_5$ and $R_6$ taken together with the carbon to which they attached form a $C_{3-12}$ carbocyclic ring or a $C_{2-10}$ heterocyclic ring containing 1-4 groups selected from NH, O and S; or a pharmaceutically acceptable salt thereof.

The compound according to the first embodiment described above and wherein: $R_5$ is: H; or $C_{1-3}$ alkyl; $R_6$ is: H; or $C_{1-3}$ alkyl; or $R_5$ and $R_6$ taken together with the carbon to which they attached may form a $C_{5-6}$ carbocyclic ring; or a pharmaceutically acceptable salt thereof.

The compound according to the first embodiment described above and wherein: $R_5$ and $R_6$ are each independently —$C_{1-3}$ alkyl; or $R_5$ and $R_6$ taken together with the carbon to which they attached may form a $C_{3-6}$ carbocyclic ring or a $C_{2-5}$ heterocyclic ring containing 1-4 groups selected from NH, O and S; or a pharmaceutically acceptable salt thereof.

The compound according to the first embodiment described above and wherein: L is: a bond, —O— or —O—(CH$_2$)$_n$—; or a pharmaceutically acceptable salt thereof.

The compound according to the first embodiment described above and wherein: L is a bond; or a pharmaceutically acceptable salt thereof.

The compound according to the first embodiment described above and wherein: $R_7$ is: halo, $C_{6-14}$ aryl or $C_{2-10}$ heteroaryl containing 1-4 groups selected from N, NH, O and S; wherein $R_7$ may be optionally substituted with 0-5 substituents selected from the group consisting of halogen, hydroxy, $C_{1-6}$ alkyl, $C_{1-6}$ haloalkyl, $C_{1-6}$ hydroxyalkyl, $C_{1-6}$ haloalkenyl, $C_{1-6}$ haloalkynyl, $C_{3-6}$ cycloalkyl, $C_{1-6}$ alkoxy, $C_{1-6}$ haloalkoxy, $C_{3-6}$ cycloalkyloxy, —$S(O)_mC_{1-6}$ alkyl, —$S(O)_mC_{3-6}$ cycloalkyl, —CN, —C(O)—$NR_cR_d$, —C(O)—$OR_c$, and $NR_cR_d$, wherein $R_c$ and $R_d$ is H, $C_{1-6}$ alkyl, $C_{1-6}$ alkenyl, $C_{1-6}$ alkynyl, $C_{3-12}$ cycloalkyl, $C_{6-14}$ aryl, $C_{2-6}$ heterocycyl containing 1-4 groups selected from NH, O and S, or a $C_{2-10}$ heteroaryl containing 1-4 groups selected from N, NH, O and S; each m is independently 0-2; or a pharmaceutically acceptable salt thereof.

The compound according to the first embodiment described above and wherein: $R_7$ is: phenyl, bi-phenyl, naphthyl, $C_{4-5}$ monocyclic heteroaryl, $C_{8-9}$ fused heteroaryl or $C_{10-11}$ bi-heteroaryl wherein said heteroaryls contain 1-2 nitrogens as the only heteroatoms in the ring; wherein $R_7$ may be optionally substituted optionally substituted with 0-5 substituents selected from the group consisting of halogen, hydroxy, $C_{1-6}$alkyl, $C_{1-6}$ haloalkyl, $C_{1-6}$ hydroxyalkyl, $C_{1-6}$ haloalkenyl, $C_{1-6}$ haloalkynyl, $C_{3-6}$ cycloalkyl, $C_{1-6}$ alkoxy, $C_{3-6}$ cycloalkyloxy, —$S(O)_mC_{1-6}$ alkyl, —$S(O)_mC_{3-6}$ cycloalkyl, —CN, —C(O)—$NR_cR_d$, —C(O)—$OR_c$, and $NR_cR_d$ wherein $R_c$ and $R_d$ is each independently H, $C_{1-6}$ alkyl, $C_{1-6}$ alkenyl, $C_{1-6}$ alkynyl or cycloalkyl;
each m is independently 0-2; or a pharmaceutically acceptable salt thereof.

The compound according to the first embodiment described above and wherein: $R_7$ is: phenyl, or a $C_{4-5}$ monocyclic heteroaryl containing 1-2 nitrogens as the only heteroatoms in the ring; wherein $R_7$ may be optionally substituted with 0-5 substituents selected from the group consisting of halogen, hydroxy, $C_{1-6}$alkyl, $C_{1-6}$ haloalkyl, $C_{1-6}$ haloalkenyl, $C_{1-6}$ haloalkynyl, $C_{3-6}$ cycloalkyl, $C_{1-6}$ alkoxy, $C_{3-6}$ cycloalkyloxy, —$S(O)_mC_{1-6}$ alkyl, —$S(O)_m C_{3-6}$ cycloalkyl, —CN, —C(O)—$NR_cR_d$, —C(O)—$OR_c$, and $NR_cR_d$, wherein each $R_c$ and $R_d$ is independently H, $C_{1-6}$ alkyl, $C_{1-6}$ alkenyl, $C_{1-6}$ alkynyl or $C_{3-12}$ cycloalkyl; each m is independently 0-2; or a pharmaceutically acceptable salt thereof.

The compound according to the first embodiment described above and wherein: $R_1$ is: —$S(O)_mC_{1-6}$alkyl, —$S(O)_mC_{3-6}$cycloalkyl, —$SO_2NR_aR_b$, wherein $R_a$ and $R_b$ are each independently H, $C_{1-6}$alkyl, $C_{3-6}$cycloalkyl, or $C_{1-6}$alkyloxy, or $R_a$ and $R_b$ taken together with the nitrogen to which they are attached form a $C_{2-6}$ heterocyclic ring optionally containing 1-4 additional groups selected from NH, O and S; or —CN; W is: $C_{6-14}$ aryl or a $C_{2-10}$ heteroaryl containing 1-4 groups selected from N, NH, O and S, wherein each W is optionally substituted with 0-4 substituents selected from the group consisting of halo, hydroxy, $C_{1-6}$alkyl, $C_{1-6}$ haloalkyl, $C_{1-6}$ haloalkenyl, $C_{1-6}$ haloalkynyl, $C_{3-6}$ cycloalkyl, $C_{1-6}$ alkoxy, $C_{3-6}$ cycloalkyloxy, —$S(O)_m C_{1-6}$ alkyl, —$S(O)_mC_{3-6}$ cycloalkyl, CN, —C(O)—$NR_cR_d$, —C(O)—$OR_c$, and $NR_cR_d$ wherein $R_c$ and $R_d$ is each independently H, $C_{1-6}$ alkyl, $C_{1-6}$ alkenyl, $C_{1-6}$ alkynyl, $C_{3-12}$ cycloalkyl, $C_{6-14}$ aryl, $C_{2-6}$ heterocycyl containing 1-4 groups selected from NH, O and S, or a $C_{2-10}$ heteroaryl containing 1-4 groups selected from N, NH, O and S; $R_2$ is: H, or $C_{1-6}$alkyl; $R_3$ is: H, or $C_{1-6}$alkyl; $R_4$ is: H, or $C_{1-6}$alkyl; X is N, and both Y and Z are chosen independently from $CR_e$; or Y is N and both X and Z are chosen independently from $CR_e$; and $R_e$ is: H, halo, $C_{1-6}$alkyl, $C_{1-6}$ haloalkyl, $C_{1-6}$ haloalkenyl, $C_{1-6}$ haloalkynyl, $C_{3-6}$ cycloalkyl, $C_{1-6}$ alkoxy, $C_{3-6}$ cycloalkyloxy, —$S(O)_mC_{1-6}$ alkyl, —$S(O)_mC_{3-6}$ cycloalkyl, —CN, —C(O)—$NR_fR_g$, —C(O)—$OR_f$, or —$NR_fR_g$, wherein $R_f$ and $R_g$ is H or $C_{1-6}$ alkyl, —$C_{1-6}$ alkenyl, —$C_{1-6}$ alkynyl, or —$C_{3-12}$ cycloalkyl; $R_5$ is: H; $C_{1-}$ alkyl, or $C_3$-$C_6$cycloalkyl; wherein $R_5$ may be optionally substituted with 0-5 halo, $C_{1-6}$ alkyl, $C_{1-6}$ alkoxy, —S(O)$_m$ $C_{1-6}$alkyl, —S(O)$_m$C$_{1-6}$alkyl, —C$_{6-14}$ aryl, C$_{2-10}$ heterocycyl containing 1-4 groups selected from NH, O and S, $C_{2-10}$ heteroaryl containing 1-4 groups selected from N, NH, O and S, CN, or $C_3$-$C_6$cycloalkyl; $R_6$ is: H; $C_{1-6}$ alkyl, or $C_3$-$C_6$cycloalkyl; wherein $R_6$ may be optionally substituted optionally substituted with 0-5 substituents selected from the group consisting of halogen, $C_{1-6}$ haloalkyl, $C_{1-6}$ haloalkenyl, $C_{1-6}$ haloalkynyl, $C_{3-6}$ cycloalkyl, $C_{1-6}$ alkoxy, $C_{3-6}$ cycloalkyloxy, —S(O)$_m$C$_{1-6}$ alkyl, —S(O)$_m$C$_{3-6}$ cycloalkyl, —CN, —C(O)—NR$_c$R$_d$, —C(O)—OR$_c$, and NR$_c$R$_d$ wherein R$_c$ and R$_d$ is H, $C_{1-6}$ alkyl, $C_{1-6}$ alkenyl, $C_{1-6}$ alkynyl, $C_{3-12}$ cycloalkyl, $C_{6-14}$ aryl, $C_{2-6}$ heterocycyl containing 1-4 groups selected from NH, O and S, or a $C_{2-10}$ heteroaryl containing 1-4 groups selected from N, NH, O and S; or $R_5$ and $R_6$ taken together with the carbon to which they attached form a $C_{3-12}$ carbocyclic ring; L is: a bond, —O— or —O—(CH$_2$)$_n$—; $R_7$ is: halo, $C_{6-14}$ aryl or $C_{2-10}$ heteroaryl containing 1-4 groups selected from N, NH, O and S; wherein $R_7$ may be optionally substituted with 0-5 substituents selected from the group consisting of halogen, hydroxy, $C_{1-6}$ alkyl, $C_{1-6}$ haloalkyl, $C_{1-6}$ hydroxyalkyl, $C_{1-6}$ haloalkenyl, $C_{1-6}$ haloalkynyl, $C_{3-6}$ cycloalkyl, $C_{1-6}$ alkoxy, $C_{1-6}$ haloalkoxy, $C_{3-6}$ cycloalkyloxy, —S(O)$_m$C$_{1-6}$ alkyl, —S(O)$_m$C$_{3-6}$ cycloalkyl, —CN, —C(O)—NR$_c$R$_d$, —C(O)—OR$_c$, and NR$_c$R$_d$, wherein R$_c$ and R$_d$ is H, $C_{1-6}$ alkyl, $C_{1-6}$ alkenyl, $C_{1-6}$ alkynyl, $C_{3-12}$ cycloalkyl, $C_{6-14}$ aryl, $C_{2-6}$ heterocycyl containing 1-4 groups selected from NH, O and S, or a $C_{2-10}$ heteroaryl containing 1-4 groups selected from N, NH, O and S;
each m is independently 0-2; or a pharmaceutically acceptable salt thereof.

The compound according to the first embodiment described above and wherein: $R_1$ is: —S(O)$_2$C$_{1-6}$alkyl, or —SO$_2$NR$_a$R$_b$ wherein R$_a$ and R$_b$ are independently H and $C_{1-6}$alkyl; W is: phenyl, or $C_{4-5}$ heteroaryl containing 1-2 nitrogens as the only heteroatoms in the ring, wherein each W is optionally substituted with 0-4 substituents selected from the group consisting of halo, $C_{1-6}$alkyl, $C_{1-6}$ haloalkyl, $C_{1-6}$ haloalkenyl, $C_{1-6}$ haloalkynyl, $C_{3-6}$ cycloalkyl, $C_{1-6}$ alkoxy, $C_{3-6}$ cycloalkyloxy, —S(O)$_m$C$_{1-6}$ alkyl, —S(O)$_m$ $C_{3-6}$ cycloalkyl, —CN, —C(O)—NR$_c$R$_d$, —C(O)—OR$_c$, and NR$_c$R$_d$, wherein R$_c$ and R$_d$ is each independently H, $C_{1-6}$ alkyl, $C_{1-6}$ alkenyl, $C_{1-6}$ alkynyl, or $C_{3-12}$ cycloalkyl; $R_2$ is: —H, or —C$_{1-3}$alkyl; $R_3$ is: —H, or —C$_{1-3}$alkyl; $R_4$ is: —H, or —C$_{1-3}$alkyl; X is N, and both Y and Z are chosen independently from CR$_e$; or Y is N and both X and Z are chosen independently from CR$_e$; and R$_e$ is: H, halo, $C_{1-6}$alkyl, or $C_{3-12}$ cycloalkyl; $R_5$ is: H; or $C_{1-3}$ alkyl; $R_6$ is: H; or $C_{1-3}$ alkyl;
or $R_5$ and $R_6$ taken together with the carbon to which they attached form a $C_{5-6}$ carbocyclic ring; L is: a bond; $R_7$ is: phenyl, or $C_{4-5}$ heteroaryl containing 1-2 nitrogens as the only heteroatoms in the ring; wherein $R_7$ may be optionally substituted optionally substituted with 0-5 substituents selected from the group consisting of halogen, hydroxy, $C_{1-6}$alkyl, $C_{1-6}$ haloalkyl, $C_{1-6}$ hydroxyalkyl, $C_{1-6}$ haloalkenyl, $C_{1-6}$ haloalkynyl, $C_{3-6}$ cycloalkyl, $C_{1-6}$ alkoxy, $C_{3-6}$ cycloalkyloxy, —S(O)$_m$C$_{1-6}$ alkyl, —S(O)$_m$C$_{3-6}$ cycloalkyl, —CN, —C(O)—NR$_c$R$_d$, —C(O)—OR$_c$ and NR$_c$R$_d$ wherein R$_c$ and R$_d$ is each independently H, $C_{1-6}$ alkyl, $C_{1-6}$ alkenyl, $C_{1-6}$ alkynyl or $C_{3-12}$ cycloalkyl; each m is independently 0-2; or a pharmaceutically acceptable salt thereof.

The compound according to the first embodiment described above and wherein: $R_1$ is: —S(O)$_2$C$_{1-3}$alkyl, or —SO$_2$NR$_a$R$_b$ wherein R$_a$ and R$_b$ are independently chosen from H and $C_{1-3}$alkyl; W is: phenyl, or $C_{4-5}$ heteroaryl containing 1-2 nitrogens as the only heteroatoms in the ring, wherein each W is optionally substituted with 0-4 substituents selected from the group consisting of halo, $C_{1-6}$alkyl, haloalkyl, haloalkenyl, haloalkynyl, $C_{3-6}$ cycloalkyl, alkoxy, $C_{3-6}$ cycloalkyloxy, —S(O)$_m$C$_{1-6}$ alkyl, —S(O)$_m$C$_{3-6}$ cycloalkyl, —CN, —C(O)—NR$_c$R$_d$, —C(O)—OR$_c$ and NR$_c$R$_d$, wherein each R$_c$ and R$_d$ is independently H, $C_{1-6}$ alkyl, $C_{1-6}$ alkenyl, $C_{1-6}$ alkynyl, or $C_{3-12}$ cycloalkyl; $R_2$, $R_3$ and $R_4$ are H; X is N, and both Y and Z are chosen independently from CR$_e$; and R$_e$ is: —H, or —C$_{1-6}$alkyl; $R_5$ and $R_6$ are each independently —C$_{1-3}$ alkyl; or $R_5$ and $R_6$ taken together with the carbon to which they attached form a $C_5$ carbocyclic ring; L is: a bond; $R_7$ is: phenyl, or a $C_{4-5}$ heteroaryl containing 1-2 nitrogens as the only heteroatoms in the ring; wherein $R_7$ may be optionally substituted with 0-5 substituents selected from the group consisting of halogen, hydroxy, $C_{1-6}$alkyl, $C_{1-6}$ haloalkyl, $C_{1-6}$ haloalkenyl, haloalkynyl, $C_{3-6}$ cycloalkyl, $C_{1-6}$ alkoxy, $C_{3-6}$ cycloalkyloxy, —S(O)$_m$C$_{1-6}$ alkyl, —S(O)$_m$C$_{3-6}$ cycloalkyl, —CN, —C(O)—NR$_c$R$_d$, —C(O)—OR$_c$, and NR$_c$R$_d$, wherein each R$_c$ and R$_d$ is independently H, $C_{1-6}$ alkyl, $C_{1-6}$ alkenyl, alkynyl or $C_{3-12}$ cycloalkyl; each m is independently 0-2; or a pharmaceutically acceptable salt thereof.

Additional embodiments include any possible combinations of the above sub-embodiments for $R_1$, $R_2$, $R_3$, $R_4$, $R_5$, $R_6$, $R_7$, W, X, Y, Z and L.

In another embodiment, the invention provides made compounds in Table I which can be made in view of the general schemes, examples and methods as described herein.

TABLE I

Table of Compounds

| Example | Structure | HPLC Method | RT (min) | m/z[M + H]$^+$ |
|---------|-----------|-------------|----------|----------------|
| 1 | 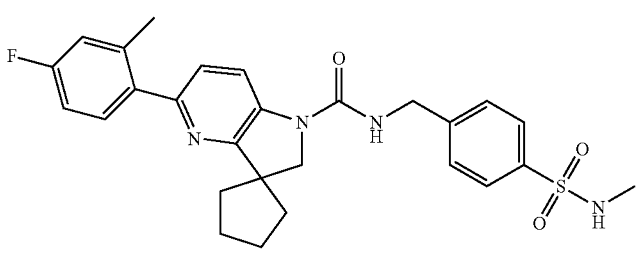 [SMILES: CNS(=O)(=O)c1ccc(CNC(=O)N2CC3(CCCC3)c3nc(-c4ccc(F)cc4C)ccc32)cc1] | C | 3.13 | 509.3 |

TABLE I-continued

Table of Compounds

| Example | Structure | HPLC Method | RT (min) | m/z[M + H]$^+$ |
|---|---|---|---|---|
| 2 | 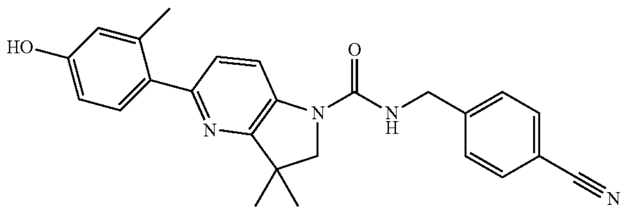 [SMILES: Cc1cc(O)ccc1-c1ccc2c(n1)C(C)(C)CN2C(=O)NCc1ccc(C#N)cc1] | C | 2.91 | 413.2 |
| 3 | 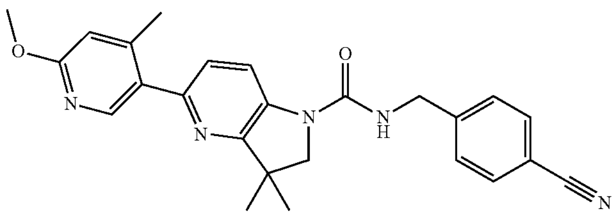 [SMILES: COc1cc(C)c(-c2ccc3c(n2)C(C)(C)CN3C(=O)NCc2ccc(C#N)cc2)cn1] | C | 3.11 | 428.3 |
| 4 | 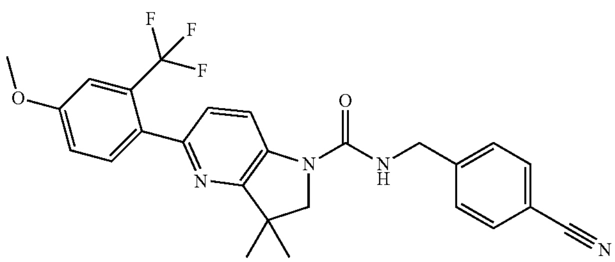 [SMILES: COc1ccc(-c2ccc3c(n2)C(C)(C)CN3C(=O)NCc2ccc(C#N)cc2)c(C(F)(F)F)c1] | C | 3.35 | 480.1 |
| 5 | 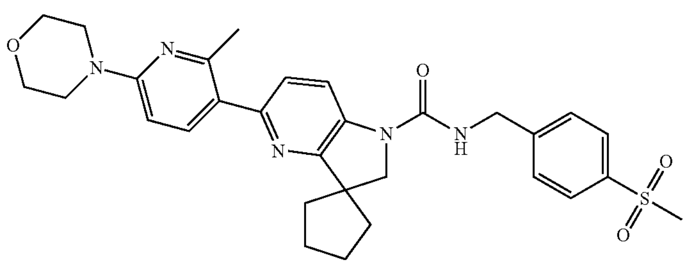 [SMILES: Cc1nc(N2CCOCC2)ccc1-c1ccc2c(n1)C1(CCCC1)CN2C(=O)NCc1ccc(S(C)(=O)=O)cc1] | C | 2.66 | 562.4 |
| 6 | 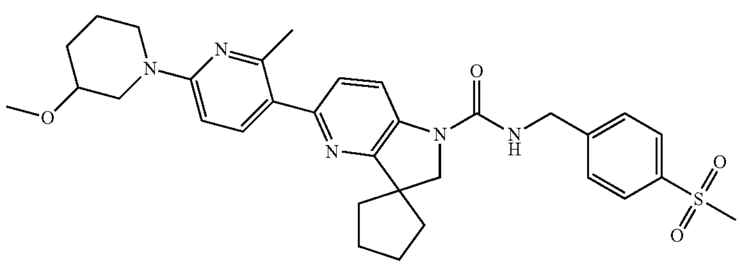 | C | 2.89 | 590.4 |
| 7 | 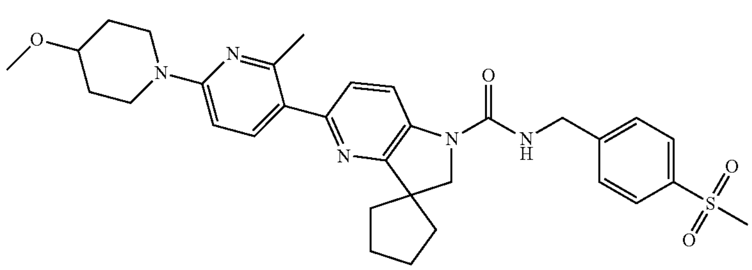 | C | 2.86 | 590.4 |

TABLE I-continued

Table of Compounds

| Example | Structure | HPLC Method | RT (min) | m/z[M + H]+ |
|---------|-----------|-------------|----------|-------------|
| 8 | 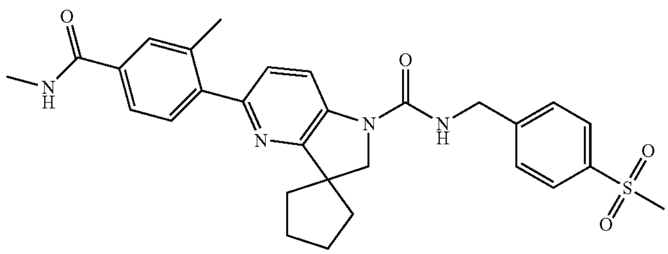 | C | 2.93 | 533.3 |
| 9 | 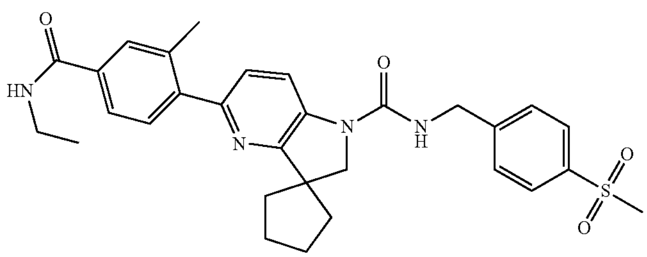 [SMILES: CCNC(=O)c1ccc(-c2ccc3c(n2)C2(CCCC2)CN3C(=O)NCc2ccc(S(C)(=O)=O)cc2)c(C)c1] | C | 2.99 | 547.4 |
| 10 | 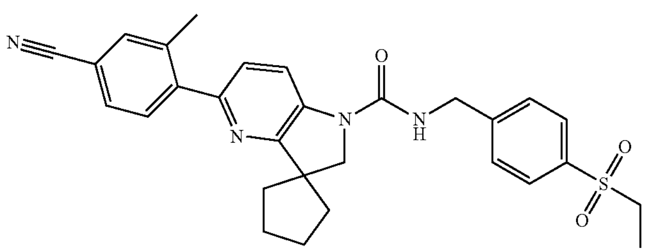 [SMILES: CCS(=O)(=O)c1ccc(CNC(=O)N2CC3(CCCC3)c3nc(-c4ccc(C#N)cc4C)ccc32)cc1] | C | 3.16 | 515.4 |
| 11 | 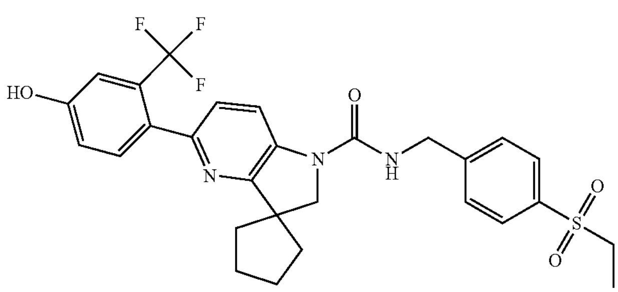 [SMILES: CCS(=O)(=O)c1ccc(CNC(=O)N2CC3(CCCC3)c3nc(-c4ccc(O)cc4C(F)(F)F)ccc32)cc1] | C | 2.99 | 560.3 |
| 12 | 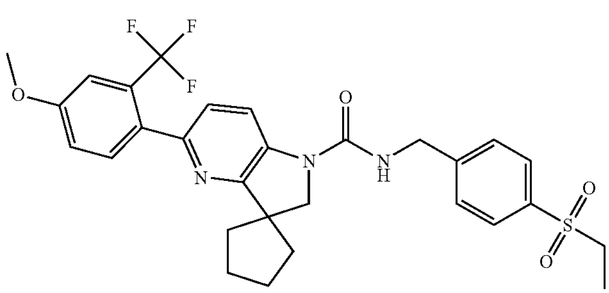 [SMILES: CCS(=O)(=O)c1ccc(CNC(=O)N2CC3(CCCC3)c3nc(-c4ccc(OC)cc4C(F)(F)F)ccc32)cc1] | C | 3.18 | 574.3 |

TABLE I-continued

Table of Compounds

| Example | Structure | HPLC Method | RT (min) | m/z[M + H]+ |
|---|---|---|---|---|
| 13 | 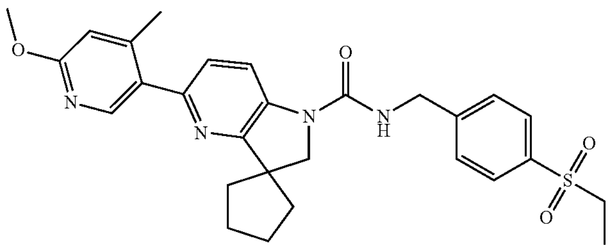 [SMILES: CCS(=O)(=O)c1ccc(CNC(=O)N2CC3(CCCC3)c3nc(-c4cnc(OC)cc4C)ccc32)cc1] | C | 3.14 | 521.3 |
| 14 | 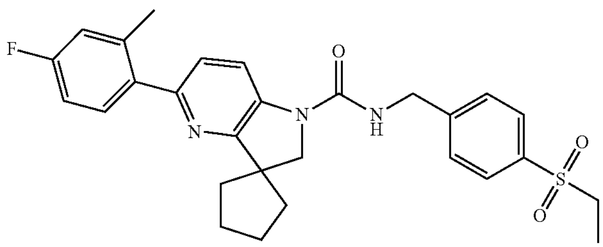 [SMILES: CCS(=O)(=O)c1ccc(CNC(=O)N2CC3(CCCC3)c3nc(-c4ccc(F)cc4C)ccc32)cc1] | C | 3.2 | 508.2 |
| 15 | 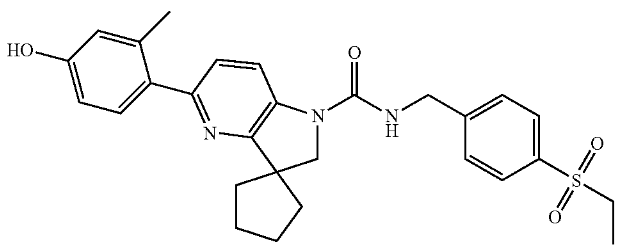 [SMILES: CCS(=O)(=O)c1ccc(CNC(=O)N2CC3(CCCC3)c3nc(-c4ccc(O)cc4C)ccc32)cc1] | C | 2.93 | 506.4 |
| 16 | 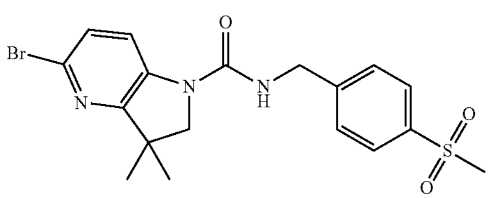 [SMILES: CC1(C)CN(C(=O)NCc2ccc(S(C)(=O)=O)cc2)c2ccc(Br)nc21] | C | 2.79 | 438.0 |
| 17 | 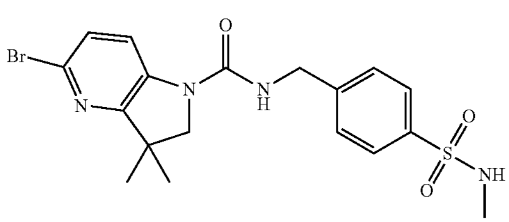 [SMILES: CNS(=O)(=O)c1ccc(CNC(=O)N2CC(C)(C)c3nc(Br)ccc32)cc1] | C | 2.79 | 453.1 |
| 18 | 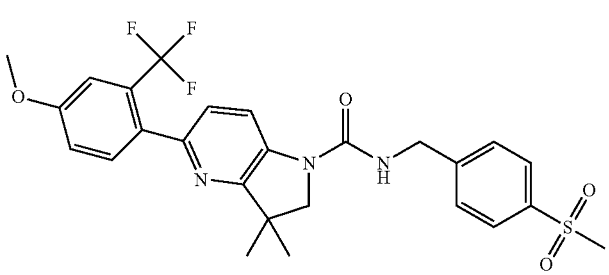 | C | 2.95 | 534.2 |

TABLE I-continued

Table of Compounds

| Example | Structure | HPLC Method | RT (min) | m/z[M + H]+ |
|---------|-----------|-------------|----------|-------------|
| 19 | 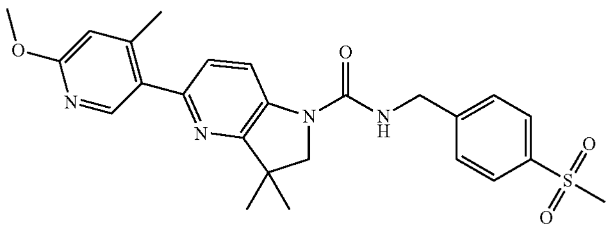 | C | 2.85 | 481.3 |
| 20 | 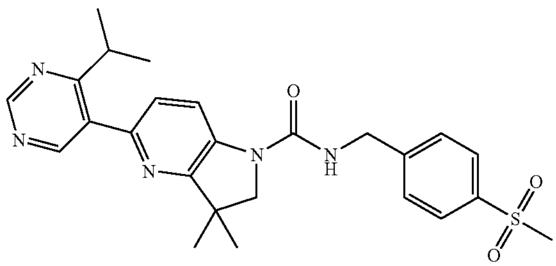 [SMILES: CC(C)c1ncncc1-c1ccc2c(n1)C(C)(C)CN2C(=O)NCc1ccc(S(C)(=O)=O)cc1] | C | 2.85 | 480.3 |
| 21 | 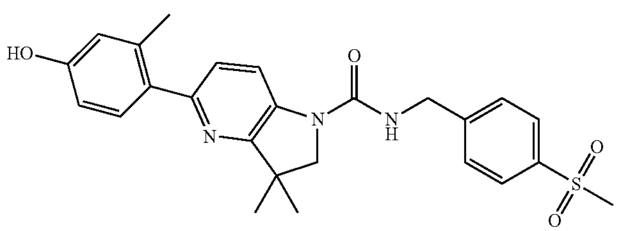 [SMILES: Cc1cc(O)ccc1-c1ccc2c(n1)C(C)(C)CN2C(=O)NCc1ccc(S(C)(=O)=O)cc1] | C | 2.68 | 466.3 |
| 22 | 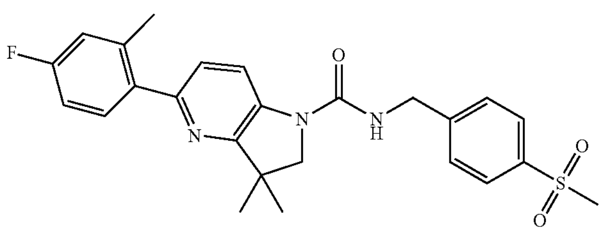 [SMILES: Cc1cc(F)ccc1-c1ccc2c(n1)C(C)(C)CN2C(=O)NCc1ccc(S(C)(=O)=O)cc1] | C | 2.95 | 468.3 |
| 23 | 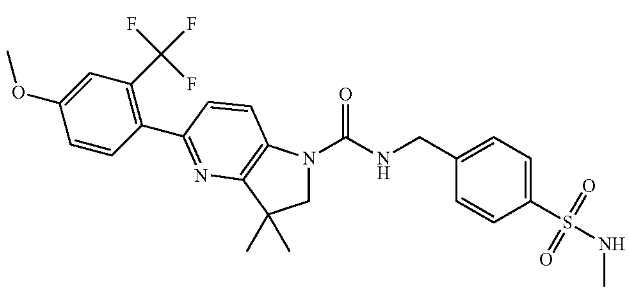 | C | 3.19 | 549.3 |
| 24 | 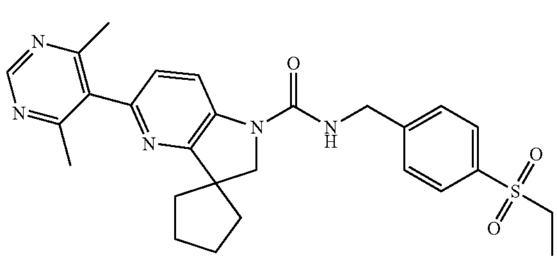 [SMILES: CCS(=O)(=O)c1ccc(CNC(=O)N2CC3(CCCC3)c3nc(-c4c(C)ncnc4C)ccc32)cc1] | C | 3.09 | 506.4 |

TABLE I-continued

Table of Compounds

| Example | Structure | HPLC Method | RT (min) | m/z[M + H]+ |
|---|---|---|---|---|
| 25 | 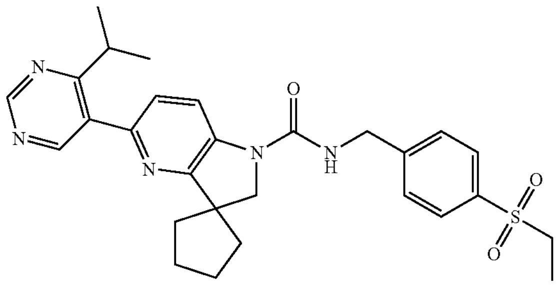 [SMILES: CCS(=O)(=O)c1ccc(CNC(=O)N2CC3(CCCC3)c3nc(-c4cncnc4C(C)C)ccc32)cc1] | C | 3.08 | 520.3 |
| 26 | 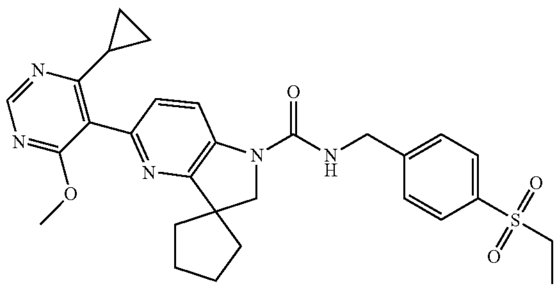 [SMILES: CCS(=O)(=O)c1ccc(CNC(=O)N2CC3(CCCC3)c3nc(-c4c(OC)ncnc4C4CC4)ccc32)cc1] | C | 3.05 | 548.1 |
| 27 | 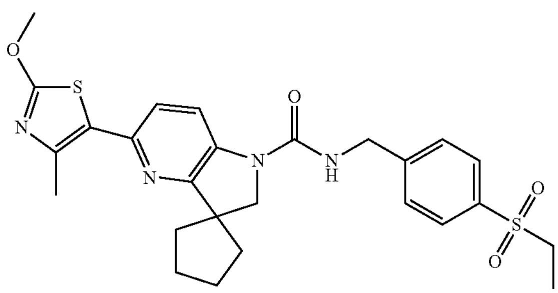 [SMILES: CCS(=O)(=O)c1ccc(CNC(=O)N2CC3(CCCC3)c3nc(-c4sc(OC)nc4C)ccc32)cc1] | C | 3.26 | 527.3 |
| 28 | 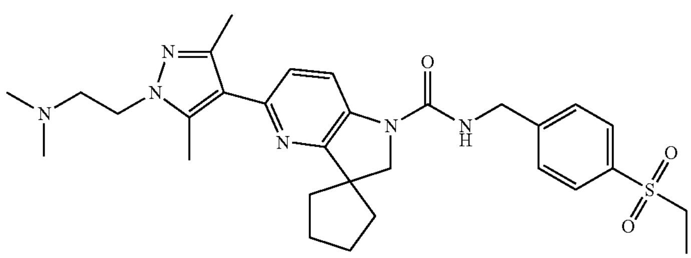 [SMILES: CCS(=O)(=O)c1ccc(CNC(=O)N2CC3(CCCC3)c3nc(-c4c(C)nn(CCN(C)C)c4C)ccc32)cc1] | C | 2.64 | 565.4 |
| 29 | 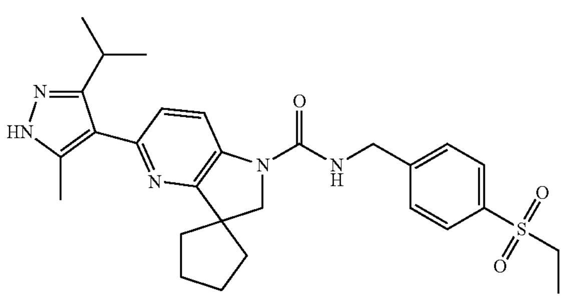 [SMILES: CCS(=O)(=O)c1ccc(CNC(=O)N2CC3(CCCC3)c3nc(-c4c(C(C)C)n[nH]c4C)ccc32)cc1] | C | 2.87 | 522.3 |

TABLE I-continued

Table of Compounds

| Example | Structure | HPLC Method | RT (min) | m/z[M + H]+ |
|---|---|---|---|---|
| 30 | 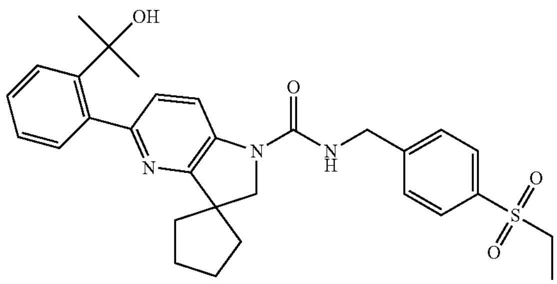 [SMILES: CCS(=O)(=O)c1ccc(CNC(=O)N2CC3(CCCC3)c3nc(-c4ccccc4C(C)(C)O)ccc32)cc1] | C | 2.72 | 583.5 |
| 31 | 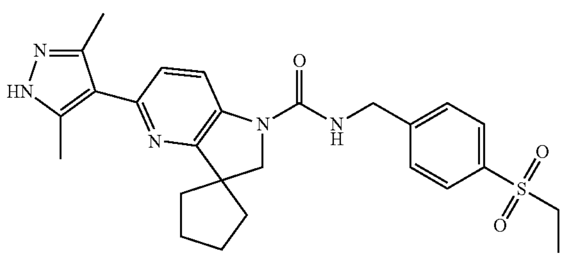 [SMILES: CCS(=O)(=O)c1ccc(CNC(=O)N2CC3(CCCC3)c3nc(-c4c(C)n[nH]c4C)ccc32)cc1] | C | 2.86 | 494.2 |
| 32 | 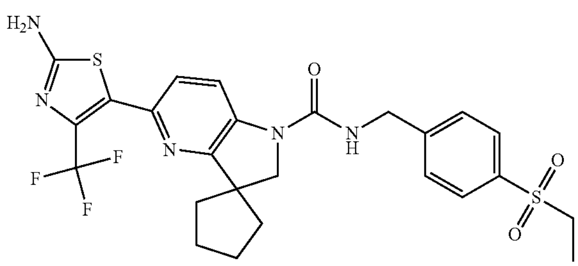 [SMILES: CCS(=O)(=O)c1ccc(CNC(=O)N2CC3(CCCC3)c3nc(-c4sc(N)nc4C(F)(F)F)ccc32)cc1] | C | 2.9 | 566.3 |
| 33 | 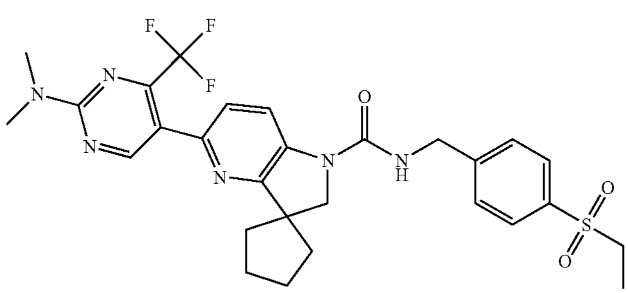 [SMILES: CCS(=O)(=O)c1ccc(CNC(=O)N2CC3(CCCC3)c3nc(-c4cnc(N(C)C)nc4C(F)(F)F)ccc32)cc1] | C | 3.17 | 589.4 |
| 34 | 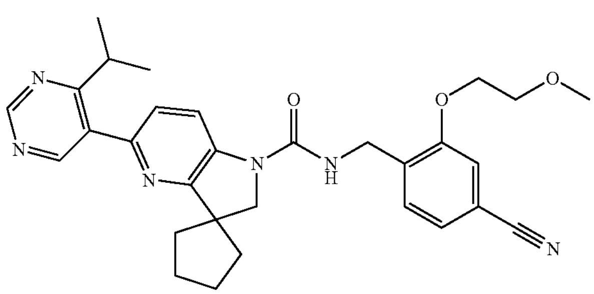 [SMILES: COCCOc1cc(C#N)ccc1CNC(=O)N1CC2(CCCC2)c2nc(-c3cncnc3C(C)C)ccc21] | C | 3.36 | 527.4 |

TABLE I-continued

Table of Compounds

| Example | Structure | HPLC Method | RT (min) | m/z[M + H]+ |
|---|---|---|---|---|
| 35 | 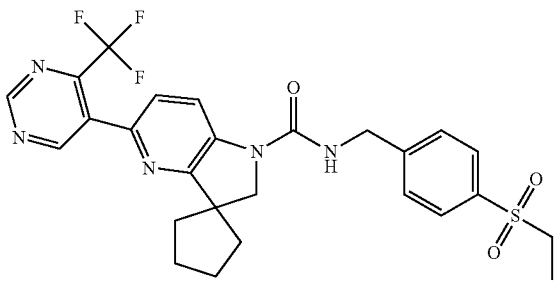 [SMILES: CCS(=O)(=O)c1ccc(CNC(=O)N2CC3(CCCC3)c3nc(-c4cncnc4C(F)(F)F)ccc32)cc1] | C | 3.03 | 546.3 |
| 36 | 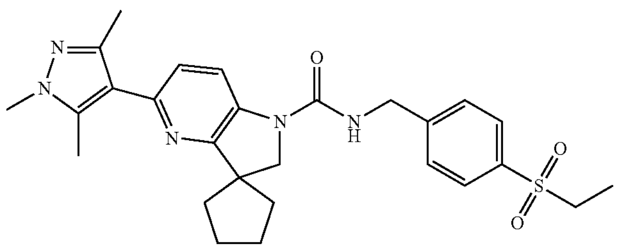 [SMILES: CCS(=O)(=O)c1ccc(CNC(=O)N2CC3(CCCC3)c3nc(-c4c(C)nn(C)c4C)ccc32)cc1] | C | 3.05 | 508.3 |
| 37 | 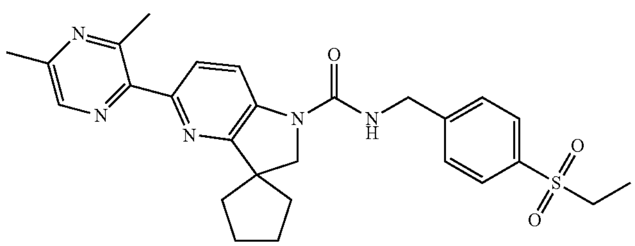 [SMILES: CCS(=O)(=O)c1ccc(CNC(=O)N2CC3(CCCC3)c3nc(-c4ncc(C)nc4C)ccc32)cc1] | C | 3.1 | 506.3 |
| 38 | 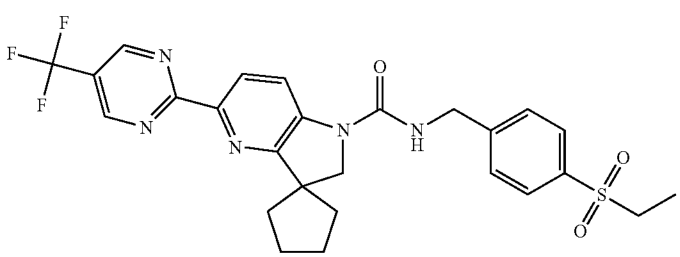 [SMILES: CCS(=O)(=O)c1ccc(CNC(=O)N2CC3(CCCC3)c3nc(-c4ncc(C(F)(F)F)cn4)ccc32)cc1] | C | 3.05 | 546.3 |
| 39 | 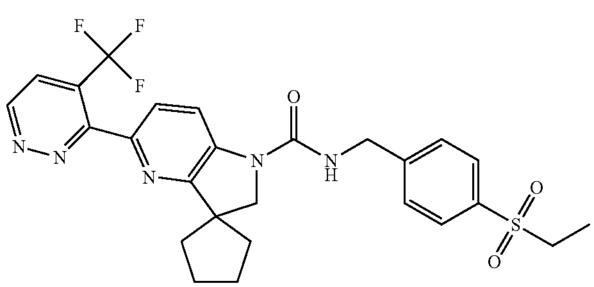 [SMILES: CCS(=O)(=O)c1ccc(CNC(=O)N2CC3(CCCC3)c3nc(-c4nnccc4C(F)(F)F)ccc32)cc1] | C | 3.01 | 546.3 |

TABLE I-continued

Table of Compounds

| Example | Structure | HPLC Method | RT (min) | m/z[M + H]+ |
|---|---|---|---|---|
| 40 | 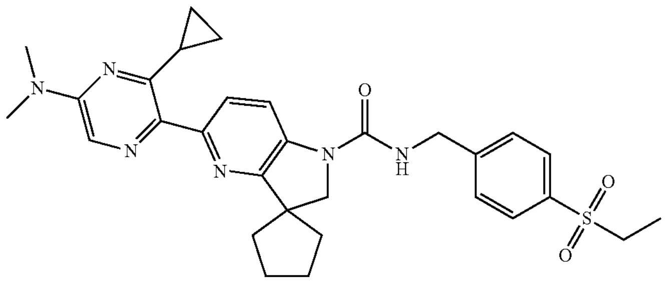 [SMILES: CCS(=O)(=O)c1ccc(CNC(=O)N2CC3(CCCC3)c3nc(-c4ncc(N(C)C)nc4C4CC4)ccc32)cc1] | C | 3.24 | 561.3 |
| 41 | 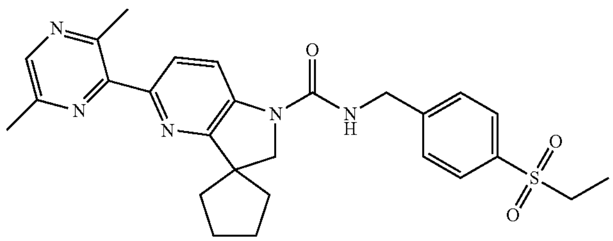 [SMILES: CCS(=O)(=O)c1ccc(CNC(=O)N2CC3(CCCC3)c3nc(-c4nc(C)cnc4C)ccc32)cc1] | C | 3.04 | 506.3 |
| 42 | 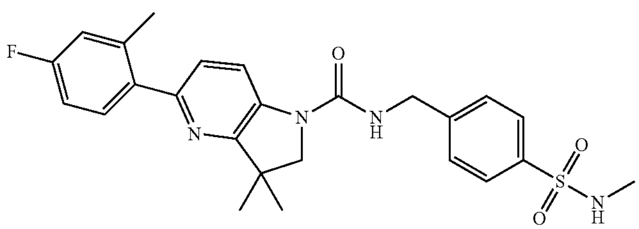 [SMILES: CNS(=O)(=O)c1ccc(CNC(=O)N2CC(C)(C)c3nc(-c4ccc(F)cc4C)ccc32)cc1] | C | 2.95 | 483.3 |
| 43 | 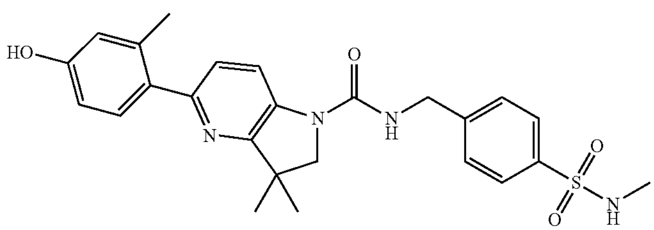 [SMILES: CNS(=O)(=O)c1ccc(CNC(=O)N2CC(C)(C)c3nc(-c4ccc(O)cc4C)ccc32)cc1] | C | 2.69 | 481.4 |
| 44 | 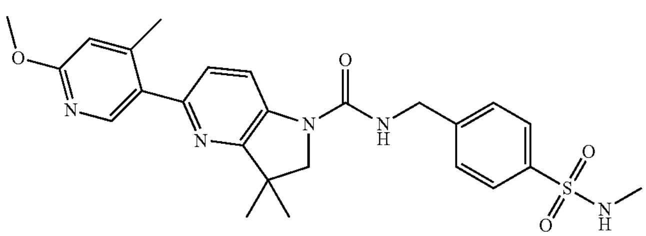 | C | 2.85 | 496.2 |
| 45 | 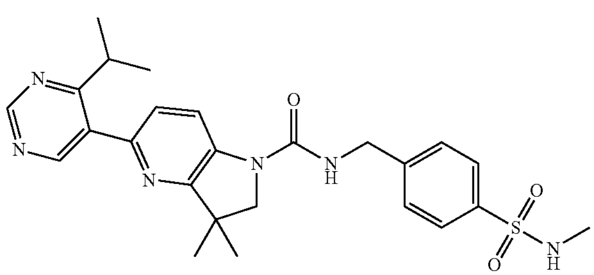 [SMILES: CNS(=O)(=O)c1ccc(CNC(=O)N2CC(C)(C)c3nc(-c4cncnc4C(C)C)ccc32)cc1] | C | 2.84 | 495.3 |

TABLE I-continued

Table of Compounds

| Example | Structure | HPLC Method | RT (min) | m/z[M + H]+ |
|---------|-----------|-------------|----------|-------------|
| 46 | 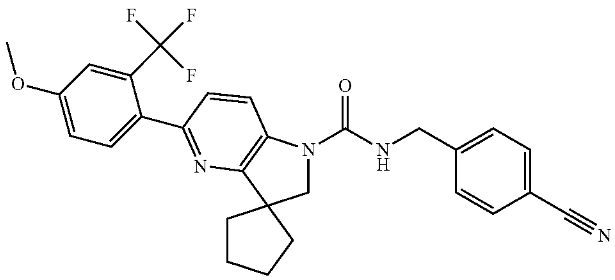 [SMILES: COc1ccc(-c2ccc3c(n2)C2(CCCC2)CN3C(=O)NCc2ccc(C#N)cc2)c(C(F)(F)F)c1] | C | 3.18 | 507.2 |
| 47 | 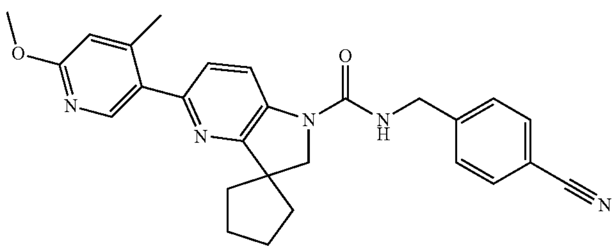 [SMILES: COc1cc(C)c(-c2ccc3c(n2)C2(CCCC2)CN3C(=O)NCc2ccc(C#N)cc2)cn1] | C | 3.16 | 454.3 |
| 48 | 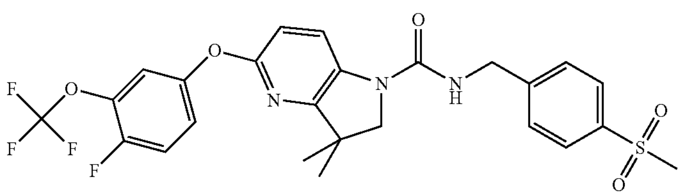 [SMILES: CC1(C)CN(C(=O)NCc2ccc(S(C)(=O)=O)cc2)c2ccc(Oc3ccc(F)c(OC(F)(F)F)c3)nc21] | C | 3.16 | 554.3 |
| 49 | 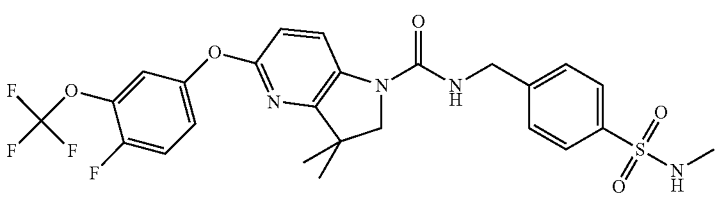 [SMILES: CNS(=O)(=O)c1ccc(CNC(=O)N2CC(C)(C)c3nc(Oc4ccc(F)c(OC(F)(F)F)c4)ccc32)cc1] | C | 3.15 | 569.3 |
| 50 | 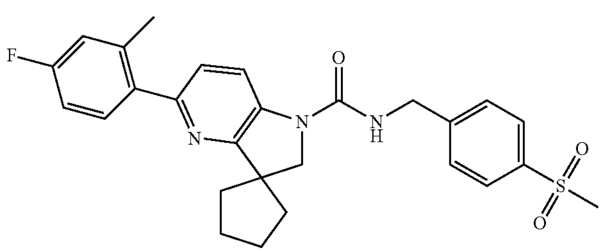 [SMILES: Cc1cc(F)ccc1-c1ccc2c(n1)C1(CCCC1)CN2C(=O)NCc1ccc(S(C)(=O)=O)cc1] | C | 3.14 | 494.3 |
| 51 | 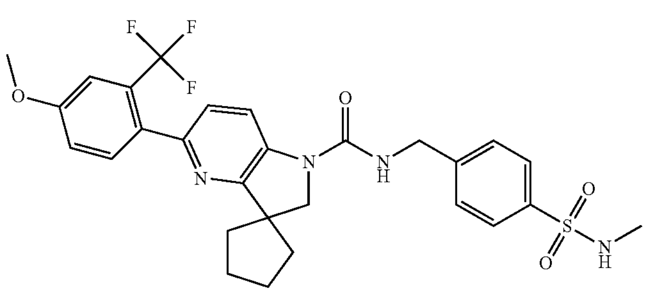 | C | 3.03 | 575.3 |

TABLE I-continued

Table of Compounds

| Example | Structure | HPLC Method | RT (min) | m/z[M + H]+ |
|---|---|---|---|---|
| 52 | 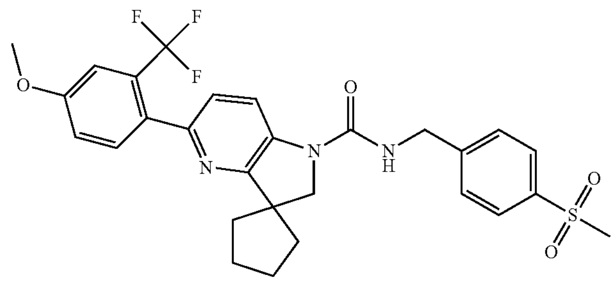 | C | 3.05 | 560.3 |
| 53 | 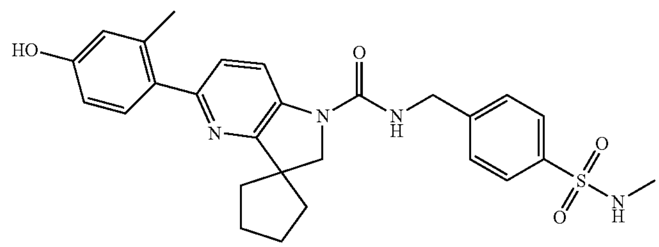 [SMILES: CNS(=O)(=O)c1ccc(CNC(=O)N2CC3(CCCC3)c3nc(-c4ccc(O)cc4C)ccc32)cc1] | C | 2.76 | 507.2 |
| 54 | 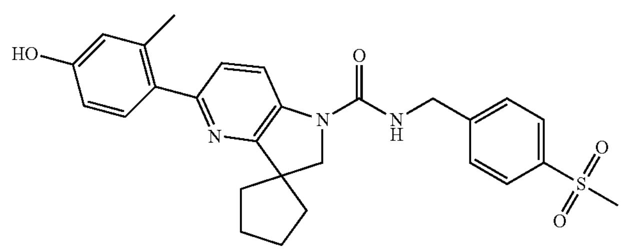 [SMILES: Cc1cc(O)ccc1-c1ccc2c(n1)C1(CCCC1)CN2C(=O)NCc1ccc(S(C)(=O)=O)cc1] | C | 2.76 | 492.3 |
| 55 | 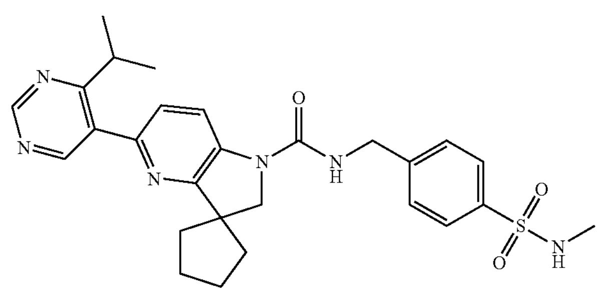 [SMILES: CNS(=O)(=O)c1ccc(CNC(=O)N2CC3(CCCC3)c3nc(-c4cncnc4C(C)C)ccc32)cc1] | C | 2.97 | 521.2 |
| 56 | 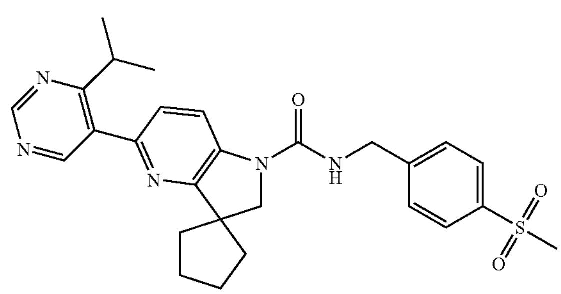 [SMILES: CC(C)c1ncncc1-c1ccc2c(n1)C1(CCCC1)CN2C(=O)NCc1ccc(S(C)(=O)=O)cc1] | C | 2.99 | 506.3 |

TABLE I-continued

Table of Compounds

| Example | Structure | HPLC Method | RT (min) | m/z[M + H]+ |
|---|---|---|---|---|
| 57 | 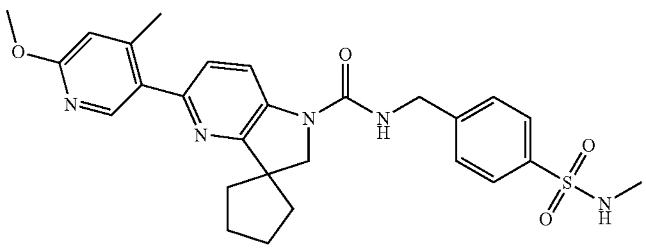 | C | 2.97 | 522.3 |
| 58 | 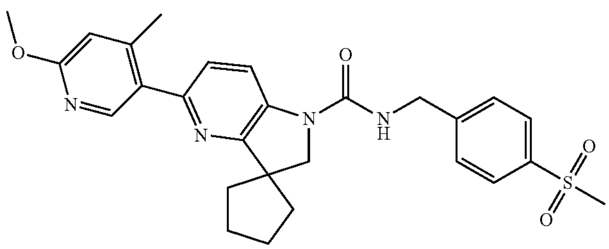 | C | 2.97 | 507.2 |
| 59 | 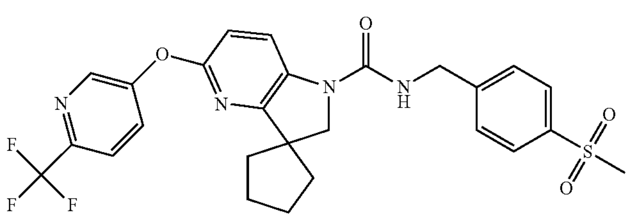 [SMILES: CS(=O)(=O)c1ccc(CNC(=O)N2CC3(CCCC3)c3nc(Oc4ccc(C(F)(F)F)nc4)ccc32)cc1] | C | 3.12 | 547.3 |
| 60 | 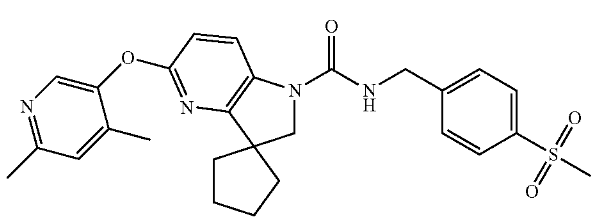 | C | 2.7 | 507.2 |
| 61 | 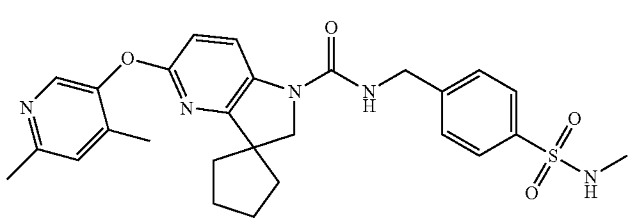 | C | 2.82 | 522.2 |
| 62 | 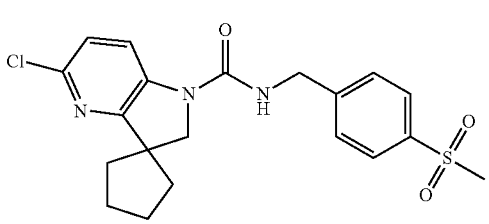 [SMILES: CS(=O)(=O)c1ccc(CNC(=O)N2CC3(CCCC3)c3nc(Cl)ccc32)cc1] | C | 3.1 | 419.1 |

TABLE I-continued

Table of Compounds

| Example | Structure | HPLC Method | RT (min) | m/z[M + H]+ |
|---|---|---|---|---|
| 63 | 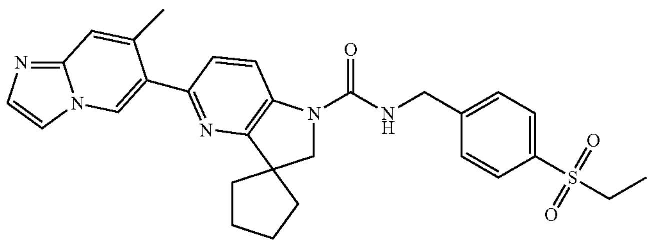 [SMILES: CCS(=O)(=O)c1ccc(CNC(=O)N2CC3(CCCC3)c3nc(-c4cn5ccnc5cc4C)ccc32)cc1] | C | 2.66 | 530.2 |
| 64 | 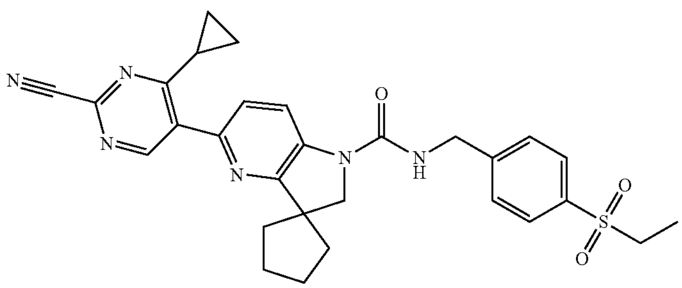 [SMILES: CCS(=O)(=O)c1ccc(CNC(=O)N2CC3(CCCC3)c3nc(-c4cnc(C#N)nc4C4CC4)ccc32)cc1] | C | 3.07 | 543.3 |
| 65 | 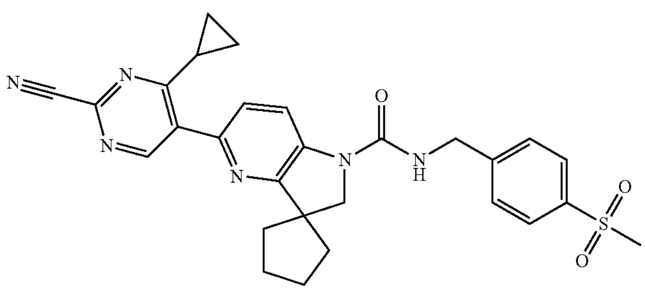 [SMILES: CS(=O)(=O)c1ccc(CNC(=O)N2CC3(CCCC3)c3nc(-c4cnc(C#N)nc4C4CC4)ccc32)cc1] | C | 3.03 | 529.3 |
| 66 | 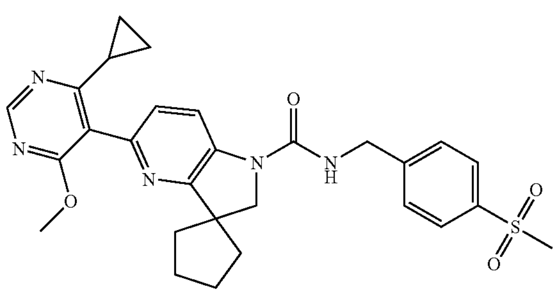 [SMILES: COc1ncnc(C2CC2)c1-c1ccc2c(n1)C1(CCCC1)CN2C(=O)NCc1ccc(S(C)(=O)=O)cc1] | C | 3.19 | 533.2 |
| 67 | 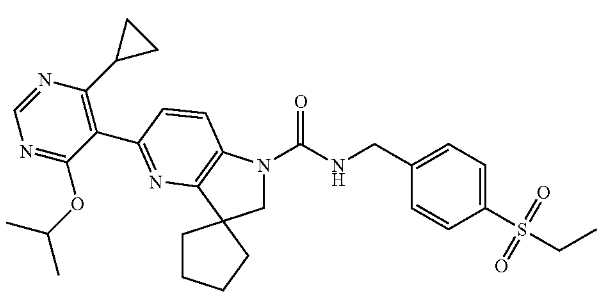 [SMILES: CCS(=O)(=O)c1ccc(CNC(=O)N2CC3(CCCC3)c3nc(-c4c(OC(C)C)ncnc4C4CC4)ccc32)cc1] | C | 3.17 | 576.5 |

TABLE I-continued
Table of Compounds
| Example | Structure | HPLC Method | RT (min) | m/z[M + H]+ |
|---|---|---|---|---|
| 68 | 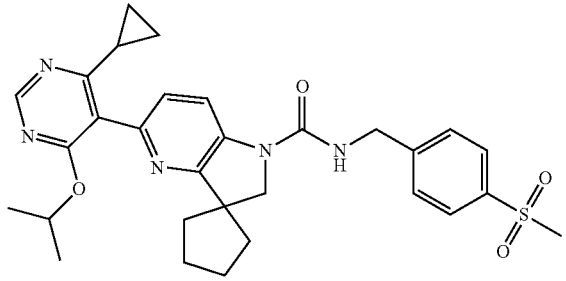 [SMILES: CC(C)Oc1ncnc(C2CC2)c1-c1ccc2c(n1)C1(CCCC1)CN2C(=O)NCc1ccc(S(C)(=O)=O)cc1] | C | 3.12 | 562.3 |
| 69 | 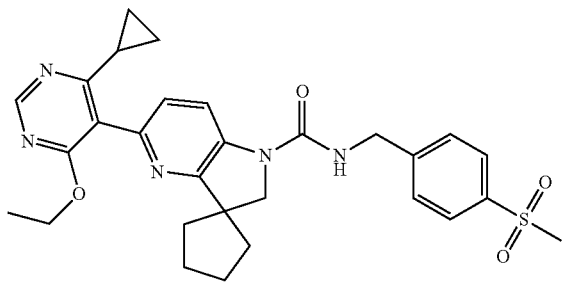 [SMILES: CCOc1ncnc(C2CC2)c1-c1ccc2c(n1)C1(CCCC1)CN2C(=O)NCc1ccc(S(C)(=O)=O)cc1] | C | 3.07 | 548.3 |
| 70 | 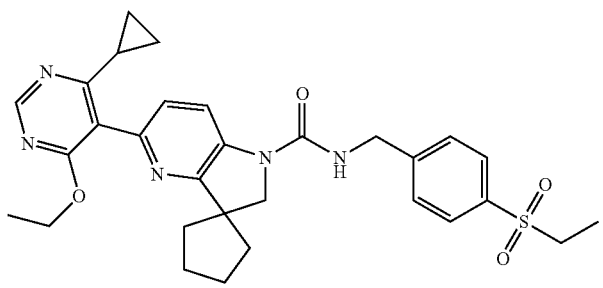 [SMILES: CCOc1ncnc(C2CC2)c1-c1ccc2c(n1)C1(CCCC1)CN2C(=O)NCc1ccc(S(=O)(=O)CC)cc1] | C | 3.12 | 562.3 |
| 71 | 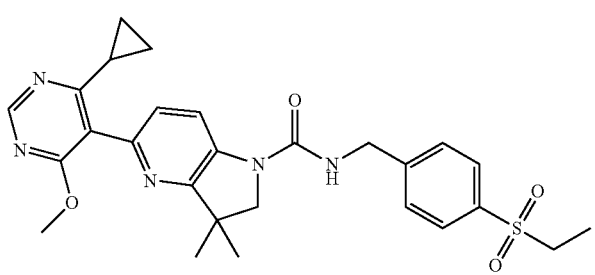 [SMILES: CCS(=O)(=O)c1ccc(CNC(=O)N2CC(C)(C)c3nc(-c4c(OC)ncnc4C4CC4)ccc32)cc1] | C | 2.88 | 522.1 |
| 72 | 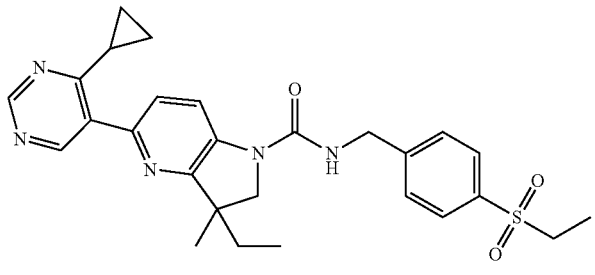 [SMILES: CCC1(C)CN(C(=O)NCc2ccc(S(=O)(=O)CC)cc2)c2ccc(-c3cncnc3C3CC3)nc21] | C | 2.93 | 508.2 |

TABLE I-continued

Table of Compounds

| Example | Structure | HPLC Method | RT (min) | m/z[M + H]+ |
|---|---|---|---|---|
| 73 | 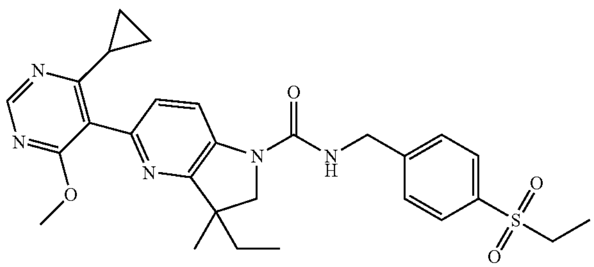 [SMILES: CCC1(C)CN(C(=O)NCc2ccc(S(=O)(=O)CC)cc2)c2ccc(-c3c(OC)ncnc3C3CC3)nc21] | D | 2.88 | 536.3 |
| 74 | 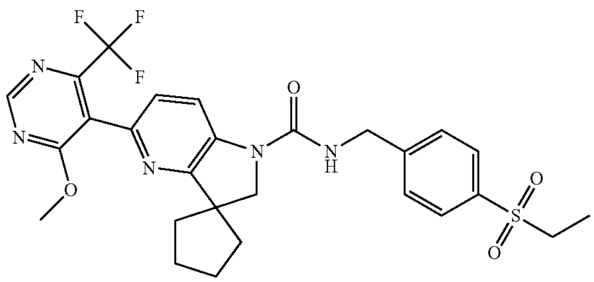 [SMILES: CCS(=O)(=O)c1ccc(CNC(=O)N2CC3(CCCC3)c3nc(-c4c(OC)ncnc4C(F)(F)F)ccc32)cc1] | D | 2.9 | 576.4 |
| 75 | 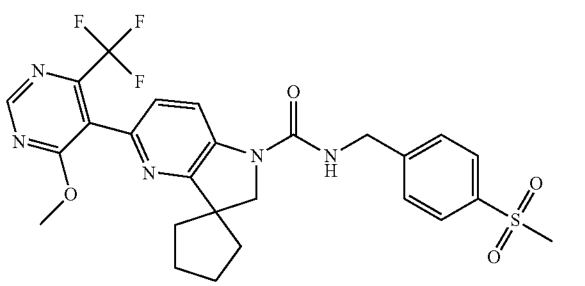 [SMILES: COc1ncnc(C(F)(F)F)c1-c1ccc2c(n1)C1(CCCC1)CN2C(=O)NCc1ccc(S(C)(=O)=O)cc1] | D | 2.93 | 562.2 |
| 76 | 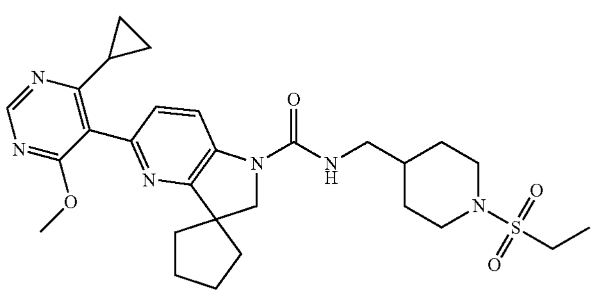 [SMILES: CCS(=O)(=O)N1CCC(CNC(=O)N2CC3(CCCC3)c3nc(-c4c(OC)ncnc4C4CC4)ccc32)CC1] | C | 3.05 | 555.2 |
| 77 | 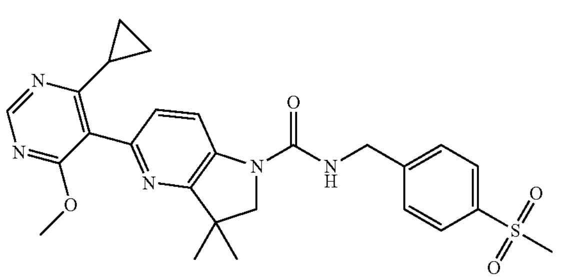 [SMILES: COc1ncnc(C2CC2)c1-c1ccc2c(n1)C(C)(C)CN2C(=O)NCc1ccc(S(C)(=O)=O)cc1] | C | 2.83 | 508.1 |

TABLE I-continued

Table of Compounds

| Example | Structure | HPLC Method | RT (min) | m/z[M + H]+ |
|---|---|---|---|---|
| 78 | 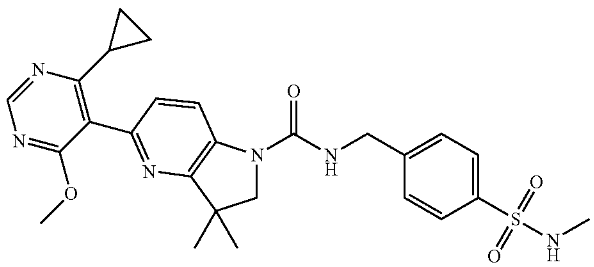 [SMILES: CNS(=O)(=O)c1ccc(CNC(=O)N2CC(C)(C)c3nc(-c4c(OC)ncnc4C4CC4)ccc32)cc1] | C | 2.82 | 523.1 |
| 79 | 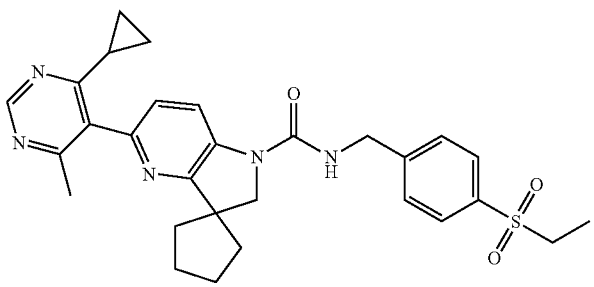 [SMILES: CCS(=O)(=O)c1ccc(CNC(=O)N2CC3(CCCC3)c3nc(-c4c(C)ncnc4C4CC4)ccc32)cc1] | C | 3.1 | 532.3 |
| 80 | 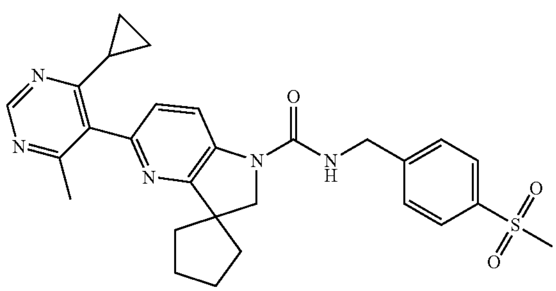 [SMILES: Cc1ncnc(C2CC2)c1-c1ccc2c(n1)C1(CCCC1)CN2C(=O)NCc1ccc(S(C)(=O)=O)cc1] | C | 3.03 | 518.2 |
| 81 | 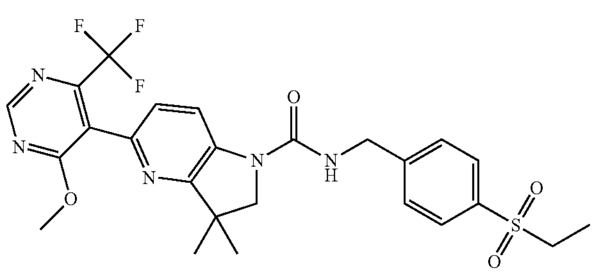 [SMILES: CCS(=O)(=O)c1ccc(CNC(=O)N2CC(C)(C)c3nc(-c4c(OC)ncnc4C(F)(F)F)ccc32)cc1] | C | 2.87 | 549.9 |
| 82 | 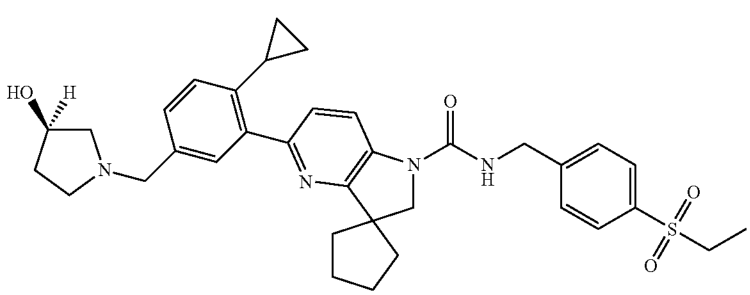 [SMILES: CCS(=O)(=O)c1ccc(CNC(=O)N2CC3(CCCC3)c3nc(-c4cc(CN5CC[C@@H](O)C5)ccc4C4CC4)ccc32)cc1] | C | 2.7 | 615.4 |

TABLE I-continued

Table of Compounds

| Example | Structure | HPLC Method | RT (min) | m/z[M + H]+ |
|---------|-----------|-------------|----------|-------------|
| 83 | 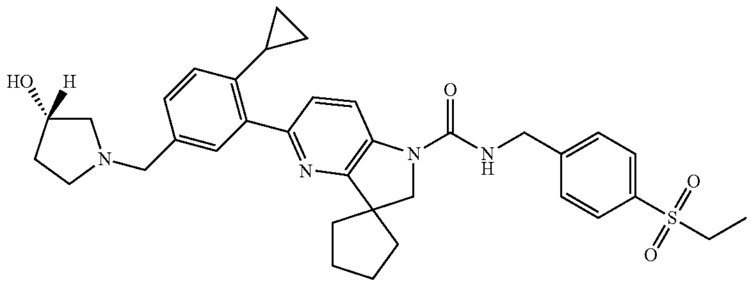 [SMILES: CCS(=O)(=O)c1ccc(CNC(=O)N2CC3(CCCC3)c3nc(-c4cc(CN5CC[C@H](O)C5)ccc4C4CC4)ccc32)cc1] | C | 2.7 | 615.4 |
| 84 | 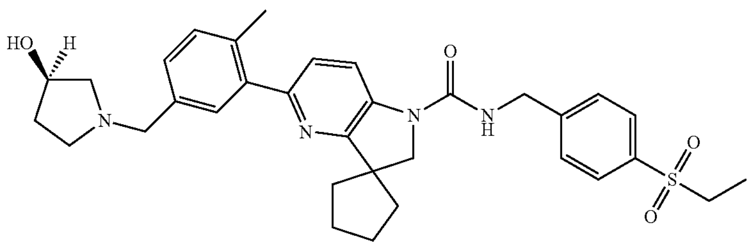 [SMILES: CCS(=O)(=O)c1ccc(CNC(=O)N2CC3(CCCC3)c3nc(-c4cc(CN5CC[C@@H](O)C5)ccc4C)ccc32)cc1] | C | 2.68 | 589.4 |
| 85 | 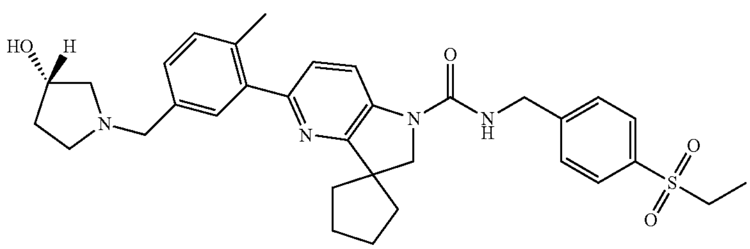 [SMILES: CCS(=O)(=O)c1ccc(CNC(=O)N2CC3(CCCC3)c3nc(-c4cc(CN5CC[C@H](O)C5)ccc4C)ccc32)cc1] | C | 2.68 | 589.4 |
| 86 | 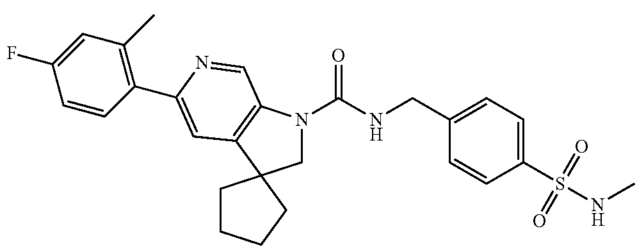 [SMILES: CNS(=O)(=O)c1ccc(CNC(=O)N2CC3(CCCC3)c3cc(-c4ccc(F)cc4C)ncc32)cc1] | C | 2.86 | 509.3 |
| 87 | 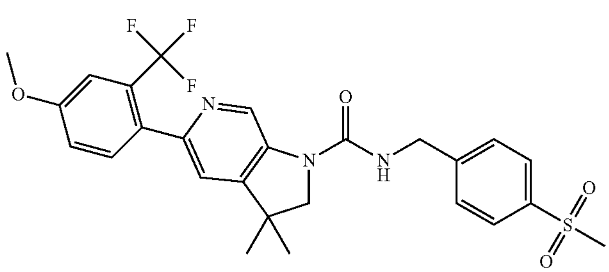 | C | 2.9 | 534.2 |

TABLE I-continued

Table of Compounds

| Example | Structure | HPLC Method | RT (min) | m/z[M + H]+ |
|---|---|---|---|---|
| 88 | 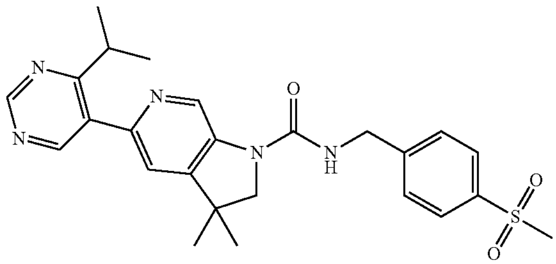 [SMILES: CC(C)c1ncncc1-c1cc2c(cn1)N(C(=O)NCc1ccc(S(C)(=O)=O)cc1)CC2(C)C] | C | 2.8 | 480.3 |
| 89 | 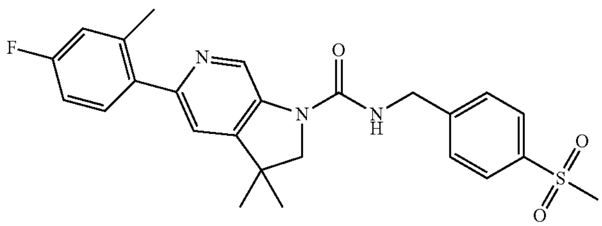 [SMILES: Cc1cc(F)ccc1-c1cc2c(cn1)N(C(=O)NCc1ccc(S(C)(=O)=O)cc1)CC2(C)C] | C | 2.79 | 468.3 |
| 90 | 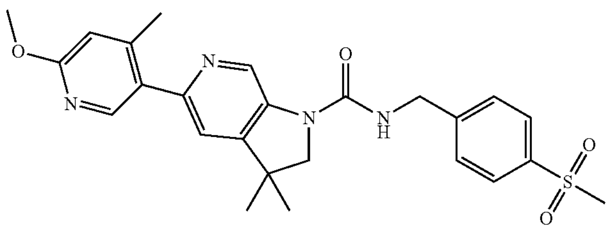 | C | 2.74 | 481.4 |
| 91 | 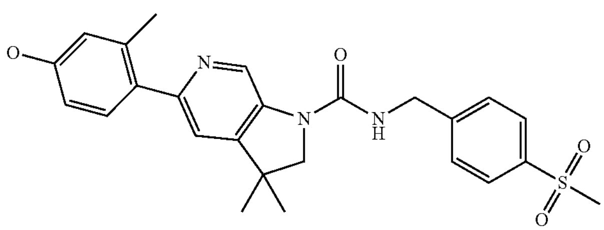 [SMILES: Cc1cc(O)ccc1-c1cc2c(cn1)N(C(=O)NCc1ccc(S(C)(=O)=O)cc1)CC2(C)C] | C | 2.65 | 466.3 |
| 92 | 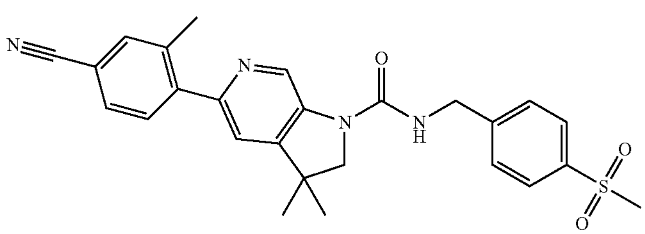 [SMILES: Cc1cc(C#N)ccc1-c1cc2c(cn1)N(C(=O)NCc1ccc(S(C)(=O)=O)cc1)CC2(C)C] | C | 2.82 | 475.3 |
| 93 | 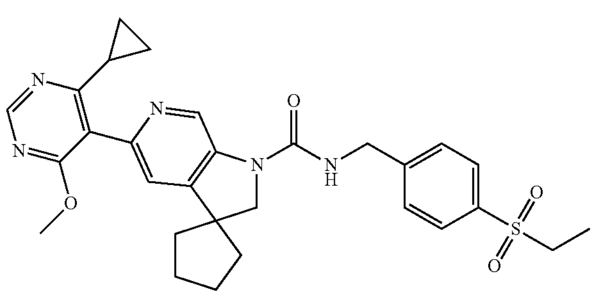 [SMILES: CCS(=O)(=O)c1ccc(CNC(=O)N2CC3(CCCC3)c3cc(-c4c(OC)ncnc4C4CC4)ncc32)cc1] | D | 2.66 | 548.3 |

TABLE I-continued

Table of Compounds

| Example | Structure | HPLC Method | RT (min) | m/z[M + H]+ |
|---------|-----------|-------------|----------|-------------|
| 94 | 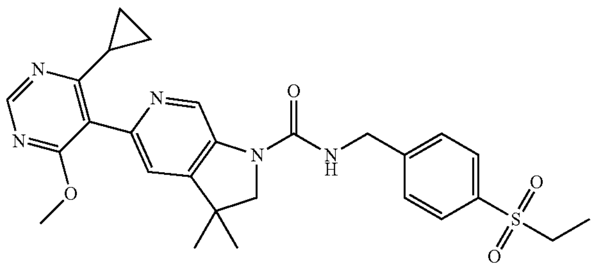 [SMILES: CCS(=O)(=O)c1ccc(CNC(=O)N2CC(C)(C)c3cc(-c4c(OC)ncnc4C4CC4)ncc32)cc1] | C | 2.73 | 522.1 |
| 95 | 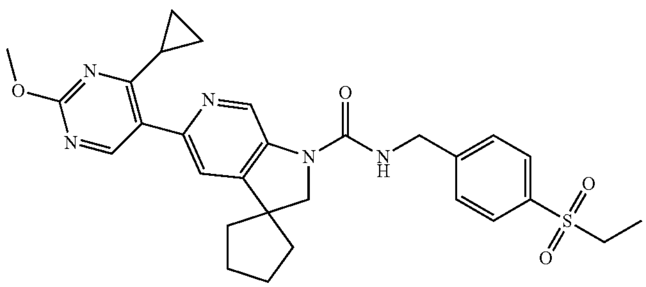 [SMILES: CCS(=O)(=O)c1ccc(CNC(=O)N2CC3(CCCC3)c3cc(-c4cnc(OC)nc4C4CC4)ncc32)cc1] | C | 2.66 | 548.3 |
| 96 | 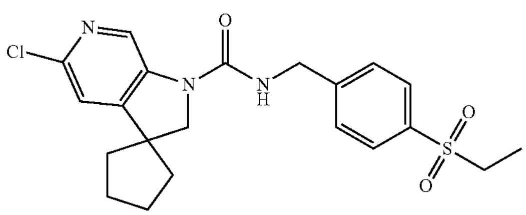 [SMILES: CCS(=O)(=O)c1ccc(CNC(=O)N2CC3(CCCC3)c3cc(Cl)ncc32)cc1] | C | 2.9 | 434.2 |
| 97 | 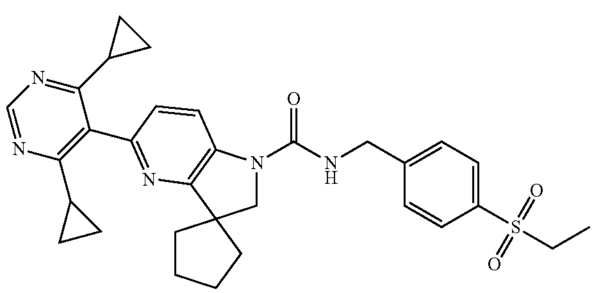 [SMILES: CCS(=O)(=O)c1ccc(CNC(=O)N2CC3(CCCC3)c3nc(-c4c(C5CC5)ncnc4C4CC4)ccc32)cc1] | A | 1.04 | 559.3 |
| 98 | 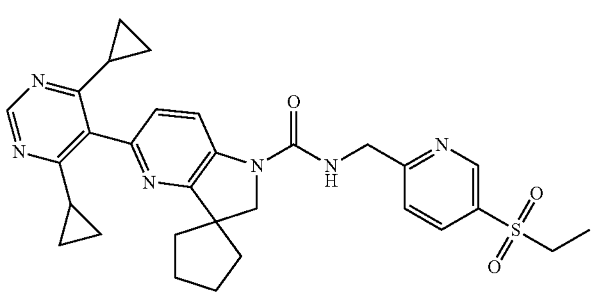 [SMILES: CCS(=O)(=O)c1ccc(CNC(=O)N2CC3(CCCC3)c3nc(-c4c(C5CC5)ncnc4C4CC4)ccc32)nc1] | C | 3.16 | 559.4 |

TABLE I-continued

Table of Compounds

| Example | Structure | HPLC Method | RT (min) | m/z[M + H]+ |
|---|---|---|---|---|
| 99 | 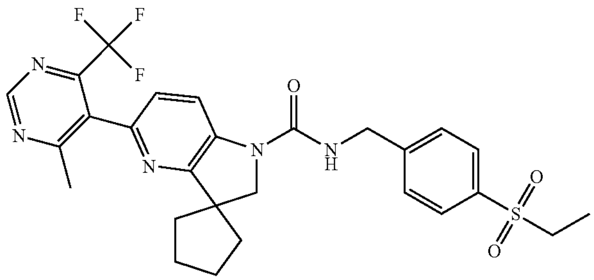 [SMILES: CCS(=O)(=O)c1ccc(CNC(=O)N2CC3(CCCC3)c3nc(-c4c(C)ncnc4C(F)(F)F)ccc32)cc1] | A | 1.01 | 560.2 |
| 100 | 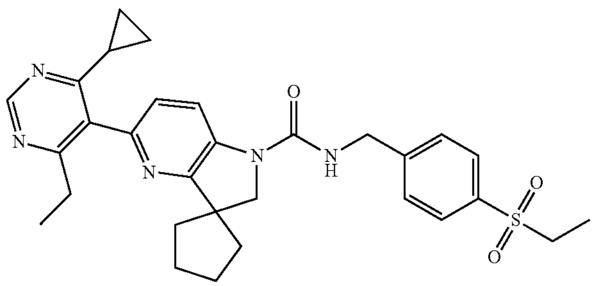 [SMILES: CCc1ncnc(C2CC2)c1-c1ccc2c(n1)C1(CCCC1)CN2C(=O)NCc1ccc(S(=O)(=O)CC)cc1] | C | 2.21 | 546.4 |
| 101 | 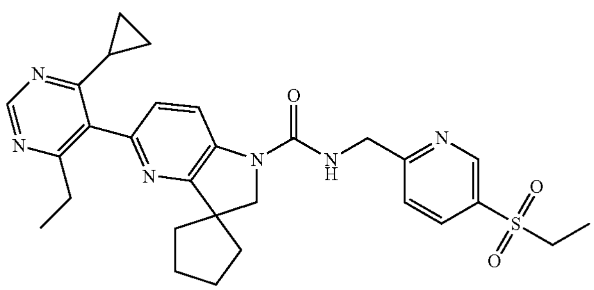 | C | 2.15 | 547.4 |
| 102 | | A | 0.90 | 550.4 | or the pharmaceutically acceptable salts thereof.

The present invention further relates to a pharmaceutically acceptable salt of a compound of the formula (I) with inorganic or organic acids or bases.

In another aspect, the invention relates to compounds of formula (I)—or the pharmaceutically acceptable salts thereof—as medicaments.

In another aspect, the invention relates to compounds of formula (I)—or the pharmaceutically acceptable salts thereof—for use in a method for treatment of a pateint.

In another aspect, the invention relates to compounds of formula (I)—or the pharmaceutically acceptable salts thereof—for use in the treatment of autoimmune diseases and allergic disorders.

In another aspect, the invention relates to the use of compounds of formula (I)—or the pharmaceutically acceptable salts thereof—for preparing a pharmaceutical composition for the treatment of autoimmune diseases and allergic disorders.

In another aspect, the invention relates to a method for the treatment of autoimmune diseases and allergic disorders comprising administering a therapeutically effective amount of a compound of formula (I)—or one of the pharmaceutically acceptable salts thereof—to a patient.

In another aspect, the invention relates to a pharmaceutical preparation containing as active substance one or more compounds of formula (I)—or the pharmaceutically acceptable salts thereof—optionally in combination with conventional excipients and/or carriers.

Definitions and Conventions Used

Terms that are not specifically defined here have the meanings that are apparent to the skilled man in the light of the overall disclosure and the context as a whole.

As used herein, the following definitions apply, unless stated otherwise:

The use of the prefix $C_{x\text{-}y}$, wherein x and y each represent a natural number, indicates that the chain or ring structure or combination of chain and ring structure as a whole, specified and mentioned in direct association, may consist of a maximum of y and a minimum of x carbon atoms.

In general, for groups comprising two or more subgroups, unless otherwise indicated the last named subgroup is the radical attachment point, for example, the substituent "aryl-$C_{1\text{-}3}$-alkyl" means an aryl group which is bound to a $C_{1\text{-}3}$-alkyl-group, the latter of which is bound to the core or to the group to which the substituent is attached. However, if a bond is depicted just prior to the first named subgroup, then that first named subgroup is the radical attachment point, for example, the substituent "—S(O)$_m$C$_{1\text{-}6}$alkyl" means a $C_{1\text{-}6}$-alkyl-group which is bound to an S(O)$_m$ group, the latter of which is bound to the core or to the group to which the substituent is attached.

Alkyl denotes monovalent, saturated hydrocarbon chains, which may be present in both straight-chain (unbranched) and branched form. If an alkyl is substituted, the substitution may take place independently of one another, by mono- or polysubstitution in each case, on all the hydrogen-carrying carbon atoms.

For example, the term "$C_{1\text{-}5}$alkyl" includes for example H$_3$C—, H$_3$C—CH$_2$—, H$_3$C—CH$_2$—CH$_2$—, H$_3$C—CH(CH$_3$)—, H$_3$C—CH$_2$—CH$_2$—CH$_2$—, H$_3$C—CH$_2$—CH(CH$_3$)—, H$_3$C—CH(CH$_3$)—CH$_2$—, H$_3$C—C(CH$_3$)$_2$—, H$_3$C—CH$_2$—CH$_2$—CH$_2$—CH$_2$—, H$_3$C—CH$_2$—CH$_2$—CH(CH$_3$)—, H$_3$C—CH$_2$—CH(CH$_3$)—CH$_2$—, H$_3$C—CH(CH$_3$)—CH$_2$—CH$_2$—, H$_3$C—CH$_2$—C(CH$_3$)$_2$—, H$_3$C—C(CH$_3$)$_2$—CH$_2$—, H$_3$C—CH(CH$_3$)—CH(CH$_3$)— and H$_3$C—CH$_2$—CH(CH$_2$CH$_3$)—.

Further examples of alkyl are methyl (Me; —CH$_3$), ethyl (Et; —CH$_2$CH$_3$), 1-propyl (n-propyl; n-Pr; —CH$_2$CH$_2$CH$_3$), 2-propyl (i-Pr; iso-propyl; —CH(CH$_3$)$_2$), 1-butyl (n-butyl; n-Bu; —CH$_2$CH$_2$CH$_2$CH$_3$), 2-methyl-1-propyl (iso-butyl; i-Bu; —CH$_2$CH(CH$_3$)$_2$), 2-butyl (sec-butyl; sec-Bu; —CH(CH$_3$)CH$_2$CH$_3$), 2-methyl-2-propyl (tert-butyl; t-Bu; —C(CH$_3$)$_3$), 1-pentyl n-pentyl; —CH$_2$CH$_2$CH$_2$CH$_2$CH$_3$), 2-pentyl (—CH(CH$_3$)CH$_2$CH$_2$CH$_3$), 3-pentyl (—CH(CH$_2$CH$_3$)$_2$), 3-methyl-1-butyl (iso-pentyl; —CH$_2$CH$_2$CH(CH$_3$)$_2$), 2-methyl-2-butyl (—C(CH$_3$)$_2$CH$_2$CH$_3$), 3-methyl-2-butyl (—CH(CH$_3$)CH(CH$_3$)$_2$), 2,2-dimethyl-1-propyl(neo-pentyl; —CH$_2$C(CH$_3$)$_3$), 2-methyl-1-butyl (—CH$_2$CH(CH$_3$)CH$_2$CH$_3$), 1-hexyl (n-hexyl; —CH$_2$CH$_2$CH$_2$CH$_2$CH$_2$CH$_3$), 2-hexyl (—CH(CH$_3$)CH$_2$CH$_2$CH$_2$CH$_3$), 3-hexyl (—CH(CH$_2$CH$_3$)(CH$_2$CH$_2$CH$_3$)), 2-methyl-2-pentyl (—C(CH$_3$)$_2$CH$_2$CH$_2$CH$_3$), 3-methyl-2-pentyl (—CH(CH$_3$)CH(CH$_3$)CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C(CH$_3$)$_2$CH(CH$_3$)$_2$), 3,3-dimethyl-2-butyl (—CH(CH$_3$)C(CH$_3$)$_3$), 2,3-dimethyl-1-butyl (—CH$_2$CH(CH$_3$)CH(CH$_3$)CH$_3$), 2,2-dimethyl-1-butyl (—CH$_2$C(CH$_3$)$_2$CH$_2$CH$_3$), 3,3-dimethyl-1-butyl (—CH$_2$CH$_2$C(CH$_3$)$_3$), 2-methyl-1-pentyl (—CH$_2$CH(CH$_3$)CH$_2$CH$_2$CH$_3$), 3-methyl-1-pentyl (—CH$_2$CH$_2$CH(CH$_3$)CH$_2$CH$_3$), 1-heptyl (n-heptyl), 2-methyl-1-hexyl, 3-methyl-1-hexyl, 2,2-dimethyl-1-pentyl, 2,3-dimethyl-1-pentyl, 2,4-dimethyl-1-pentyl, 3,3-dimethyl-1-pentyl, 2,2,3-trimethyl-1-butyl, 3-ethyl-1-pentyl, 1-octyl (n-octyl), 1-nonyl (n-nonyl); 1-decyl (n-decyl) etc.

By the terms propyl, butyl, pentyl, hexyl, heptyl, octyl, nonyl, decyl etc. without any further definition are meant saturated hydrocarbon groups with the corresponding number of carbon atoms, wherein all isomeric forms are included.

The above definition for alkyl also applies if alkyl is a part of another (combined) group such as for example $C_{x\text{-}y}$alkylamino or $C_{x\text{-}y}$alkoxy.

Unlike alkyl, alkenyl consists of at least two carbon atoms, wherein at least two adjacent carbon atoms are joined together by a C—C double bond and a carbon atom can only be part of one C—C double bond. If in an alkyl as hereinbefore defined having at least two carbon atoms, two hydrogen atoms on adjacent carbon atoms are formally removed and the free valencies are saturated to form a second bond, the corresponding alkenyl is formed.

Alkenyl may optionally be present in the cis or trans or E or Z orientation with regard to the double bond(s).

Unlike alkyl, alkynyl consists of at least two carbon atoms, wherein at least two adjacent carbon atoms are joined together by a C—C triple bond. If in an alkyl as hereinbefore defined having at least two carbon atoms, two hydrogen atoms in each case at adjacent carbon atoms are formally removed and the free valencies are saturated to form two further bonds, the corresponding alkynyl is formed.

Haloalkyl (haloalkenyl, haloalkynyl) is derived from the previously defined alkyl (alkenyl, alkynyl) by replacing one or more hydrogen atoms of the hydrocarbon chain independently of one another by halogen atoms, which may be identical or different. If a haloalkyl (haloalkenyl, haloalkynyl) is to be further substituted, the substitutions may take place independently of one another, in the form of mono- or polysubstitutions in each case, on all the hydrogen-carrying carbon atoms.

Examples of haloalkyl (haloalkenyl, haloalkynyl) are —CF$_3$, —CHF$_2$, —CH$_2$F, —CF$_2$CF$_3$, —CHFCF$_3$, —CH$_2$CF$_3$, —CF$_2$CH$_3$, —CHFCH$_3$, —CF$_2$CF$_2$CF$_3$, —CF$_2$CH$_2$CH$_3$, —CF=CF$_2$, —CCl=CH$_2$, —CBr=CH$_2$, —C≡C—CF$_3$, —CHFCH$_2$CH$_3$, —CHFCH$_2$CF$_3$ etc.

Halogen relates to fluorine, chlorine, bromine and/or iodine atms.

The term "$C_{3\text{-}12}$ cycloalkyl" refers to a nonaromatic 3 to 12-membered (but preferably, 3 to 6-membered) monocyclic carbocyclic radical or a nonaromatic 6 to 10-membered fused bicyclic, bridged bicyclic, or spirocyclic carbocyclic radical. The $C_{3\text{-}12}$ cycloalkyl may be either saturated or partially unsaturated, and the carbocycle may be attached by any atom of the cycle which results in the creation of a stable structure. Non-limiting examples of 3 to 10-membered monocyclic carbocycles include cyclopropyl, cyclobutyl, cyclopentyl, cyclopentenyl, cyclohexyl, cyclohexenyl, cycloheptanyl, cycloheptenyl, and cyclohexanone. Non-limiting examples of 6 to 10-membered fused bicyclic carbocyclic radicals include bicyclo[1.1.1]pentane, bicyclo[3.3.0]octane, bicyclo[4.3.0]nonane, and bicyclo[4.4.0]decanyl (decahydronaphthalenyl). Non-limiting examples of 6 to 10-membered bridged bicyclic carbocyclic radicals include bicyclo[2.2.2]heptanyl, bicyclo[2.2.2]octanyl, and bicyclo[3.2.1]octanyl. Non-limiting examples of 6 to 10-membered spirocyclic carbocyclic radicals include but are not limited to spiro[3,3]heptanyl, spiro[3,4]octanyl and spiro[4,4]heptanyl.

The term "$C_{2-10}$ heterocyclyl" refers to a heterocyclic ring system that contains 2-10 carbon atoms and one to four heteroatom groups chosen from NH, NR', oxygen and sulfur wherein R' is $C_{1-6}$ alkyl and includes stable nonaromatic 4-8 membered monocyclic heterocyclic radical or a stable nonaromatic 6 to 11-membered fused bicyclic, bridged bicyclic or spirocyclic heterocyclic radical. The heterocycle may be either saturated or partially unsaturated. Non-limiting examples of nonaromatic 4-8 membered monocyclic heterocyclic radicals include tetrahydrofuranyl, azetidinyl, pyrrolidinyl, pyranyl, tetrahydropyranyl, dioxanyl, thiomorpholinyl, 1,1-dioxo-1.lamda$_6$-thiomorpholinyl, morpholinyl, piperidinyl, piperazinyl, and azepinyl. Non-limiting examples of nonaromatic 6 to 11-membered fused bicyclic radicals include octahydroindolyl, octahydrobenzofuranyl, and octahydrobenzothiophenyl. Non-limiting examples of nonaromatic 6 to 11-membered bridged bicyclic radicals include 2-azabicyclo[2.2.1]heptanyl, 3-azabicyclo[3.1.0]hexanyl, and 3-azabicyclo[3.2.1]octanyl. Non-limiting examples of nonaromatic 6 to 11-membered spirocyclic heterocyclic radicals include 7-aza-spiro[3,3]heptanyl, 7-spiro[3,4]octanyl, and 7-aza-spiro[3,4]octanyl. Sulfur and nitrogen may optionally be present in all the possible oxidation stages (sulphur sulphoxide —SO—, sulphone —SO$_2$—; nitrogen N-oxide).

The term "aryl" refers to an aromatic hydrocarbon rings containing from six to fourteen carbon ring atoms (e.g., a $C_{6-14}$ aryl, preferably $C_{6-10}$ aryl). The term $C_{6-14}$ aryl includes monocyclic rings, fused rings and bicyclic rings where at least one of the rings is aromatic. Non-limiting examples of $C_{6-14}$ aryls include phenyl, indanyl, indenyl, benzocyclobutanyl, dihydronaphthyl, tetrahydronaphthyl, naphthyl, benzocycloheptanyl and benzocycloheptenyl.

As used herein, the term "$C_{2-10}$ heteroaryl" refers to a heteroaromatic ring system that contains 2-10 carbon atoms and 1-4 heteroatom groups selected from N, NH, NR', O and S wherein R' is $C_{1-6}$ alkyl and includes aromatic 5 to 6-membered monocyclic heteroaryls and aromatic 7 to 11-membered heteroaryl bicyclic or fused rings where at least one of the rings is aromatic Non-limiting examples of 5 to 6-membered monocyclic heteroaryl rings include furanyl, oxazolyl, isoxazolyl, oxadiazolyl, pyranyl, thiazolyl, pyrazolyl, pyrrolyl, imidazolyl, tetrazolyl, triazolyl, thienyl, thiadiazolyl, pyridinyl, pyrimidinyl, pyridazinyl, pyrazinyl, triazinyl, and purinyl. Non-limiting examples of 7 to 11-membered heteroaryl bicyclic or fused rings include benzimidazolyl, 1,3-dihydrobenzoimidazol-2-one, quinolinyl, dihydro-2H-quinolinyl, isoquinolinyl, quinazolinyl, indazolyl, thieno[2,3-d]pyrimidinyl, indolyl, isoindolyl, indazolyl, benzotriazolyl, benzofuranyl, benzopyranyl, benzodioxolyl, benzoxazolyl, benzothiazolyl, pyrrolo[2,3-b]pyridinyl, and imidazo[4,5-b]pyridinyl. Sulfur and nitrogen may optionally be present in all the possible oxidation stages (sulphur→sulphoxide —SO—, sulphone —SO$_2$—; nitrogen→N-oxide).

The compounds of the invention are only those which are contemplated to be chemically stable as will be appreciated by those skilled in the art. For example, a compound which would have a "dangling valency", or a carbanion are not compounds contemplated by the inventive methods disclosed herein.

Unless specifically indicated, throughout the specification and appended claims, a given chemical formula or name shall encompass tautomers and all stereo, optical and geometrical isomers (e.g. enantiomers, diastereomers, E/Z isomers, etc.) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof. The compounds and salts of the invention can exist in unsolvated as well as solvated forms with pharmaceutically acceptable solvents such as water, ethanol and the like, and all are considered another aspect of the present invention. The phrase "pharmaceutically acceptable" is employed herein to refer to those compounds, materials, compositions, and/or dosage forms which are, within the scope of sound medical judgement, suitable for use in contact with the tissues of human beings and animals without excessive toxicity, irritation, allergic response, or other problem or complication, and commensurate with a reasonable benefit/risk ratio Pharmaceutically acceptable salts include those derived from pharmaceutically acceptable inorganic and organic acids and bases. Examples of suitable acids include hydrochloric, hydrobromic, sulfuric, nitric, perchloric, fumaric, maleic, phosphoric, glycolic, lactic, salicylic, succinic, toluene-p-sulfuric, tartaric, acetic, citric, methanesulfonic, formic, benzoic, malonic, naphthalene-2-sulfuric and benzenesulfonic acids. Other acids, such as oxalic acid, while not themselves pharmaceutically acceptable, may be employed in the preparation of salts useful as intermediates in obtaining the compounds and their pharmaceutically acceptable acid addition salts.

Further pharmaceutically acceptable salts can be formed with cations from metals like aluminium, calcium, lithium, magnesium, potassium, sodium, zinc and the like (also see Pharmaceutical salts, Birge, S. M. et al., J. Pharm. Sci., (1977), 66, 1-19).

The pharmaceutically acceptable salts of the present invention can be synthesised from the parent compound which contains a basic or acidic moiety by conventional chemical methods. Generally, such salts can be prepared by reacting the free acid or base form of these compounds with a sufficient amount of the appropriate base or acid in water or in an organic diluent like ether, ethyl acetate, ethanol, isopropanol, or acetonitrile, or a mixture thereof.

By a therapeutically effective amount for the purposes of this invention is meant a quantity of substance that is capable of obviating symptoms of illness or alleviating these symptoms, or which prolong the survival of a treated patient.

Some abbreviated notations and their structure correspondences are listed below:

In a representation such as for example

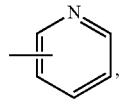

the solid line means that the ring system may be attached to the molecule via the carbon atom 1, 2 or 3, and is thus equivalent to the following representation

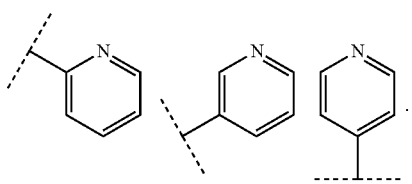

The compounds of formula (I) may be made using the general synthetic methods described below, which also constitute part of the invention.

General Synthetic Methods

The compounds according to the invention may be prepared by the methods of synthesis and synthetic examples described hereinafter in which the substituents of the general formulae have the meanings given hereinbefore. These methods are intended as an illustration of the invention without restricting its subject matter and the scope of the compounds claimed to these examples. Where the preparation of starting compounds is not described, they are commercially obtainable or may be prepared analogously to known compounds or methods described herein. Substances described in the literature are prepared according to the published methods of synthesis.

Compounds of formula I may be prepared from intermediate A as illustrated in Scheme I.

mercially available, readily prepared from commercially available starting materials by methods known in the art or disclosed herein.

SYNTHETIC EXAMPLES

Non-limiting examples demonstrating the preparation of the compounds of the invention are provided below. Optimum reaction conditions and reaction times may vary depending on the particular reactants used. Unless otherwise specified, solvents, temperatures, pressures and other reaction conditions may be readily selected by one of ordinary skill in the art. Specific procedures are provided in the Synthetic Examples section. Intermediates and products may be purified by chromatography on silica gel, recrystallization and/or reverse phase HPLC (RHPLC). Discrete enantiomers may be obtained by resolution of racemic products using chiral HPLC. RHPLC purification methods Scheme I:

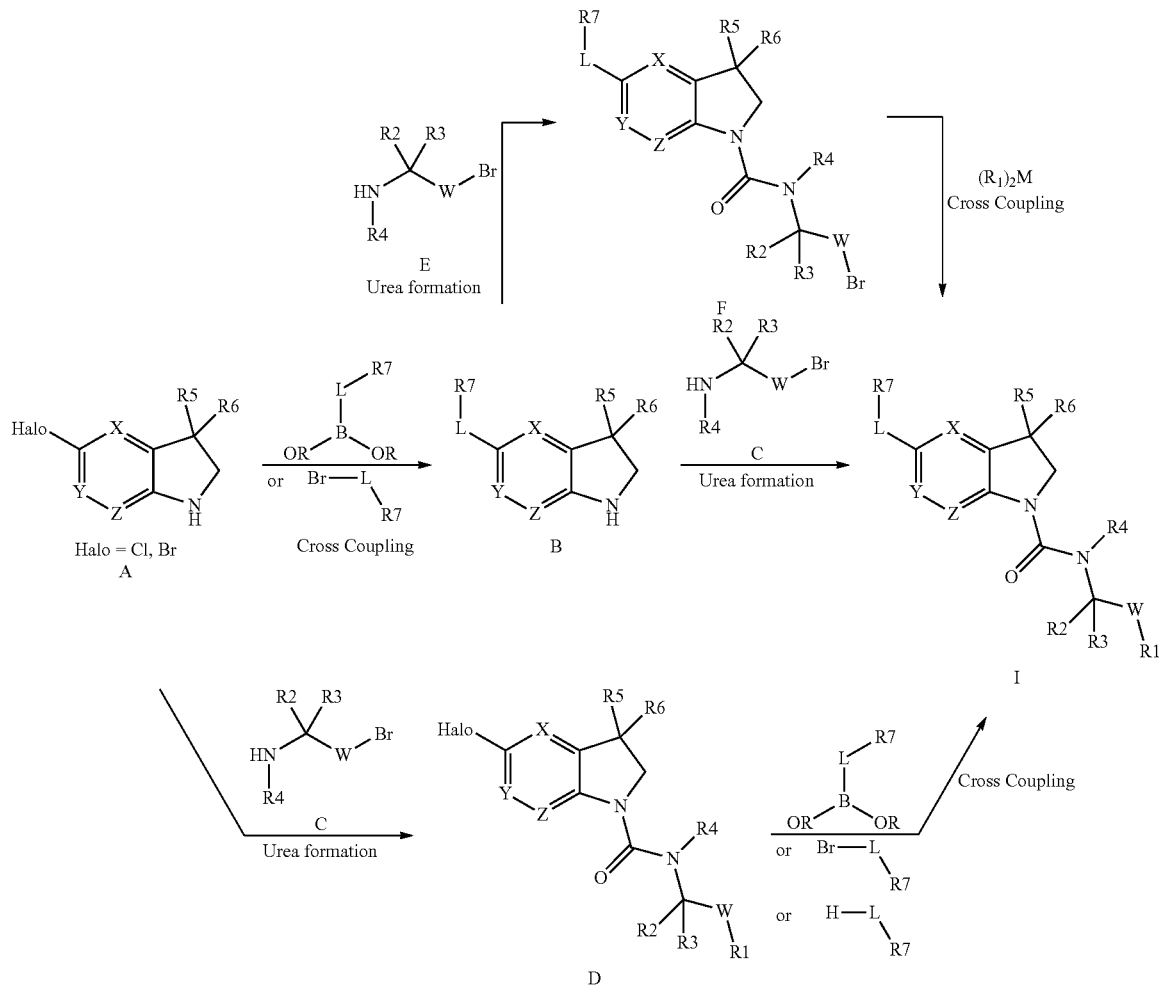

As illustrated above, A is transformed into B under cross coupling conditions. B provides I by either urea formation with a suitably functionalized amine C, or a two step procedure which forms intermediate F prior to final cross coupling to install $R_1$-group. A could also be first transformed to D by urea formation. Then D is further elaborated to I by cross coupling. Intermediates C, E are either commercially available, readily prepared from commercially available starting materials by methods known in the art or disclosed herein.

used anywhere from 0-100% acetonitrile in water containing 0.1% formic acid or 0.1% TFA and used one of the following columns:
  a) Waters Sunfire OBD C18 5 μM 30×150 mm column
  b) Waters XBridge OBD C18 5 μM 30×150 mm column
  c) Waters ODB C8 5 μM 19×150 mm column.
  d) Waters Atlantis ODB C18 5 μM 19×50 mm column.

e) Waters Atlantis T3 OBD 5 µM 30×100 mm column
f) Phenomenex Gemini Axia C18 5 µM 30×100 mm column HPLC Methods:

Analytical LC/MS Analysis Method A:

Column: Thermo Scientific, Aquasil C18, 50×2.1 mm, 5 µm column

Gradient:

| Time (min) | 0.1% Formic Acid in Water | 0.1% Formic Acid in ACN | Flow ml/min) |
|---|---|---|---|
| 0 | 90 | 10 | 0.5 |
| 0.5 | 90 | 10 | 0.5 |
| 1.5 | 1 | 99 | 0.5 |
| 2.5 | 1 | 99 | 0.5 |
| 3.3 | 90 | 10 | 0.5 |
| 4.0 | 90 | 10 | 0.5 |

Analytical LC/MS Analysis Method B:

Column: Waters BEH 2.1×50 mm C18 1.7 µm column

Gradient:

| Time (min) | 95% Water/5% ACN (0.05% TFA) | ACN (0.05% TFA) | Flow (ml/min) |
|---|---|---|---|
| 0 | 90 | 10 | 0.8 |
| 1.19 | 0 | 100 | 0.8 |
| 1.7 | 0 | 100 | 0.8 |

Analytical LC/MS Analysis Method C:

Column: Thermo Scientific, Aquasil C18, 50×2.1 mm, 5 µm, part number 77505-052130, or equivalent Left and Right Temperature: 35° C.

Run Time: 4.0 min

Gradient:

| Total Time (min) | Flow Rate (uL/min) | 0.1% Formic Acid in Water | 0.1% Formic Acid in Acetonitrile |
|---|---|---|---|
| 0 | 500 | 90.0 | 10.0 |
| 0.5 | 500 | 90.0 | 10.0 |
| 1.5 | 500 | 1.0 | 99.0 |
| 2.5 | 500 | 1.0 | 99.0 |
| 3.3 | 500 | 90.0 | 10.0 |
| 4.0 | 500 | 90.0 | 10.0 |

Analytical LC/MS Analysis Method D:

Column: Phenomex Luna 3u C18(2) 100 A, 50×2.00 mm

Left and Right Temperature: 35° C.

Run Time: 4.0 min

Gradient:

| Total Time (min) | Flow Rate (uL/min) | 0.1% Formic Acid in Water | 0.1% Formic Acid in Acetonitrile |
|---|---|---|---|
| 0 | 500 | 90.0 | 10.0 |
| 0.5 | 500 | 90.0 | 10.0 |
| 1.5 | 500 | 1.0 | 99.0 |
| 2.5 | 500 | 1.0 | 99.0 |
| 3.3 | 500 | 90.0 | 10.0 |
| 4.0 | 500 | 90.0 | 10.0 |

List of Abbreviations Used in Synthetic Examples

| | |
|---|---|
| Ac | Acetyl |
| ACN | Acetonitrile |
| AIBN | Azobisisobutyronitrile |
| aq | Aqueous |
| ATP | adenosine triphosphate |
| Bn | Benzyl |
| Bu | Butyl |
| Boc | tert-butyloxycarbonyl |
| cat | Catalyst |
| conc | concentrated |
| d | day(s) |
| TLC | thin layer chromatography |
| DIEA | N,N-diisopropylethylamine |
| DMAP | 4-N,N-dimethylaminopyridine |
| DME | 1,2-dimethoxyethane |
| DMF | N,N-dimethylformamide |
| DMSO | Dimethylsulphoxide |
| dppf | 1,1'-bis(diphenylphosphino)ferrocene |
| EDC | 1-Ethyl-3-(3-dimethylaminopropyl)carbodiimide |
| ESI | electron spray ionization |
| Et | Ethyl |
| $Et_2O$ | diethyl ether |
| EtOAc | ethyl acetate |
| EtOH | Ethanol |
| h | hour(s) |
| HATU | O-(7-azabenzotriazol-1-yl)-N,N,N',N'-tetramethyl-uronium hexafluorophosphate |
| Hep | Heptane |
| HPLC | high performance liquid chromatography |
| i | Iso |
| LC | liquid chromatography |
| LiHMDS | lithium bis(trimethylsilyl)amide |
| sln. | Solution |
| mCPBA | 3-Chloroperoxbenzoic acid |
| Me | Methyl |
| MeOH | Methanol |
| min | Minutes |
| MPLC | medium pressure liquid chromatography |
| MS | mass spectrometry |
| NBS | N-bromo-succinimide |
| NIS | N-iodo-succinimide |
| NMM | N-methylmorpholine |
| NMP | N-methyrpyrrolidone |
| NP | normal phase |
| n.a. | not available |
| PBS | phosphate-buffered saline |
| Ph | Phenyl |
| Pr | Propyl |
| Pyr | Pyridine |
| rac | Racemic |
| Rf ($R_f$) | retention factor |
| RP | reversed phase |
| RT | Retention time (HPLC) |
| rt | ambient temperature |
| TBAF | tetrabutylammonium fluoride |
| TBDMS | tert-butyldimethylsilyl |
| TBME | tert-butylmethylether |
| TBTU | O-(benzotriazol-1-yl)-N,N,N',N'-tetramethyl-uronium tetrafluoroborate |
| tBu | tert-butyl |
| TEA | Triethylamine |
| temp. | Temperature |
| tert | Tertiary |
| Tf | Triflate |
| TFA | trifluoroacetic acid |
| THF | Tetrahydrofuran |
| TMS | Trimethylsilyl |
| TRIS | tris(hydroxymethyl)-aminomethane |
| Ts | p-Tosyl |
| TsOH | p-toluenesurphonic acid |
| UV | Ultraviolet |
| Xphos | 2-Dicyclohexylphosphino-2',4',6'-triisopropylbiphenyl |

Method 1
Synthesis of Intermediate A

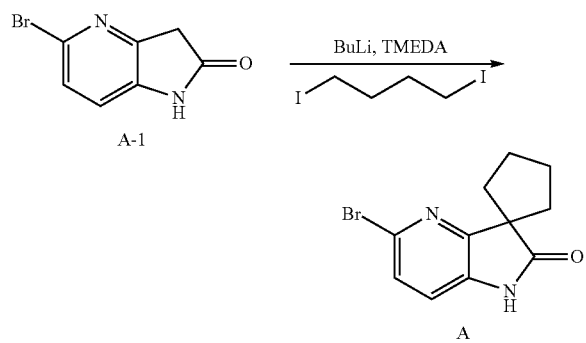

n-BuLi (2.5 M in hexane, 3.9 mL, 9.86 mmol) is added dropwise to a mixture of compound A-1 (1 g, 4.69 mmol) and TMEDA (1.09 gram, 9.39 mmol) in THF (25 mL) at −78° C. The mixture is stirred at −78° C. for 1 h, then diiodobutane (3.08 mL, 23.47 mmol) is added dropwise over 5 min. The resulting mixture is warmed to −20° C. over a 1 h period, and stirred for an additional 1 h at this temperature and then warmed up to room temperature. After stifling at room temperature for 3 h, the reaction is quenched with saturated NH$_4$Cl (10 mL). The resulting mixture is extracted with EtOAc (20 mL). Phases are separated, and organic layer is washed with water (10 mL) and brine (10 mL). Organic layer is seperated and dried over anhydrous Na$_2$SO$_4$, filtered and concentrated. The residue is purified on SiO$_2$ (using a solvent gradient from 3% EtOAc in Heptane to 40% EtOAc in Heptane) to yield Intermediate A. MS (ES+): m/z 267.3, 269.3[M+H]$^+$.

The following intermediates were prepared in a similar manner

| Structure | Intermediate | HPLC Method | m/z[M + H]$^+$ |
|---|---|---|---|
| 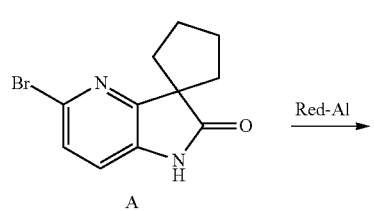 | B | A | 223.8 |
| 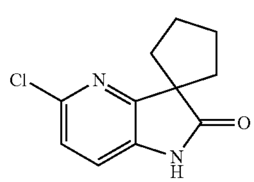 [SMILES: O=C1Nc2ccc(Cl)nc2C12CCCC2] | C | A | 223.4 |

Method 2
Synthesis of Intermediate D

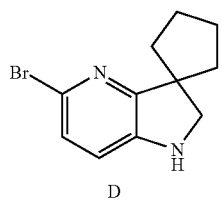

To a solution of intermediate A (6.3 g, 23.6 mmol) in toluene (200 mL) is added Red-Al (65 wt % in Toluene, 18.4 g, 59.0 mmol) dropwise. The resulting solution is stirred at room temperature for 1 h, then cooled down to 0° C. The reaction is carefully quenched with water (50 mL) and diluted with EtOAc (200 mL), and then treated with saturated aqueous Potassium Sodium Tartrate (50 mL). The layers is separated and the aqueous phase was extracted with EtOAc (2×10 mL). The combined organics are dried over anhydrous MgSO$_4$, filtered and concentrated. The residue is purified on SiO$_2$ (using a solvent gradient from 5% EtOAc in Heptane to 40% EtOAc in Heptane) to afford intermediate D. MS (ES+): m/z 254.2 [M+H]$^+$.

The following intermediates were prepared in a similar manner

| Structure | Intermediate | HPLC Method | m/z[M + H]$^+$ |
|---|---|---|---|
| 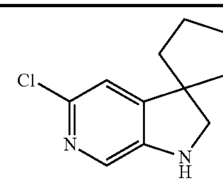 | E | A | 209.0 |
| 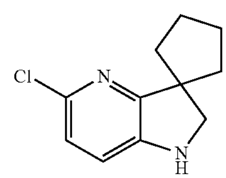 [SMILES: Clc1ccc2c(n1)C1(CCCC1)CN2] | F | A | 208.9 |

Method 3
Synthesis of Intermediate G

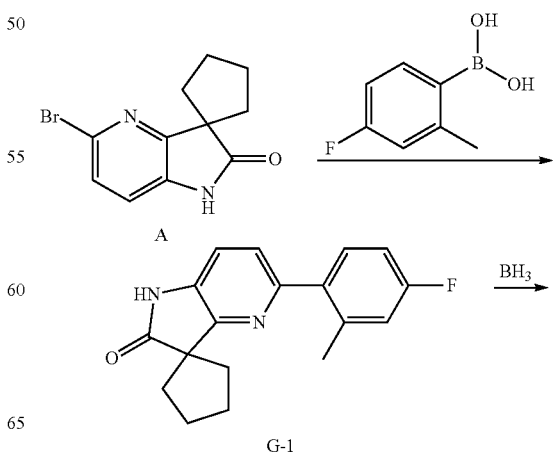

-continued

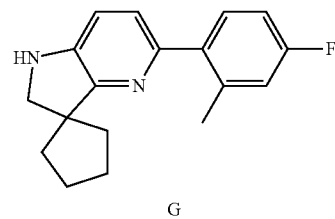

G

To a solution of A (359 mg, 1.34 mmol), and (4-fluoro-2-methyl-phenyl)boronic acid (310 mg, 2.02 mmol) in DMF (10 mL) is added a aqeous solution Na$_2$CO$_3$ (2M, 2.69 mL, 5.38 mmol). The mixture is sparged with Ar for 5 min. Dichloropalladium 4-ditert-butylphosphanyl-N,N-dimethyl-aniline (95 mg, 0.13 mmol) is then added and the resulting mixture is heated to 120° C. for 20 minutes in a Biotage microwave reactor. The mixture is cooled down, diluted with water (10 mL) and extracted with EtOAc (2×20 mL). Phases are separated, and the aqueous layer is extracted with EtOAc (20 mL). The combined organic layers are washed with brine (10 mL), dried over Na$_2$SO$_4$, filtered and concentrated. The residue is purified on SiO$_2$ (using a solvent gradient from 10% EtOAc in Heptane to 50% EtOAc in Heptane) to yield G-1.

A mixture of compound G-1 (435 mg, 1.47 mmol) and BH$_3$ (1M solution in THF, 29 mL, 29.36 mmol) is stirred at room temperature for 16 h. The resulting mixture is cooled to 0° C., and carefully diluted with MeOH (3 mL), followed by addition of HCl (12M, 0.8 mL). The resulting mixture is stirred at room temperature for 1 h. pH is adjusted to 8-9 with 10% aqueous NaOH, and then extracted with EtOAc (3×20 mL). The combined organic layers are washed with brine (20 mL), dried over anhydrous Na$_2$SO$_4$, filtered and concentrated. The residue is purified on SiO$_2$ (using a solvent gradient from 3% EtOAc in Heptane to 50% EtOAc in Heptane) to yield G. MS (ES+): m/z 282.9 [M+H]$^+$.

The following intermediates were prepared in a similar manner:

| Structure | Intermediate | HPLC Method | m/z [M + H]$^+$ |
|---|---|---|---|
| 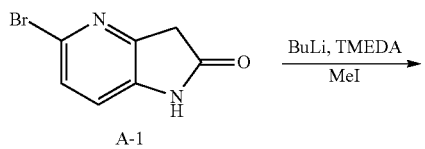 | H | A | 283.76 |

Method 4
Synthesis of Intermediate I

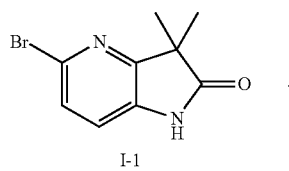

A-1

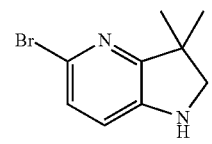

I-1

I n-BuLi (2.5 M in hexane, 15 mL, 37.55 mmol) is added dropwise to a a mixture of of A-1 (2 g, 9.39 mmol) and TMEDA (4.36 g, 37.55 mmol) in THF (90 mL) at −78° C. The mixture is stirred at −78° C. for 1 h, then iodomethane (5.33 g, 37.55 mmol) is added dropwise over 5 min. The mixture is warmed to room temperature and stirred for 4 h. The reaction is quenched with saturated aqueous NH$_4$Cl (20 mL). The resulting mixture is extracted with EtOAc (80 mL). Phases are separated, and the organic layer is washed with water (20 mL) and brine (20 mL). The organic layer is seperated and dried over anhydrous Na$_2$SO$_4$, filtered and concentrated. The residue is purified on SiO$_2$ (using a solvent gradient from 8% EtOAc in Heptane to 80% EtOAc in Heptane) to yield intermediate I-1.

To a solution of I-1 (200 mg. 0.83 mmol) in toluene (8 mL) is added Red-Al (65 wt % in Toluene, 1.03 mL, 3.32 mmol) dropwise. The resulting mixture is stirred at room temperature for 1 h, then cooledto 0° C. The reaction is carefully quenched with water (1 mL) and diluted with EtOAc (10 mL), treated with saturated aqueous Potassium Sodium Tartrate (10 mL). Phases are separated, and the organic layer is dried over anhydrous Na$_2$SO$_4$, filtered and concentrated. The residue is purified on SiO$_2$ (using a solvent gradient from 5% EtOAc in Heptane to 40% EtOAc in Heptane) to yield intermediate I. MS (ES+): m/z 227.3, 229.4 [M+H]$^+$.

The following intermediates were prepared in a similar manner

| Structure | Intermediate | HPLC Method | m/z[M + H]$^+$ |
|---|---|---|---|
| 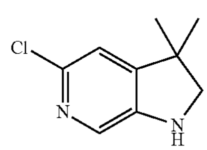 | J | A | 183.2 |
| 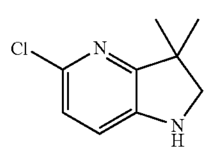 | K | A | 184.9 |

Method 5
Synthesis of Intermediate L

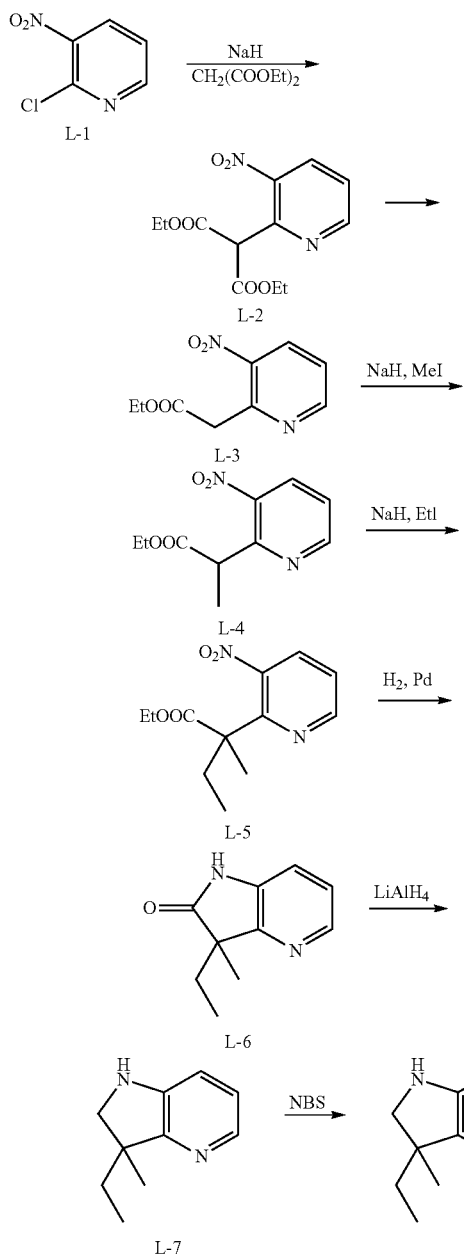

To a solution of CH$_2$(CO$_2$EO$_2$ (109 g, 0.69 mol) in THF (800 mL) is added NaH (60%, 17.8 g, 0.45 mol) at 0° C. The mixture is allowed to warm to room temperature and stirred for 1 h. Intermediate L-1 (47 g, 0.3 mol) is then added to the mixture and the mixture is heated to 60° C. for 5 h. The reaction mixture is poured into water (200 mL) and extracted with EtOAc (1 L). The organic layer is washed with brine (100 mL), dried over Na$_2$SO$_4$, filtered and concentrated. The residue is purified on SiO$_2$ (25% EtOAc in Heptane) to yield intermediate L-2.

A mixture of L-2 (40 g, 0.14 mol) in DMSO (200 mL) and water (20 mL) is heated to 120° C. for 8 h under N$_2$. The mixture is poured into water (50 mL) and extracted with EtOAc (500 mL). The organic layer is washed with brine (50 mL), dried over Na$_2$SO$_4$, filtered and concentrated. The residue is purified on SiO$_2$ (25% EtOAc in Heptane) to yield intermediate L-3.

To a solution of L-3 (17.8 g, 85 mmol) in DMF (120 mL) is added NaH (60%, 3.7 g, 94 mmol) at 0° C. under N$_2$. The mixture is stirred for 0.5 h after addition and then MeI (12 g, 85 mmol) in DMF (10 mL) is added dropwise at 0° C. under N$_2$. The reaction mixture is allowed to warm to room temperature and stirred for another 2 h. The mixture is poured into water (50 mL), extracted with EtOAc (500 mL). The organic layer is washed with brine (50 mL), dried over Na$_2$SO$_4$, filtered and concentrated. The residue is purified on SiO$_2$ (20% EtOAc in Heptane) to yield intermediate L-4.

To a solution of L-4 (5.7 g, 25 mmol) in DMF (40 mL) is added NaH (60%, 2 g, 50 mmol) at 0° C. under N$_2$. The mixture is stirred for 0.5 h and then EtI (7.8 g, 50 mmol) in DMF (5 mL) is added dropwise at 0° C. under N$_2$. The reaction mixture is allowed to warm to room temperature and stirred for another 2 h. The mixture was poured into water (40 mL), extracted with EtOAc (200 mL). The organic layer is washed with brine (40 mL), dried over Na$_2$SO$_4$, filtered and concentrated. The residue is purified on SiO$_2$ (15% EtOAc in Heptane) to yield intermediate L-5.

A mixture of L-5 (4.2 g, 17 mmol) and Pd/C (10%, 0.6 g) in EtOH (80 mL) is heated to 50° C. under H$_2$ at a pressure of 50 psi for 8 h. After filtration, the filtrate is concentrated. The residue is purified on SiO$_2$ to yield intermediate L-6.

To a solution of L-6 (2.1 g, 12 mmol) in THF (50 mL) is added LiAlH$_4$ (0.91 g, 24 mmol) at 0° C. under N$_2$. The reaction mixture is heated to 50° C. after addition and stirred for 5 h. The reaction mixture is quenched by water (10 mL), filtrated and the precipitate is washed with MeOH for 3 times. The combined organic layers are concentrated and the residue is purified on SiO$_2$ to yield intermediate L-7.

To a solution of L-7 (1.4 g, 8.6 mmol) in CH$_3$CN (25 mL) is added NBS (1.52 g, 8.6 mmol) and the mixture is stirred for 1.5 h at room temperature. The mixture is diluted with water (10 mL) and extracted with EtOAc (50 mL). The organic layer is concentrated. The residue is purified on SiO$_2$ (15% EtOAc in Heptane) to yield intermediate L. MS (ES+): m/z 241.0 [M+H]$^+$.

Method 6
Synthesis of Intermediate M

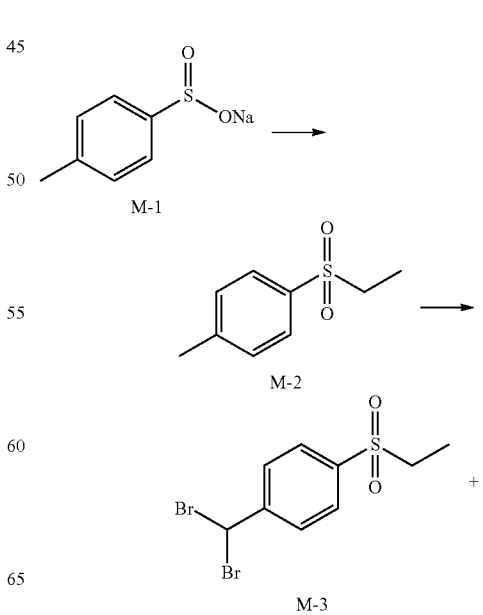

-continued

M-4: diethyl phosphite (O=P(H)(OEt)₂)

M-5: 4-(bromomethyl)phenyl ethyl sulfone

M-6: 4-(aminomethyl)phenyl ethyl sulfone

M: 4-(aminomethyl)phenyl ethyl sulfone hydrochloride (ClH H₂N-)

A mixture of intermediate M-1 (100 g, 561 mmol), EtI (131 g, 842 mmol) and Tetra-n-butylammonium bromide (18 g, 56 mmol) in H₂O (200 mL), acetone (150 mL) and of toluene (150 mL) is stirred in sealed vessel at 80° C. overnight. The mixture is partitioned between H₂O and EtOAc. The organic layer is dried and concentrated. The residue is purified by silica gel column (Petroleum ether: EtOAc=20:1) to afford intermediate M-2.

A mixture of compound M-2 (200 g, 1.09 mol), NBS (425.02 g, 2.39 mol) and AIBN (17.82 g, 108.54 mmol) in CCl₄ (1400 mL) is stirred at reflux overnight. The mixture is partitioned between H₂O and CH₂Cl₂. The organic layer is dried over Na₂SO₄ and evaporated to afford intermediate M-3.

To a solution of intermediate M-3 (333 g, 974 mmol) and DIEA (129 g, 1 mol) in CH₃CN (500 mL) is added M-4 (138 g, 1 mol) in CH₃CN (150 mL) dropwise at 0° C., then the mixture is then stirred for 5 h. The reaction mixture is concentrated. The residue is recrystallized from MeOH to afford intermediate M-5.

A solution of intermediate M-5 (50 g, 190 mmol) in MeOH (200 mL) is added into a solution of NH₃/MeOH (800 mL) at −78° C. The reaction mixture is stirred at r.t overnight. The reaction mixture is concentrated. The residue is re-crystallized from EtOAc to afford intermediate M-6.

A solution of intermediate M-6 (50 g, 250.9 mmol) in HCl/MeOH (250 mL) is stirred at rt overnight. The reaction mixture is concentrated to afford M as a HCl salt Method 7
Synthesis of Intermediate N

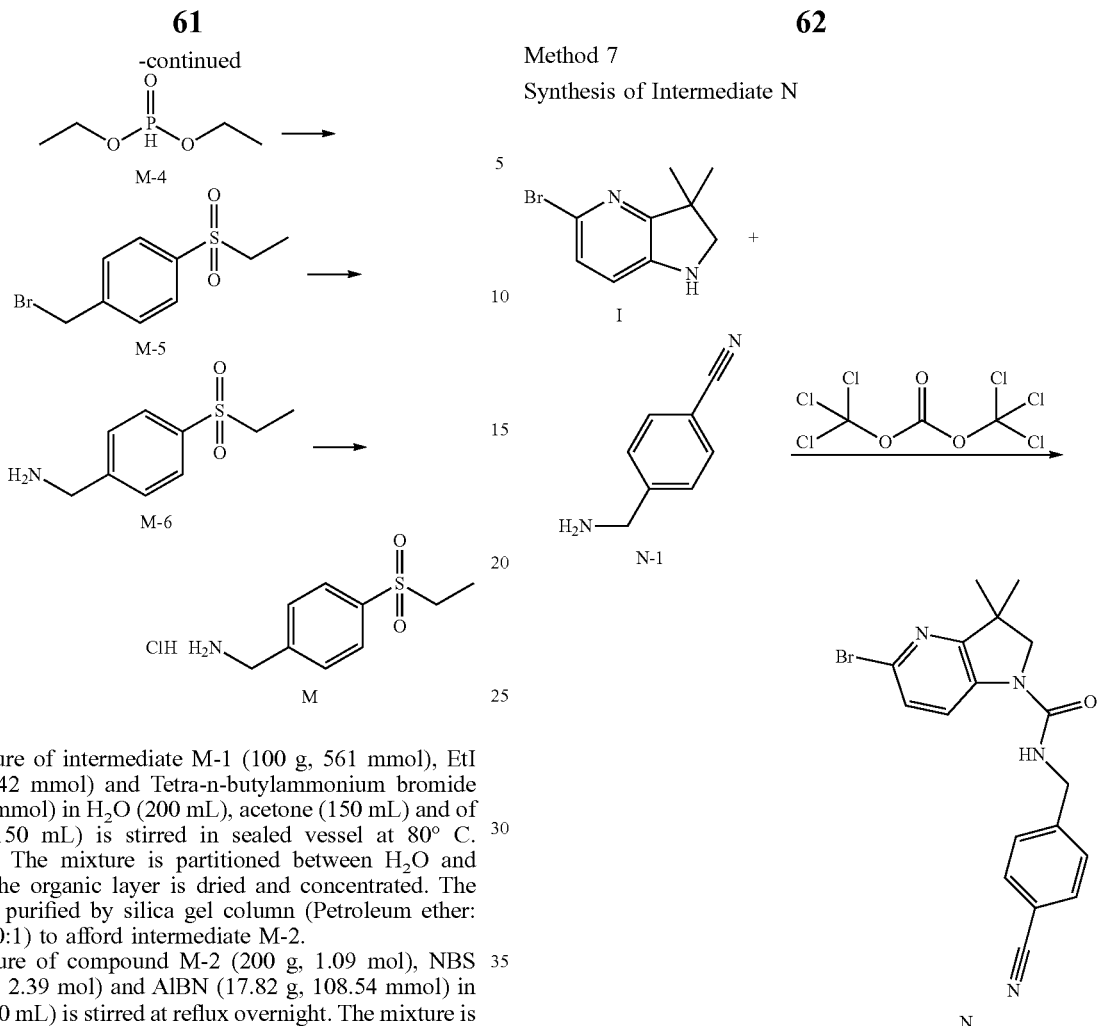

To a solution of triphosgene (56 mg, 0.19 mmol) in CH₂Cl₂ (2 mL) at 0° C. is slowly added a solution of I (108 mg, 0.48 mmol) and DIEADIEA (0.17 mL, 0.95 mmol) in CH₂Cl₂ (2 mL). The resulting mixture is stirred at 0° C. for 15 min, and then a solution of N-1 (126 mg, 0.95 mmol) and DIEADIEA (0.17 mL, 0.95 mmol) in DMF (1 mL) is added dropwise. the mixture is stirred at 0° C. for 5 min and then allowed to warm up to room temperature for 1 h. The reaction is diluted with MeOH (1 mL) and concentrated. The residue is purified on SiO₂ (using a solvent gradient from 0% MeOH in CH₂Cl₂ to 2% MeOH in CH₂Cl₂) to yield intermediate N. MS (ES+): m/z 386.8 [M+H]⁺.

The following intermediates were prepared in a similar manner

| Structure | Intermediate/Example | HPLC Method | m/z[M + H]⁺ |
|---|---|---|---|
| (Br-pyridine-spirocyclopentane-pyrrolidine urea with 4-(ethylsulfonyl)benzyl) | O | A | 282.9, 284.8 |

-continued
| Structure | Intermediate/Example | HPLC Method | m/z[M + H]+ |
|---|---|---|---|
| 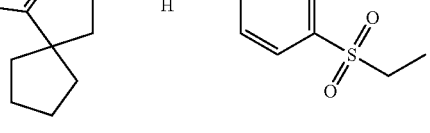 | P | A | 434.6 |
| 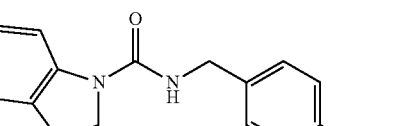 | Q | A | 411.9 |
| 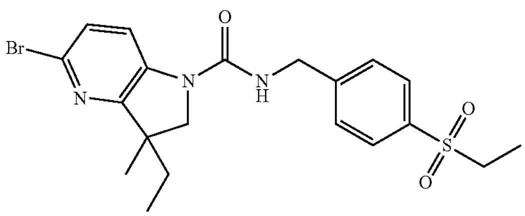 [SMILES: CCC1(C)CN(C(=O)NCc2ccc(S(=O)(=O)CC)cc2)c2ccc(Br)nc21] | R | A | N/A |
| 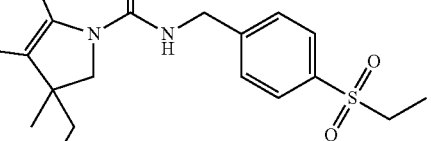 | 16 | C | 438.9 |
| 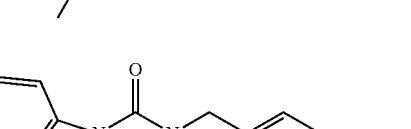 | 17 | C | 453.9 |
| 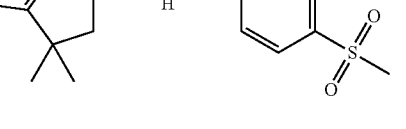 | S | A | 394.2 |
| 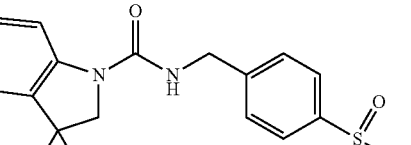 | T | A | 408.0 |

| Structure | Intermediate/Example | HPLC Method | m/z[M + H]+ |
|---|---|---|---|
| 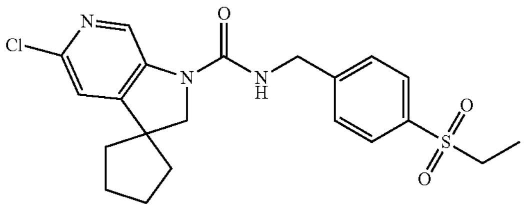 [SMILES: CCS(=O)(=O)c1ccc(CNC(=O)N2CC3(CCCC3)c3cc(Cl)ncc32)cc1] | 96 | C | 434.2 |

Method 8

Synthesis of Intermediate U

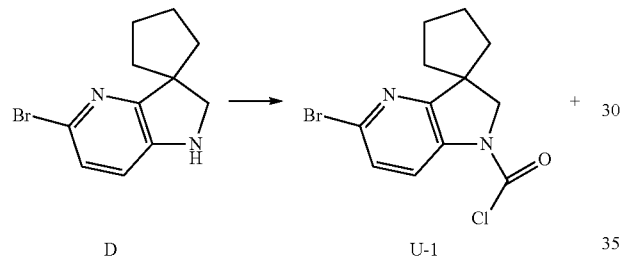

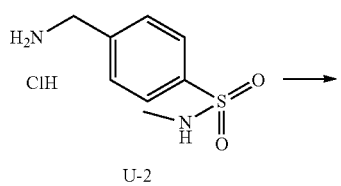

To a stirred solution of D (500 mg, 1.97 mmol) in CH$_2$Cl$_2$ (20 ml) was added saturated aqueous NaHCO3 (20 ml) followed by phosgen (15 wt % in Toluene, 3.5 mL, 4.94 mmol). The reaction is stirred at room temperature for 45 min. The layers are separated and the aqueous phase is extracted once with CH$_2$Cl$_2$ (20 mL). The combined organics are dried over MgSO$_4$, filtered and concentrated. The crude U-1 is used without further purification.

To U-2 (512 mg, 2.16 mmol) is added a solution of U-1 (620 mg, 1.97 mmol) in dimethylacetamide (20 mL) followed by DIEA (1.41 mL, 7.86 mmol). The reaction is stirred at room temperature for 1 h. The reaction is poured into water and EtOAc. The layers are separated and the aqueous phase is extracted with EtOAc (2×20 mL). The combined organics are dried over MgSO$_4$, filtered and concentrated. The residue is purified on SiO$_2$ (using a solvent gradient from 0% MeOH in CH$_2$Cl$_2$ to 5% MeOH in CH$_2$Cl$_2$) to yield intermediate U. MS (ES+): m/z 481.5 [M+H]$^+$.

The following intermediates were prepared in a similar manner

| Structure | Intermediate/Example | HPLC Method | m/z[M + H]+ |
|---|---|---|---|
| 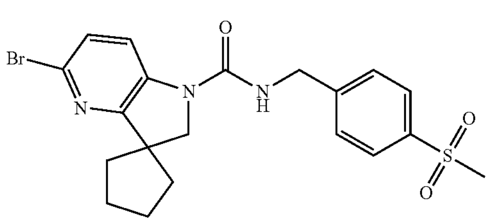 [SMILES: CS(=O)(=O)c1ccc(CNC(=O)N2CC3(CCCC3)c3nc(Cl)ccc32)cc1] | V | A | 466.5 |

| Structure | Intermediate/Example | HPLC Method | m/z[M + H]+ |
|---|---|---|---|
| (structure) | 62 | A | 420.5 |

Method 9
Synthesis of Intermediate W

Method 10
Synthesis of Intermediate AA

To a solution of W-1 (300 mg, 1.29 mmol) in anhydrous MeOH (15 mL) is added NaOMe (208 mg, 3.86 mmol). The mixture is stirred at room temperature for 1 h. The solution is filtered and concentrated. The residue is purified on SiO$_2$ (using a solvent gradient from 5% EtOAc in Heptane to 30% EtOAc in Heptane) to intermediate W. MS (ES+): m/z 230.8 [M+H]+.

The following intermediates were prepared in a similar manner

| Structure | Intermediate | HPLC Method | m/z [M + H]+ |
|---|---|---|---|
| (structure) | X | A | 258.9 |
| (structure) | Y | A | 244.5 |
| (structure) | Z | A | 258.9 |

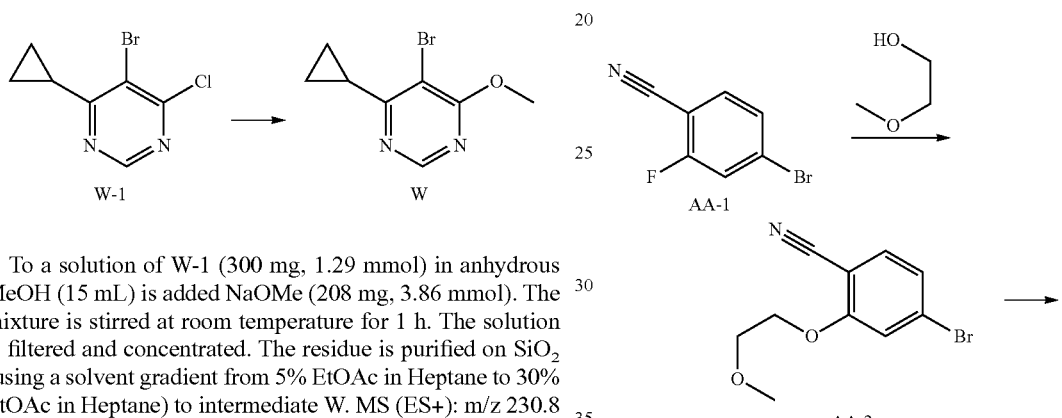

A mixture of AA-1 (1.5 g, 7.50 mmol), 2-methoxyethanol (5.71 g, 75.00 mmol) and potassium carbonate (1.55 g, 11.25 mmol) in DMF (35 mL) is stirred at room temperature for 12 h. The reaction mixture is diluted with water (20 mL) and EtOAc (50 mL). The layers are separated and the aqueous phase is extracted with EtOAc (2×50 mL).

The combined organics are washed with brine (20 mL), the organic layer is separated, dried over MgSO$_4$, filtered and concentrated to yield intermediate AA-2. The residue is used without further purification.

A mixture of AA-2 (1.2 g, 4.69 mmol) and BH$_3$ (1M solution in THF, 14.06 mL, 14.06 mmol) is stirred at 80° C. for 16 h. The reaction mixture is carefully quenched with MeOH, and concentrated. The crude is purified by reverse phase prep HPLC eluting with 10-100% CH$_3$CN in water (+0.1% TFA). The concentrated solid was basified by PL-HCO$_3$ MP column to yield title Intermediate AA. MS (ES+): m/z 261.9 [M+H]+.

Method 11
Synthesis of Intermediate AB

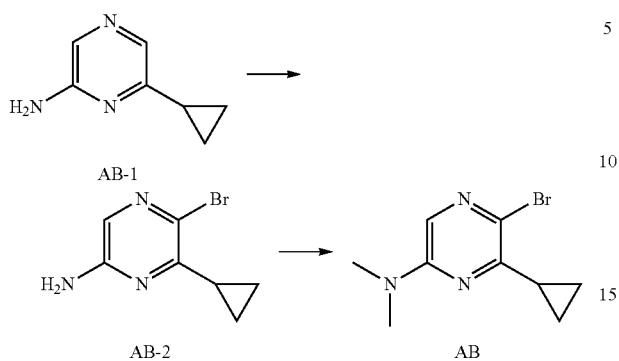

To a solution of AB-1 (4 g, 29.59 mmol) in CH₃CN (150 mL) was added NBS (5.27 g, 29.59 mmol) at room temperature. After 0.5 h, the reaction mixture is concentrated. The residue is purified on SiO$_2$ (using a solvent gradient from 5% EtOAc in Heptane to 30% EtOAc in Heptane) to intermediate AB-2.

To a solution of AB-2 (500 mg, 2.34 mmol) in DMF (10 mL) is added NaH (60%, oil dispersion, 234 mg, 5.84 mmol). After 15 minutes, the iodomethane (829 mg, 5.84 mmol) is added and the reaction is stirred at room temperature for 2 h. The mixture is poured into water (10 mL) and the precipitated product is collected via filtration, the dried in vacuum oven at 50° C. for 18 h to yield intermediate AB. MS (ES+): m/z 243.9 [M+H]⁺.

Method 12
Synthesis of Intermediate AC

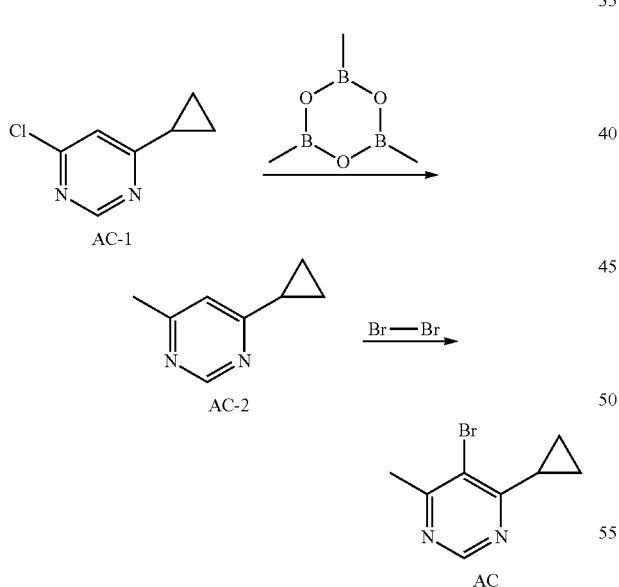

To a solution of AC-1 (320 mg, 2.07 mmol), 2,4,6-trimethyl-1,3,5,2,4,6-trioxatriborane (520 mg, 4.14 mmol), and aqueous Na$_2$CO$_3$ (2M, 3.1 mL, 6.21 mmol) in dioxane (10 mL) is added catalyst dichloropalladium 4-ditert-butyl-phosphanyl-N,N-dimethyl-aniline (73 mg, 0.10 mmol). The resulting mixture is heated to 130° C. for 40 minutes in a Biotage microwave. The mixture is diluted with MeOH (5 mL), filtered and concentrated. The residue is purified on SiO$_2$ (using a solvent gradient from 10% EtOAc in Heptane to 40% EtOAc in Heptane) to yield intermediate AC-2.

To a solution g of AC-2 (363 mg, 2.71 mmol) in EtOH (10 mL) is added bromine (432 mg, 3.71 mmol) −10° C. The reaction mixture is stirred at room temperature for 18 h. The resulting solution is concentrated. The residue is purified on SiO$_2$ (using a solvent gradient from 0% EtOAc in Heptane to 20% EtOAc in Heptane) to yield intermediate AC. MS (ES+): m/z 214.4 [M+H]⁺.

Method 13
Synthesis of Intermediate AD

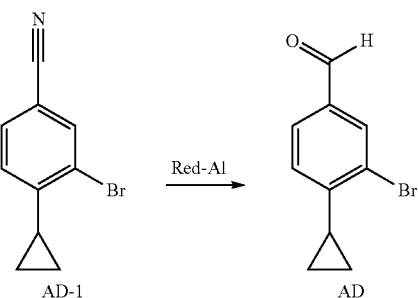

To a chilled (0° C.) solution of AD-1 (222 mg, 1 mmol) in THF (10 mL) under Ar is DIBAL (1M in toluene, 2 mL, 2 mmol). After 3 h, the reaction is quenched with MeOH (2 mL) and concentrated. The residue is taken up in MeOH, poured into water and CH$_2$Cl$_2$. The phases are seperated and the organic layer is concentrated to yield intermediate AD which is used without further purification.

Method 14

Synthesis of Example 1

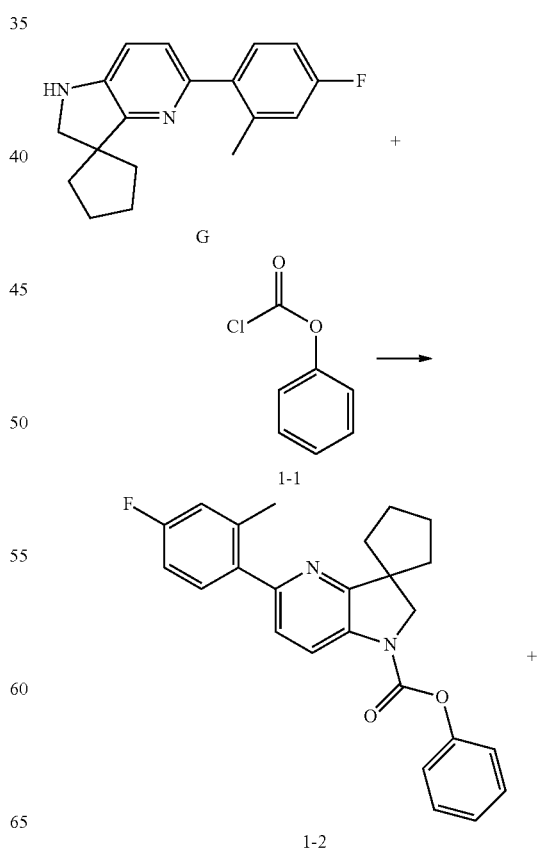

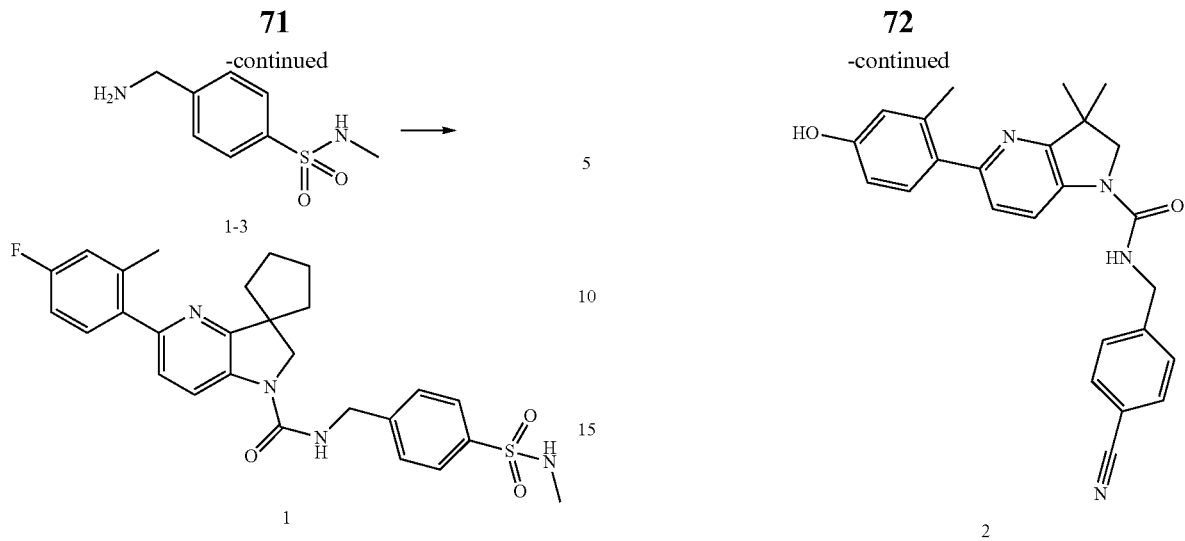

To a solution of G (227 mg, 0.80 mmol) in THF (8 mL) is added NaHMDS (1M in THF, 1.61 mL, 1.61 mmol). 1-1 (0.22 mL, 1.77 mmol) is then added. The resulting mixture is stirred at 60° C. for 20 min. The reaction mixture is diluted with water (3 mL) and extracted with $CH_2Cl_2$ (10 mL). The phases are separated and the organics are concentrated to yield 1-2.

To a solution of compound 1-2 (85 mg, 0.21 mmol) in DMF (2 mL) is added 1-3 (127 mg, 0.63 mmol) and DIEA (0.22 mL, 1.27 mmol). The mixture is heated to 160° C. for 3 h in a Biotage microwave reactor. The mixture is concentrated and purified by reverse phase prep HPLC eluting with 30-100% $CH_3CN$ in water (+0.1% TFA). The concentrated solid was basified by PL-$HCO_3$ MP column to yield title compound 1. MS (ES+): m/z 509.3 $[M+H]^+$.

The following compounds were prepared in a similar manner:
Example 86
Method 15

Synthesis of Example 2

To a solution of N (60 mg, 0.16 mmol), 2-1 (35 mg, 0.23 mmol) and aqueous $Na_2CO_3$ (2M, 0.3 mL, 0.62 mmol) in DMF (2 mL) is added catalyst dichloropalladium 4-ditert-butylphosphanyl-N,N-dimethyl-aniline (11 mg, 0.016 mmol). The resulting mixture is heated to 120° C. for 30 minutes in a Biotage microwave. The mixture is diluted with MeOH (5 mL), filtered and concentrated. The crude was purified by reverse phase prep HPLC eluting with 10-100% $CH_3CN$ in water (+0.1% TFA). The concentrated solid was basified by PL-$HCO_3$ MP column to yield title compound 2. MS (ES+): m/z 412.2 $[M+H]^+$.

The following compounds were prepared in a similar manner:
Example 3-5, 18-24, 42-47, 50-58, 62, 87-93
Method 16

Synthesis of Example 6

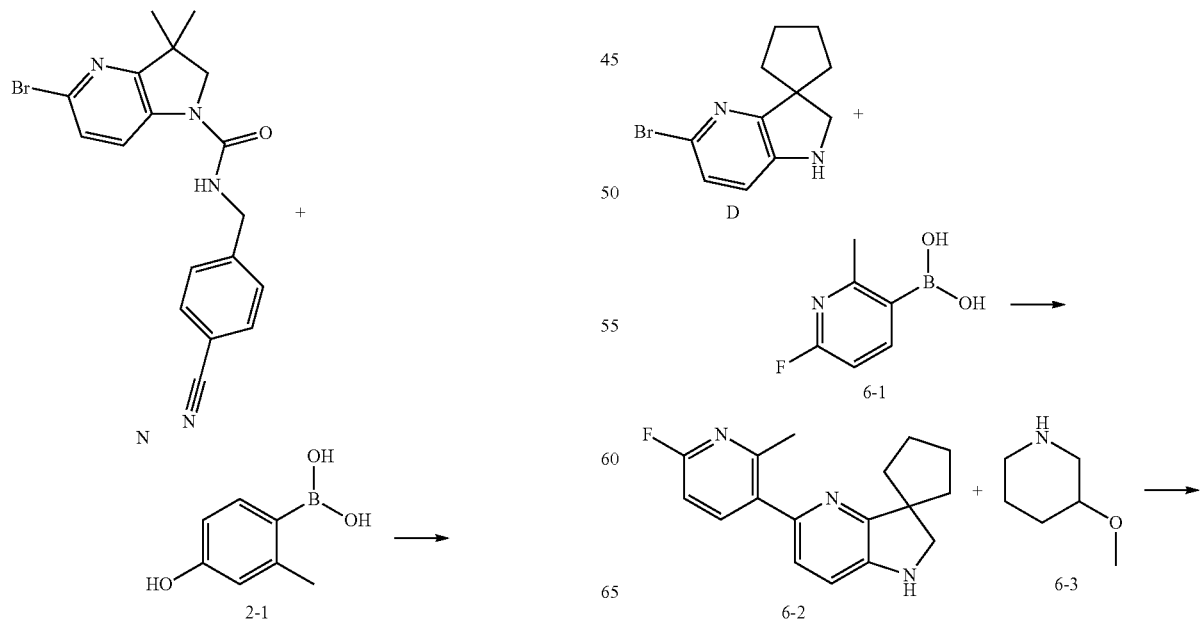

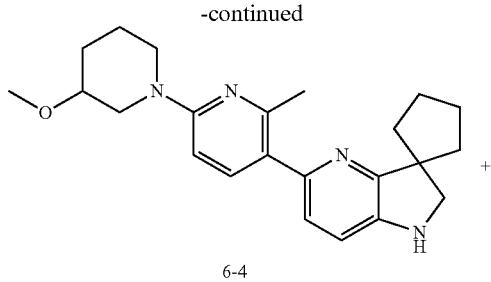

6-4

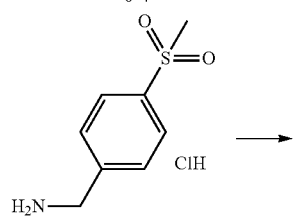

6-5

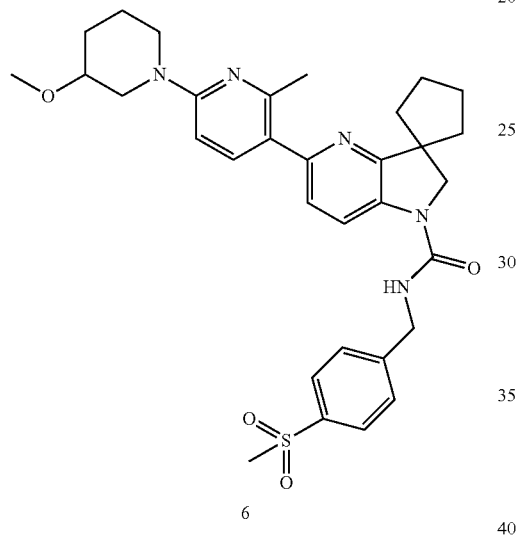

6

To a solution of intermediate D (500 mg, 1.98 mmol), 6-1 (459 mg, 2.96 mmol) and aqueous Na$_2$CO$_3$ (2M, 3.95 mL, 7.90 mmol) in DMF (15 mL) is added catalyst dichloropalladium 4-ditert-butylphosphanyl-N,N-dimethyl-aniline (14 mg, 0.019 mmol). The resulting mixture is heated to 120° C. for 30 minutes in a Biotage microwave. The mixture is diluted with MeOH (5 mL), filtered and concentrated. The residue is purified on SiO$_2$ (using a solvent gradient from 10% EtOAc in Heptane to 50% EtOAc in Heptane) to yield 6-2.

A mixture of 6-2 (100 mg, 0.35 mmol), 6-3 (406 mg, 3.53 mmol) and pyridine (3 mL) is heated to 160° C. for 5 h in a Biotage microwave reactor. The resulting solution is concentrated. The crude is purified by reverse phase prep HPLC eluting with 10-100% CH$_3$CN in water (+0.1% TFA). The concentrated solid was basified by PL-HCO$_3$ MP column to yield 6-4.

To a solution of triphosgene (27 mg, 0.09 mmol) in CH$_2$Cl$_2$ (1 mL) at 0° C. is slowly added a solution of 6-4 (87 mg, 0.23 mmol) and DIEA (0.12 mL, 0.70 mmol) in CH$_2$Cl$_2$ (2 mL). The resulting mixture is stirred at 0° C. for 15 min, and then a solution of 6-5 (102 mg, 0.46 mmol) and DIEA (0.12 mL, 0.70 mmol) in DMF (1 mL) is added dropwise. The mixture is stirred at 0° C. for 5 min and then allowed to warm up to room temperature for 1 h. The reaction is diluted with MeOH (1 mL), and concentrated. The crude is purified by reverse phase prep HPLC eluting with 10-100% CH$_3$CN in water (+0.1% TFA). The concentrated solid was basified by PL-HCO$_3$ MP column to yield compound 6. MS (ES+): m/z 590.4 [M+H]$^+$.

The following compounds were prepared in a similar manner:

Example 7

Method 17

Synthesis of Example 8

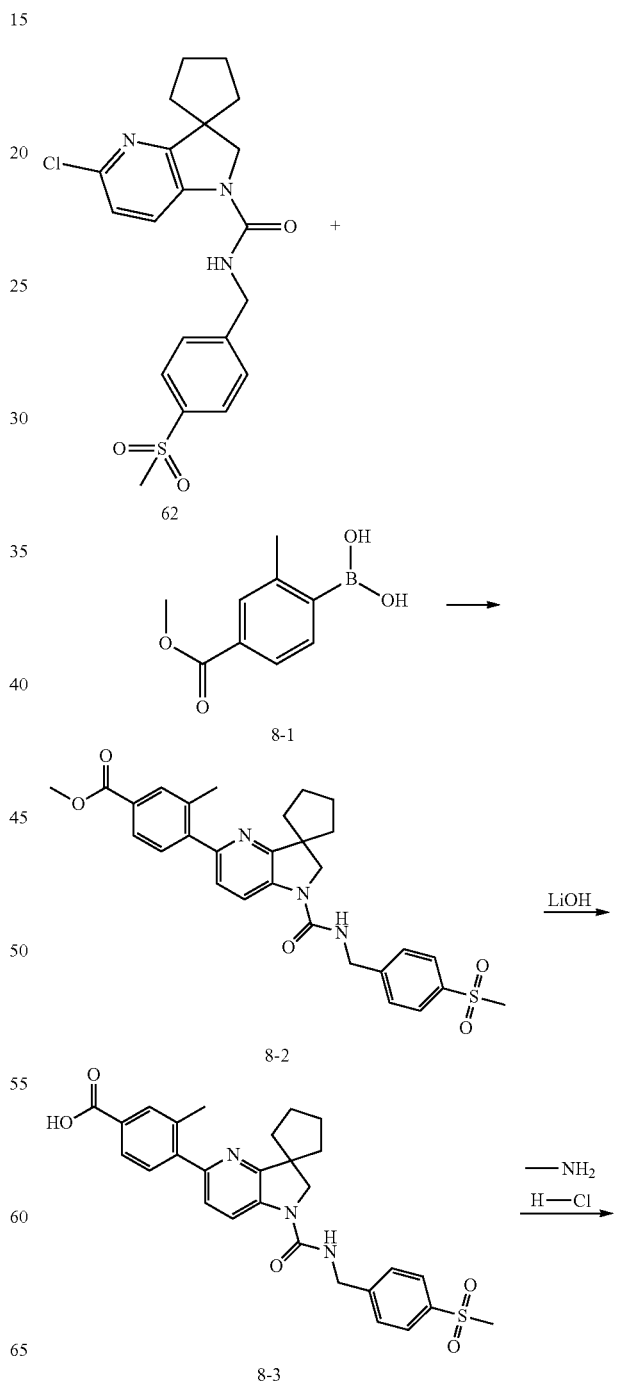

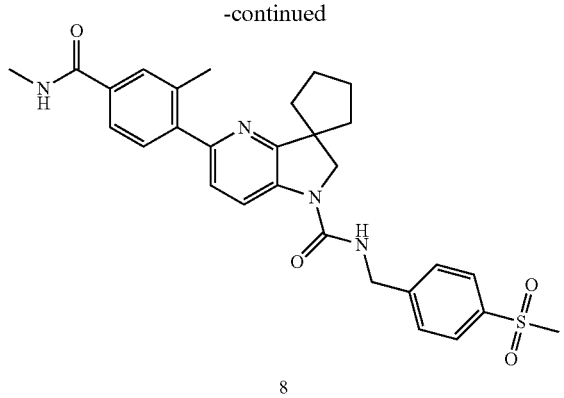

8

To a solution of Example 62 (350 mg, 0.83 mmol), 8-1 (323 mg, 1.67 mmol) and aqueous Na$_2$CO$_3$ (2M, 1.67 mL, 3.33 mmol) in DMF (8 mL) is added catalyst dichloropalladium 4-ditert-butylphosphanyl-N,N-dimethyl-aniline (59 mg, 0.08 mmol). The vial was sealed and heated to 100° C. for 17 h. The reaction was cooled and poured into water (5 mL) and EtOAc (20 mL). The layers are separated and the aqueous phase is extracted with EtOAc (2×20 mL). The combined organics are dried over MgSO$_4$, filtered and concentrated. The residue is purified on SiO$_2$ (using a solvent gradient from 0% MeOH in CH$_2$Cl$_2$ to 5% MeOH in CH$_2$Cl$_2$) to yield 8-2.

To a solution of 8-2 (300 mg, 0.56 mmol) in 1,4-dioxane (10 mL) and water (2 mL) is added lithium hydroxide monohydrate (236 mg, 5.62 mmol). After stifling for 16 h at room temperature, the reaction mixture is treated with HOAc to pH-5 and the product is diluted with water (5 mL) and EtOAc (20 mL). The layers are separated and the aqueous phase is extracted with EtOAc (20 mL). The combined organics are dried over MgSO$_4$, filtered and concentrated to give 8-3 which is used without further purification.

To a solution of 8-3 (75 mg, 0.14 mmol) in DMF (4 mL) is added HATU (66 mg, 0.17 mmol) followed by methylamine hydrochloride (11 mg, 0.16 mmol) and DIEA (0.25 mL, 1.44 mmol). The resulting mixture is stirred at room temperature for 16 h and then poured into water (2 mL) and EtOAc (10 mL). The layers are separated and the aqueous phase is extracted with EtOAc (2×10 mL). The combined organics are dried over MgSO$_4$, filtered and concentrated. The residue is purified on SiO$_2$ (using a solvent gradient from 0% MeOH in CH$_2$Cl$_2$ to 4% MeOH in CH$_2$Cl$_2$) to yield compound 8. MS (ES+): m/z 533.3 [M+H]$^+$.

The following compounds were prepared in a similar manner:

Example 9
Method 18

Synthesis of Example 10

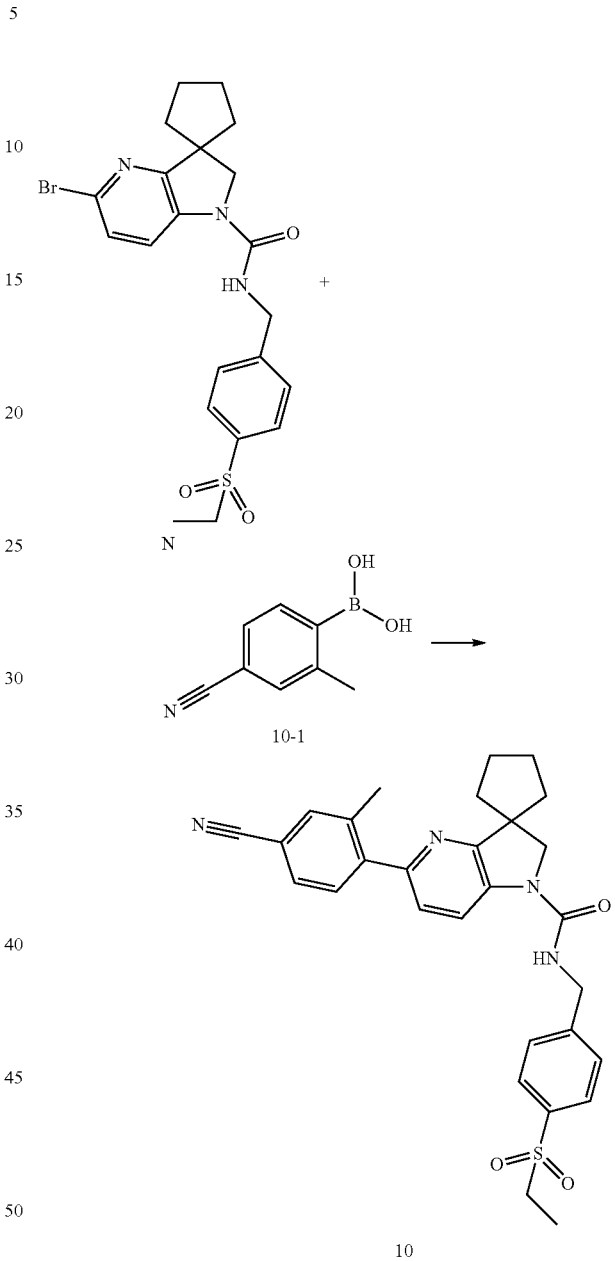

A solution of intermediate N (100 mg, 0.21 mmol), 10-1 (34 mg, 0.21 mmol) and aqueous Na$_2$CO$_3$ (2M, 0.5 mL, 1 mmol) in 1-propanol (2 mL) is bubbled with Ar for 5 min. Then Xphos (10 mg, 0.02 mmol) and catalyst palladium acetate (5 mg, 0.02 mmol) are added under AAr. The vial is sealed and heated to 100° C. for 2 h in microwave reactor. The reaction is cooled and diluted with MeOH (5 mL), filtered and concentrated. The crude is purified by reverse phase prep HPLC eluting with 10-100% CH$_3$CN in water (+0.1% TFA). The concentrated solid was basified by PL-HCO$_3$ MP column to yield title compound 10. MS (ES+): m/z 515.4 [M+H]$^+$.

The following compounds were prepared in a similar manner:

Example 11-15, 31-32, 36, 72

Method 19

Synthesis of Example 25

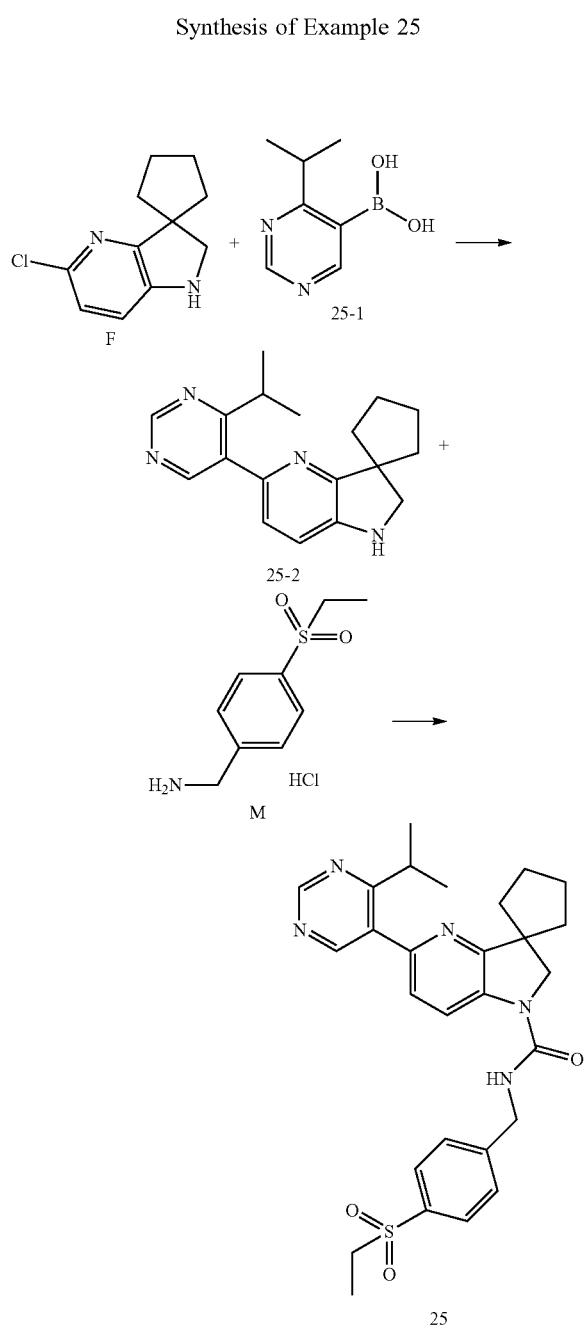

Intermediate 25-2 is synthesized from intermediate F according to Method 16 described for the synthesis of 6-2 from intermediate D.

The title product 25 is synthesized from 25-2 according to Method 7 described for the synthesis of Example 16 from intermediate I. MS (ES+): m/z 520.3 [M+H]+.

Method 20

Synthesis of Example 26

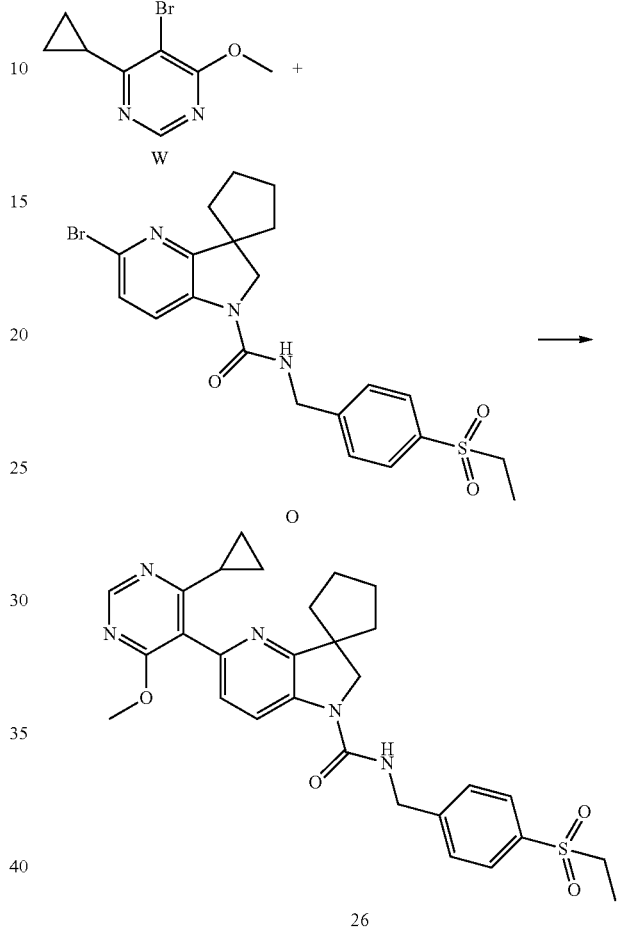

A solution of intermediate W (90 mg, 0.39 mmol), 4,4,5,5-tetramethyl-2-(4,4,5,5-tetramethyl-1,3,2-dioxaborolan-2-yl)-1,3,2-dioxaborolane (219 mg, 0.86 mmol) and KOAc (116 mmol, 1.18 mmol) in solvent (DME/water/Toluene/EtOH 10:1:6:3, 2 mL) is bubbled with Ar for 5 min. PdCl$_2$(dppf) CH$_2$Cl$_2$ (65 mg, 0.08 mmol) is added under ArAr. The resulting mixture is stirred at 90° C. for 30 min in a Biotage microwave reactor. To the cooled mixture is added O (150 mg, 0.31 mmol) and dichloropalladium 4-di-tert-butylphosphanyl-N,N-dimethyl-aniline (20 mg, 0.03 mmol). The DMF (1 mL) and aqueous Na$_2$CO$_3$ (2M, 0.3 mL) are added. The mixture is heated to 110° C. for 20 min in Biotage microwave reactor. The resulting mixture is diluted with MeOH (5 mL), filtered and concentrated. The crude is purified by reverse phase prep HPLC eluting with 10-100% CH$_3$CN in water (+0.1% TFA). The concentrated solid is basified by PL-HCO$_3$ MP column to yield title compound 26. MS (ES+): m/z 548.1 [M+H]+.

The following compounds were prepared in a similar manner:
Example 33, 35, 73, 77-78, 81, 94, 97
Method 21

Synthesis of Example 27

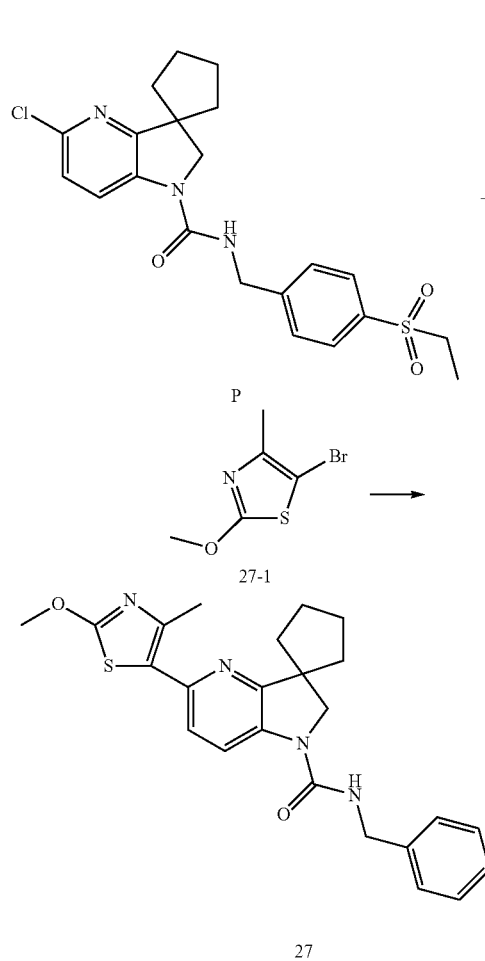

To a solution of intermediate P (125 mg, 0.28 mmol) and 4,4,5,5-tetramethyl-2-(4,4,5,5-tetramethyl-1,3,2-dioxaborolan-2-yl)-1,3,2-dioxaborolane (293 mg, 1.15 mmol) in 1,4-dioxane (1 mL) is added dichloropalladium 4-ditert-butylphosphanyl-N,N-dimethyl-aniline (20 mg, 0.03 mmol), followed by KOAc (113 mmol, 1.15 mmol). The resulting mixture is stirred at 110° C. for 10 min in a Biotage microwave reactor. To the cooled mixture is added 27-1 (60 mg, 0.21 mmol) and dichloropalladium 4-ditert-butylphosphanyl-N,N-dimethyl-aniline (30 mg, 0.04 mmol). DMF (1 mL) and aqueous $Na_2CO_3$ (2M, 0.3 mL) are added. The mixture is heated to 100° C. for 2 h in Biotage microwave reactor. The resulting misture is diluted with MeOH (5 mL), filtered and concentrated. The crude is purified by reverse phase prep HPLC eluting with 10-100% $CH_3CN$ in water (+0.1% TFA). The concentrated solid is basified by PL-$HCO_3$ MP column to yield title compound 27. MS (ES+): m/z 527.3 $[M+H]^+$.

The following compounds were prepared in a similar manner:
Example 32, 41
Method 22

Synthesis of Example 28

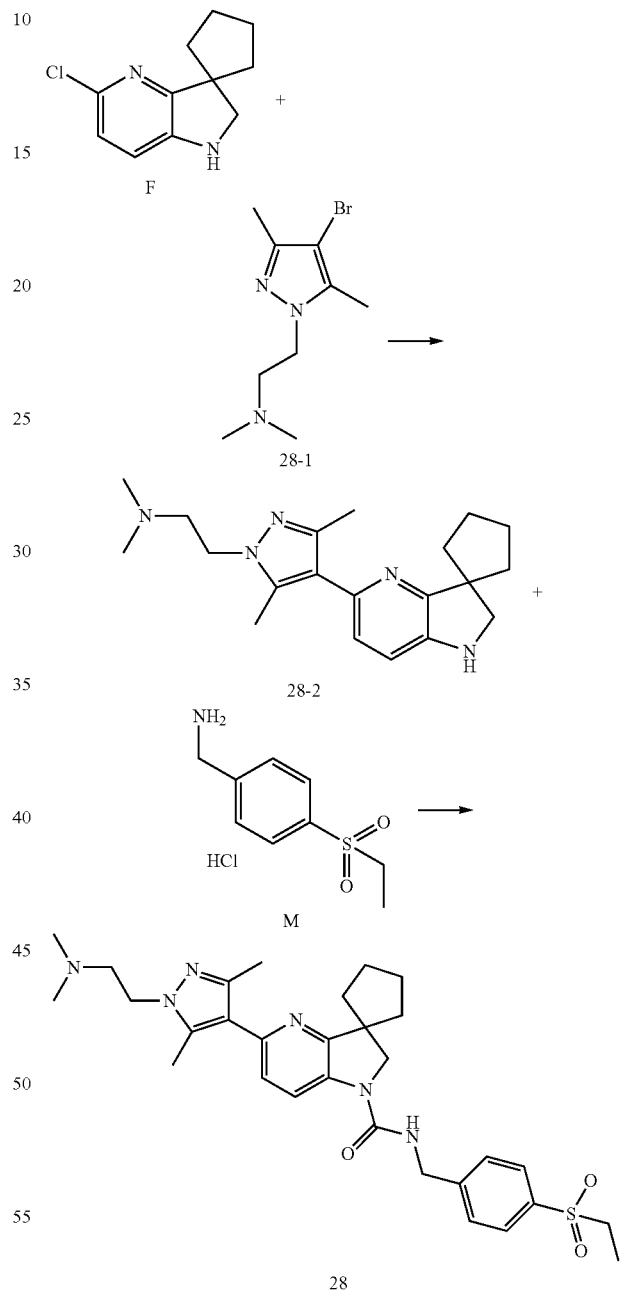

To a solution of intermediate F (200 mg, 1 mmol) and 4,4,5,5-tetramethyl-2-(4,4,5,5-tetramethyl-1,3,2-dioxaborolan-2-yl)-1,3,2-dioxaborolane (243 mg, 1mmol) in 1,4-dioxane (10 mL) is added dichloropalladium 4-ditert-butylphosphanyl-N,N-dimethyl-aniline (68 mg, 0.1 mmol), followed by KOAc (94 mmol, 1 mmol). The resulting mixture is stirred at 110° C. for 20 min in a Biotage microwave reactor. To the cooled mixture is added 28-1 (236 mg, 1 mmol) and dichloropalladium 4-ditert-butylphosphanyl-N,N-dimethyl-aniline (68 mg, 0.1 mmol). DMF (5 mL) and aqueous Na$_2$CO$_3$ (2M, 2 mL) are added. The mixture is heated to 110° C. for 20 min in Biotage microwave reactor. The resulting mixture is diluted with MeOH (5 mL), filtered and concentrated. The residue is purified on SiO$_2$ (using a solvent gradient from 0% EtOAc/Heptane to 60% EtOAc/Heptane) to yield 28-2.

The title product (28) is synthesized from 28-2 according to Method 7 described for the synthesis of Example 16 from intermediate I. MS (ES+): m/z 565.4 [M+H]$^+$.

The following compounds were prepared in a similar manner utilizing the appropriate intermediates described herein
Example 29, 37-40, 63-71, 74-76, 79-80, 98-102
Method 23

Synthesis of Example 34

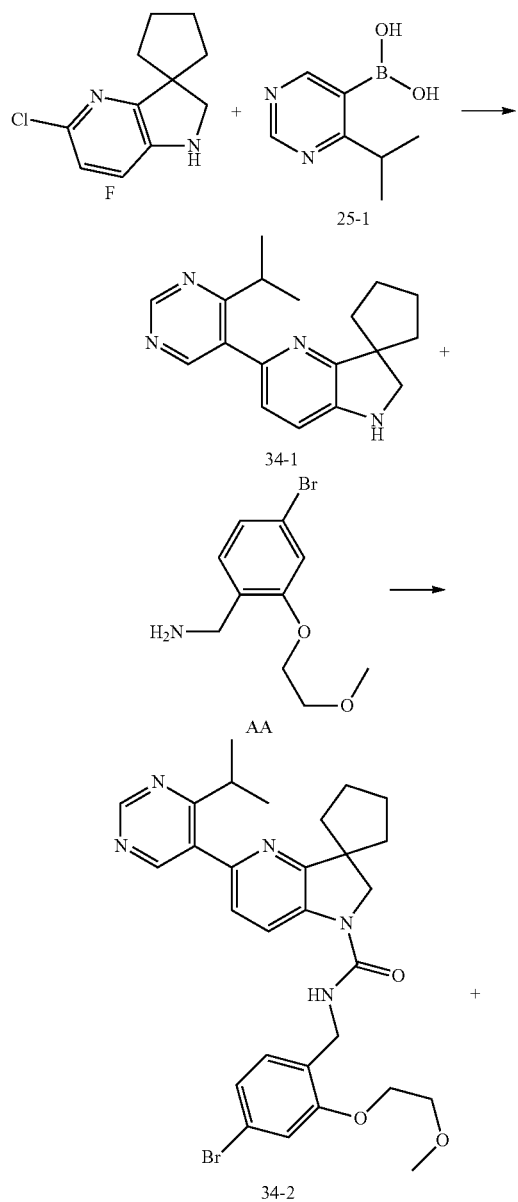

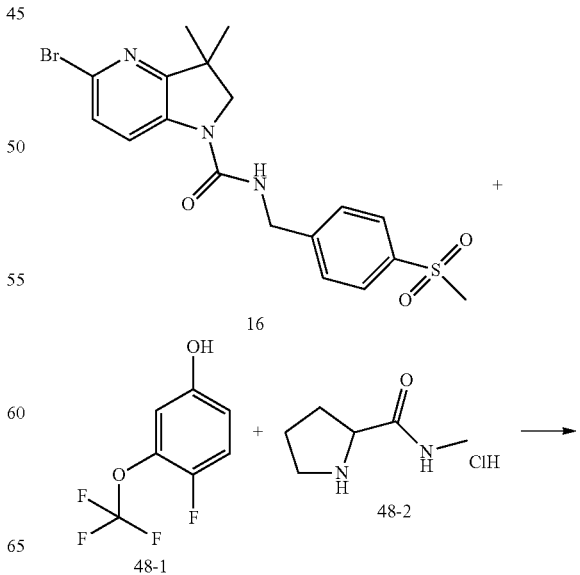

Intermediate 34-1 is synthesized from F according to Method 16 described for the synthesis of 6-2 from D.

Intermediate 34-2 is synthesized from 34-1 and AA according to Method 7 described for the synthesis of Example 16 from 1.

To a solution of 34-2 (35 mg, 0.06 mmol) in DMSO (1 mL) is added zinc cyanide (28 mg, 0.24 mmol) and tetrakistriphenylphosphane palladium (14 mg, 0.012 mmol). After purged with ArAr for 5 min, the reaction mixture is heated to 120° C. for 3 h in a Biotage microwave reactor. The resulting mixture is diluted with MeOH (2 mL), filtered and concentrated. The crude was purified by reverse phase prep HPLC eluting with 10-100% CH$_3$CN in water (+0.1% TFA). The concentrated solid was basified by PL-HCO$_3$ MP column to yield title compound 34. MS (ES+): m/z 527.4 [M+H]$^+$.

Method 24

Synthesis of Example 48

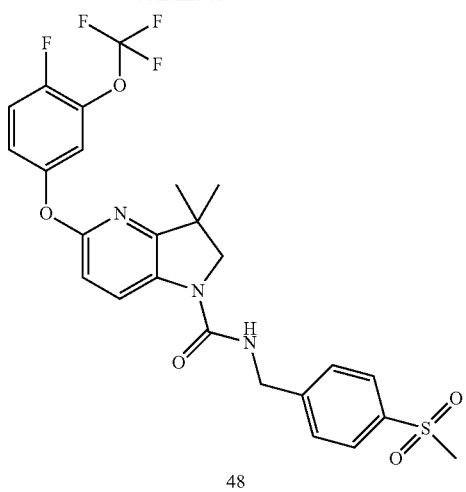

48

A solution of 16 (80 mg, 0.18 mmol), 48-1 (72 mg, 0.37 mmol) and 48-2 (9 mg, 0.055 mmol) in DMSO (2 mL) is bubbled with Ar for 5 min. To the resulting mixture is added cesium carbonate (119 mg, 0.37 mmol), followed by copper iodide (4 mg, 0.018 mmol). The vessel is capped and heated to 150° C. for 1 h in a Biotage microwave reactor. The reaction mixture is cooled, diluted with MeOH (5 mL), filtered and concentrated. The crude was purified by reverse phase prep HPLC eluting with 10-100% CH$_3$CN in water (+0.1% TFA). The concentrated solid was basified by PL-HCO$_3$ MP column to yield title compound 48. MS (ES+): m/z 554.3 [M+H]$^+$.

The following compounds were prepared in a similar manner:

Example 49, 59-61

Method 25

Synthesis of Example 82

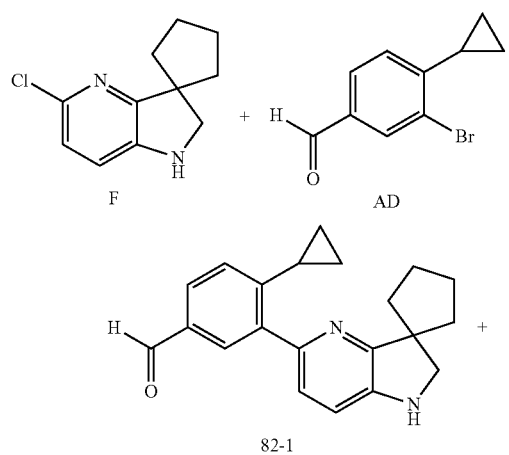

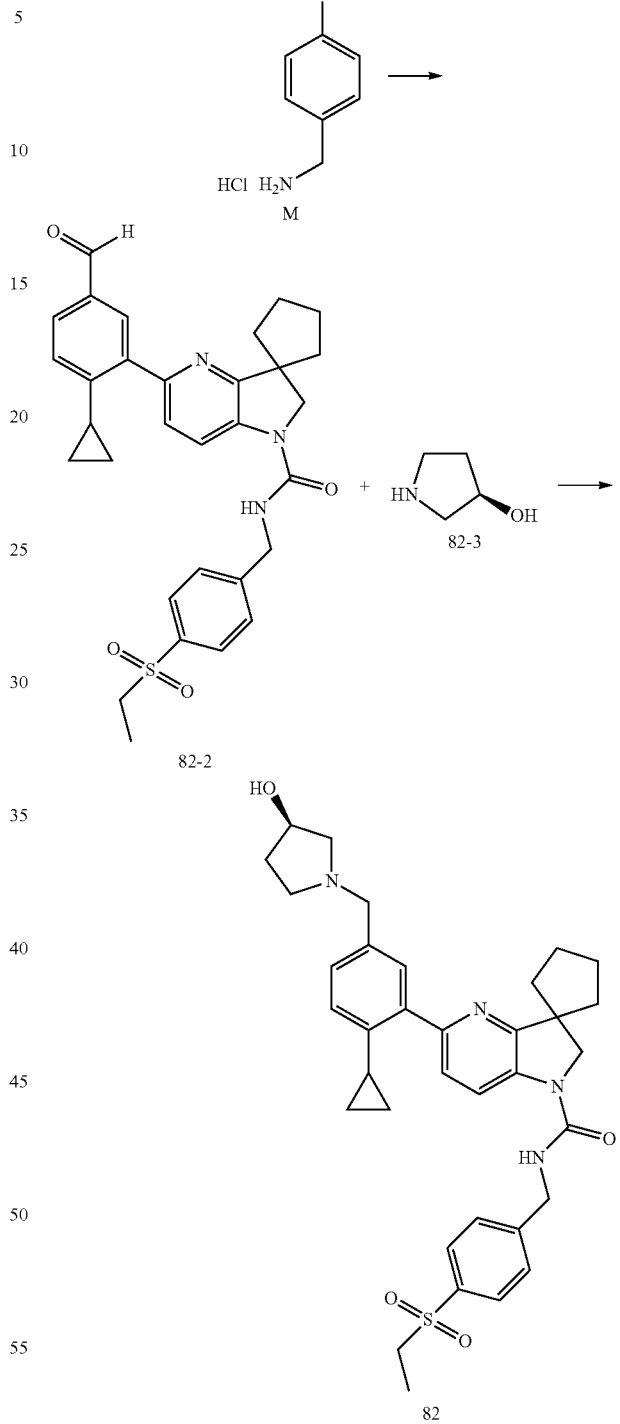

Intermediate 82-2 is synthesized from F and AD according to Method 22 described for the synthesis of Example 28 from intermediate F.

To a solution of of 82-2 (46 mg, 0.085 mmol) and 82-3 (15 mg, 0.17 mmol) in CH$_2$Cl$_2$ (2 mL) is added Na(OAc)$_3$BH (36 mg, 0.17 mmol). The reaction mixture is stirred at room temperature for 18 h. The reaction is diluted with MeOH (5 mL) and concentrated. The residue is taken up in MeOH and added to dilute aqueous Na₂CO₃. The resulting solid is isolated by filtration and dried to yield Compound 82. MS (ES+): m/z 615.4 [M+H]⁺.

The following compounds were prepared in a similar manner:

Example 83-85
Method 26

Synthesis of Example 95

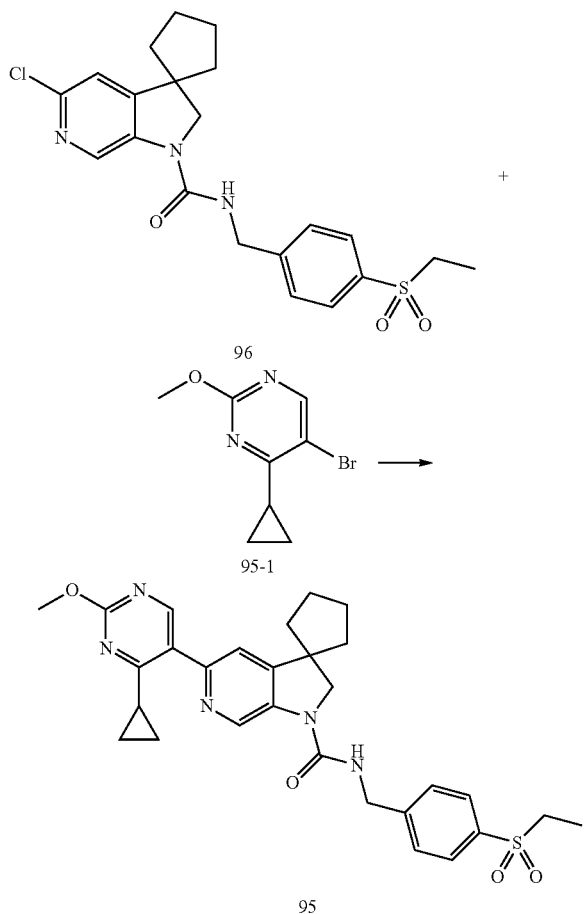

n-Butyl lithium in hexane (1.6 M, 0.491 ml, 0.786 mmol) is added dropwise to a solution of 95-1 (50 mg, 0.655 mmol) and triisopropyl borate (0.226 ml, 0.982 mmol) THF (3 mL) and the solution is stirred 30 min at −78°, then allowed to warm to room temperature and stirred for 1 h. 1N HCl is added to the solution, is extracted with EtOAc (3×), washed with H₂O (2×), dried over anhydrous Na₂SO₄, and concentrated. The aqueous phase is neutralized to pH 7 with 2N NaOH and aqueous Na₂CO₃, then extracted with 1:1 EtOAc/n-butanol (4×), washed with water (2×), concentrated and combined with first batch oil. The crude was purified by reverse phase prep HPLC eluting with 5-70% 1.6 M in water (+0.1% TFA), concentrated. The solid is dissolved in DMSO (1 mL), to which is added 96 (40 mg, 0.097 mmol), catalyst dichloropalladium 4-ditert-butylphosphanyl-N,N-dimethyl-aniline (6.5 mg, 0.009 mmol), and aqueous Na₂CO₃ (2M, 0.184 ml, 0.369 mmol, 4 E). The mixture is heated at 140° for 40 min in a Biotage microwave reactor. The resulting mixture is filtered through celite, washing with EtOAc (10 mL), then washed with water (5 mL), dried over anydrous Na₂SO₄, filtered and concentrated. The crude is purified by preparatice TLC (8% MeOH/CH₂Cl₂) to yield Compound 95. MS (ES+): m/z 548.3 [M+H]⁺.

Method 27
Synthesis of Intermediate AE

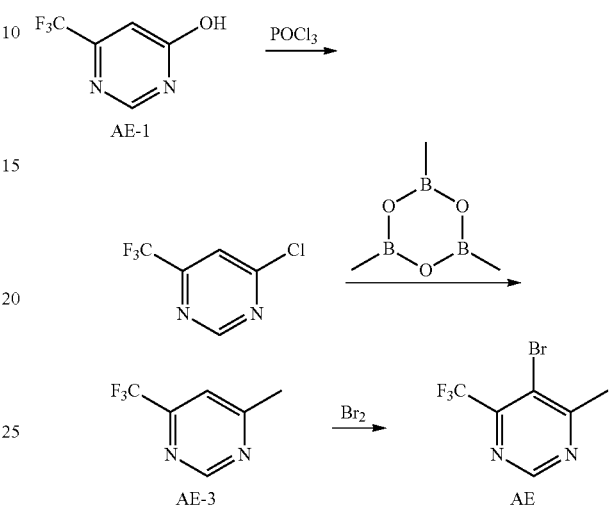

A mixture of AE-1 (40 g, 243.8 mmol), quinoline (17 g, 131.6 mmol) and POCl₃ (27.2 ml, 292.5 mmol) in toluene (400 mL) is heated to 100° C. and stirred for 5 h. After cooling down to room temperature, the mixture is absorbed onto silica gel and purified by chromatography on silica gel to yield intermediate AE-2.

A solution of AE-2 (12 g, 65.7 mmol), 2,4,6-trimethyl-1, 3,5,2,4,6-trioxatriborane (20.6 g, 164.4 mmol), K₂CO₃ (27 g, 197.2 mmol), Pd(dppf)Cl₂ (2.4 g) and Ag₂O (2.4 g) in THF (120 mL) is stirred at reflux for 25 h. After cooling down to room temperature, the mixture is absorbed onto silica gel and purified by chromatography on silica gel to yield intermediate AE-3.

To the solution of AE-3 (9 g, 55.5 mmol) in EtOH (90 ml) is added dropwised Br₂ (35.5 g, 222.1 mmol) at −10° C. The mixture is warmed to room temperature and stirred overnight. The reaction mixture is quenched by aqueous Na₂S₂O₃ solution and basified by aqueous Na₂CO₃ solution (~pH 8). The mixture is extracted with EtOAc and the combined organic phase is dried over Na₂SO₄ and evaporated under reduced pressure. The crude product is purified by HPLC to yield intermediate AE. MS (ES+): m/z 242.9 [M+H]⁺.

Method 28
Synthesis of Intermediate AF

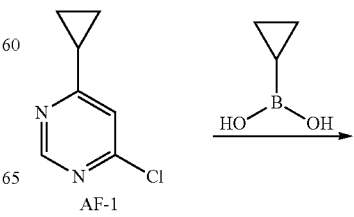

-continued

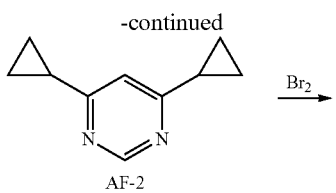
AF-2

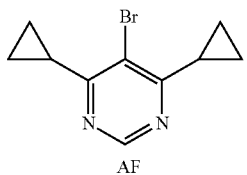
AF

To a solution of AF-1 (2.5 g, 16.17 mmol), boronic acid (4.167 g, 48.51 mmol) and aqueous Na₂CO₃ (2M, 24.26 mL, 48.51 mmol) in dioxane (30 mL) is added Reider's catalyst (572.5 mg, 0.81 mmol). The vessel is sealed and heated to 130° C. for 2 h. The vessel is cooled to room temperature, diluted with MeOH and filtered. The filtrate is concentrated and purified by SiO₂ flash chromatography (10-20% AcOEt/Heptane) to yield intermediate AF-2.

Br₂ (658 mg, 4.12 mmol) is added into a solution of AF-2 (660 mg, 4.12 mmol) in EtOH (15 mL) at −10° C. The reaction was stirred at room temperature for 3 h. ammonia/MeOH (1 mL) is added to neutralize. The mixture is concentrated and purified by SiO₂ flash chromatography (0-20% EtOAc/Heptane) to yield intermediate AF. MS (ES+): m/z 240.9 [M+H]⁺.

Method 29
Synthesis of Intermediate AG

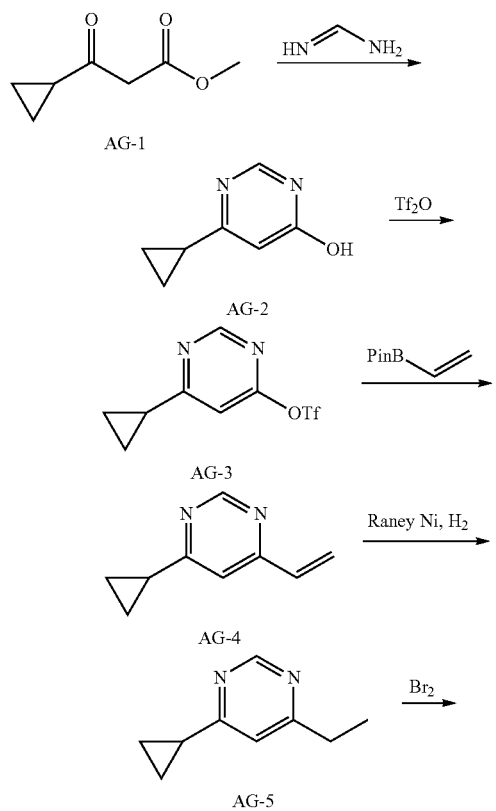

-continued

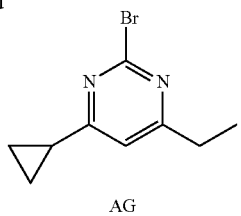
AG

A mixture of AG-1 (50.0 g, 0.35 mol), CHN₂H₃.AcOH (73 g, 0.70 mol) and NaOMe (133.0 g, 2.4 mol) in MeOH (1.5 L) is stirred at 16° C. for 2 days. The reaction mixture is acidified to pH7 with acetic acid and filtered. The filtrate iss concentrated under reduced pressure and the crude product is purified by chromatography on silica gel to yield intermediate AG-2.

To a stirred solution of AG-2 (18.0 g, 0.13 mol) and TEA (40.1 g, 0.4 mol) in 800 mL anhydrous DCM is added dropwise the solution of Tf₂O (44.8 g, 0.15 mol) in 500 mL DCM below 0° C. After the addition, the mixture is stirred for 3 h. The reaction mixture is quenched with 200 mL of water and extracted with DCM (3×100 mL). The combined organic phase is washed with aqueous NaHCO₃ solution, dried over Na₂SO₄, evaporated under reduced pressure and purified by chromatography on silica gel to yield intermediate AG-3.

A mixture of AG-3 (17.0 g, 0.06 mol), vinyl boronic acid pinacolester (29.3 g, 0.09 mol), K₂CO₃ (26.3 g, 0.19 mol), Ag₂O (1.7 g, 10% Wt) and Pd(dppf)Cl₂ (1.7 g, 10% Wt) in anhydrous THF (400 mL) is stirred at reflux under N₂ atmosphere for 18 hours. The reaction is cooled to rt and filtered, the filtrate was concentrated under reduced pressure and the residue is purified by chromatography on silica gel to afford intermediate AG-4

A mixture of AG-4 (3.1 g, 0.02 mol) and Raney Ni (3.0 g) in 40 mL EtOH is stirred under an H₂ atmosphere for 16 h. The reaction is filtered, concentrated under reduced pressure and the residue containing intermediate AG-5 was used without purification.

To a stirred solution of AG-5 (5.2 g, 0.03 mol) in 100 mL of EtOH is added Br₂ (14.0 g, 0.09 mol) below −10° C. After the addition, the mixture is stirred at room temperature for 30 min. The reaction mixture is quenched by the addition of 20 mL of aqueous Na₂S₂O₃ solution and brought to pH 8 with the addition of aqueous Na₂CO₃ solution. The mixture is extracted with EtOAc (3×40 mL) and the combined organic phase is dried over Na₂SO₄, evaporated under reduced pressure and purified by chromatography on silica gel to yield intermediate AG. MS (ES+): m/z 228.9 [M+H]⁺.

Method 30
Synthesis of Intermediate AH

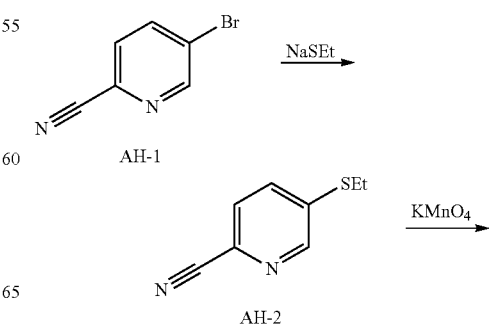

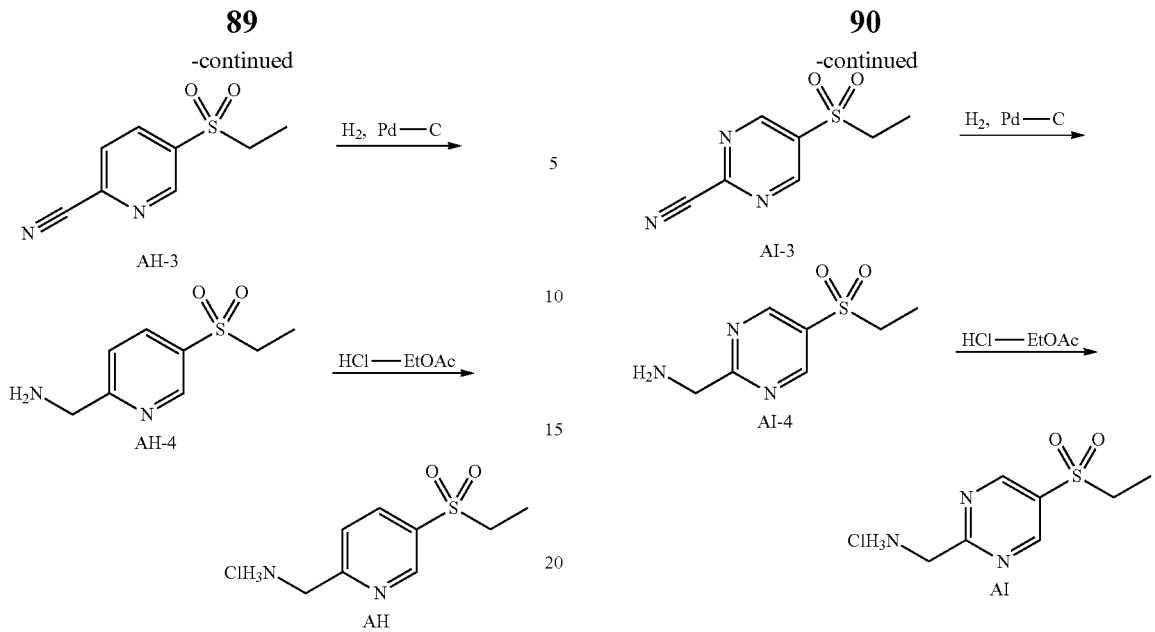

A mixture of AH-1 (8 g, 43.96 mmol), K₂CO₃ (7.88 g, 57.1 mmol) and sodium ethanethiolate (4.06 g, 48.3 mmol) in NMP (60.0 mL) under nitrogen is stirred at room temperature overnight. The reaction mixture is poured into water and filtered. The precipitate is washed with water and dried under vacuum to yield intermediate AH-2.

To a suspension of AH-2 (6 g, 36.6 mmol) in AcOH (2.63 g, 43.8 mmol) is added a solution of KMnO₄ (5.78 g, 36.6 mmol) in H₂O (20.0 ml) dropwise. The reaction mixture is stirred at room temperature for 15 h. The mixture was diluted with water and extracted with EtOAc. The organic layers are dried with anhydrous Na₂SO₄, evaporated under reduced pressure and purified by silica gel column chromatography to yield intermediate AH-3.

A solution of AH-3 (3.3 g, 16.8 mmol) and Pd/C (500 mg, 10% on carbon catalyst) in MeOH (30 ml) is stirred at room temperature under H₂ (50 psi) for 8 h. The mixture is filtered and the filtrate was concentrated under reduced pressure to afford intermediate AH-4.

To a stirred solution of AH-4 (2.5 g, 12.5 mmol) in EtOAc (30 mL) is added HCl-EtOAc (20.0 ml, 2 M). The solution is stirred at room temperature for 5 h then filtered to yield intermediate AH. MS (ES+): m/z 201.2 [M+H]⁺.

Method 31

Synthesis of Intermediate AI

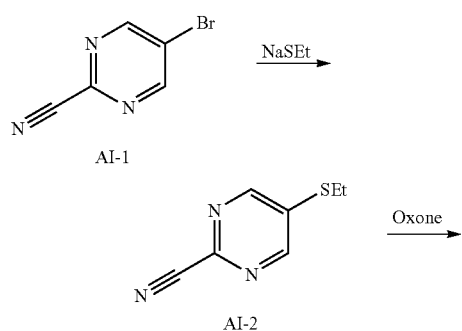

A mixture of AI-1 (11.0 g, 59.8 mmol), K₂CO₃ (10.7 g, 77.4 mmol) and sodium ethanethiolate (5.5 g, 65.4 mmol) in DMF (100 mL) is stirred at room temperature under nitrogen overnight. The mixture is diluted with water and extracted with EtOAc. The organic layers are dried with anhydrous Na₂SO₄, evaporated under reduced pressure and purified by silica gel column chromatography to yield intermediate AI-2.

To a suspension of AI-2 (8.2 g, 49.6 mmol) in acetone (50 mL) and H₂O (50 mL) is added Oxone (70 g, 114 mmol) at room temperature. The reaction mixture is stirred at 40° C. for 15 h. The mixture is diluted with water and extracted with EtOAc. The organic layers are dried with anhydrous Na₂SO₄, evaporated under reduced pressure and purified by silica gel column chromatography to yield intermediate AI-3.

A solution of AI-3 (2.0 g, 10.1 mmol), Ni (400 mg, catalyst), Boc₂O (3.3 g, 15.1 mmol) and Et₃N (3.0 g, 29.6 mmol) in THF (30 ml) is stirred at room temperature under H₂ (50 psi) for 8 h. The mixture is filtered and the filtrate was concentrated under reduced pressure. The crude residue is purified by silica gel column chromatography to yield intermediate AI-4.

To a stirred solution of AI-4 (670 mg, 2.2 mmol) in EtOAc (5 mL) is added HCl-EtOAc (10 ml, 2 M) at room temperature. The solution is stirred at room temperature for 3 h and the solvent is removed under reduced pressure to yield intermediate AI. MS (ES+): m/z 202.1 [M+H]⁺.

Biological Activity

The compounds of the present invention have activity as modulators of RORγt (retinoid-related orphan receptor γt).

RGA Assay

A nuclear receptor transactivation assay was performed to quantitate the ability of test compounds to inhibit RORγt transactivation of a luciferase reporter. A similar assay is described in: Khan et al., Bioorganic & Medicinal Chemistry Letters 23 (2013), 532-536. The system uses transiently transfected HEK 293 cells cotransfected with two plasmids (pGL4.3, luc2P/GAL4UAS/Hygro, and pBIND, Gal4DBD hRORC LBD1-3). The positive control is co-transiently transfected with both plasmids, and the negative control contains the pGL4.3 promoter sequence. Assays were assembled in 384 well plates where transiently transfected cells and test compound at varying concentrations were incubated for 20-24 hours. The next day, assays plates are taken out and equillibrated at RT for 20-30 minutes. Bright-Glo™ Luciferase Assay System is used to detect Luciferase production. After addition of Bright GLO detection reagent, the plates were incubated at RT for 20 minutes. The plates were read on an Envision plate reader to measure luminescence signal. The RLU signal is converted to POC relative to control and blank wells.

Cell Seeding Media:
RPMI 1640-Invitrogen #11875135), 2.5% FBS-Invitrogen #26140, 1×Penicillin-Streptomycin-Gibco #15140
Compound Dilution Buffer:
1×HBSS-Invitrogen #14025126
Assay Plates: Greiner #781080-020
Bright Glo Luciferase Assay System: Promega #E2620
Thaw lysis buffer provided in kit, add 100 mL lysis buffer to substrate powder.

The below table presents the results obtained when the compounds of the present invention were tested in the above assay, demonstrating their activity as modulators of RORγt:

TABLE II

Table of Biological Activity in RGA Assay

| Example | RGA IC50 (nM) |
|---|---|
| 1 | 1600 |
| 2 | >30000 |
| 3 | >30000 |
| 4 | 12000 |
| 5 | >30000 |
| 6 | 24000 |
| 7 | >30000 |
| 8 | >30000 |
| 9 | 4300 |
| 10 | 11000 |
| 11 | 110 |
| 12 | 480 |
| 13 | 5200 |
| 14 | 3400 |
| 15 | 480 |
| 16 | >30000 |
| 17 | >30000 |
| 18 | 3400 |
| 19 | 10000 |
| 20 | 19000 |
| 21 | 12000 |
| 22 | >30000 |
| 23 | 1800 |
| 24 | 5900 |
| 25 | 1200 |
| 26 | 350 |
| 27 | 8000 |
| 28 | >30000 |
| 29 | 1700 |
| 30 | 1900 |
| 31 | >30000 |
| 32 | 17000 |
| 33 | 1200 |
| 34 | 11000 |
| 35 | 2100 |
| 36 | 16000 |
| 37 | >30000 |
| 38 | >30000 |
| 39 | >30000 |
| 40 | 1600 |
| 41 | >30000 |
| 42 | 10000 |
| 43 | 8500 |
| 44 | 18000 |
| 45 | 9100 |
| 46 | 4100 |
| 47 | 15000 |
| 48 | 6600 |
| 49 | 4100 |
| 50 | 8600 |
| 51 | 710 |
| 52 | 930 |
| 53 | 860 |
| 54 | 1400 |
| 55 | 1100 |
| 56 | 1600 |
| 57 | 5200 |
| 58 | 8000 |
| 59 | >30000 |
| 60 | 8500 |
| 61 | 7600 |
| 62 | >30000 |
| 63 | >30000 |
| 64 | 16000 |
| 65 | 18000 |
| 66 | 650 |
| 67 | 830 |
| 68 | 2500 |
| 69 | 1100 |
| 70 | 760 |
| 71 | 1300 |
| 72 | 2800 |
| 73 | 1500 |
| 74 | 310 |
| 75 | 3700 |
| 76 | 15000 |
| 77 | 4000 |
| 78 | 2400 |
| 79 | 380 |
| 80 | 840 |
| 81 | 1500 |
| 82 | 7000 |
| 83 | 6900 |
| 84 | >30000 |
| 85 | >30000 |
| 86 | 2600 |
| 87 | 3900 |
| 88 | >30000 |
| 89 | >30000 |
| 90 | >30000 |
| 91 | >30000 |
| 92 | >30000 |
| 93 | 740 |
| 94 | 3800 |
| 95 | >30000 |
| 96 | >30000 |
| 97 | 200 |
| 98 | 370 |
| 99 | 360 |
| 100 | 220 |
| 101 | 420 |
| 102 | 730 |

Methods of Therapeutic Use

On the basis of their biological properties the compounds of formula (I) according to the invention, or their tautomers, racemates, enantiomers, diastereomers, mixtures thereof and the salts of all the above-mentioned forms are suitable for treating autoimmune and allergic disorders in that they exhibit good modulatory effect upon RORC.

The present invention is therefore directed to compounds of general formula (I), and the pharmaceutically acceptable salts thereof, and all tautomers, racemates, enantiomers, diastereomers, mixtures thereof, which are useful in the treatment of a disease and/or condition wherein the activity of ROR modulators is of therapeutic benefit, including but not limited to the treatment of autoimmune or allergic disorders.

Such disorders that may be treated by the compounds of the invention include for example: psoriasis, rheumatoid arthritis, systemic lupus erythromatosis, scleroderma, Type II diabetes, asthma, allergic rhinitis, allergic eczema, multiple sclerosis, juvenile rheumatoid arthritis, juvenile idiopathic arthritis, inflammatory bowel diseases (including, e.g., Crohn's disease and ulcerative colitis), graft versus host disease, spondyloarthropathies (including, e.g., psoriatic arthritis and ankylosing spondylitis), and uveitis.

For treatment of the above-described diseases and conditions, a therapeutically effective dose will generally be in the range of approximately 0.01 mg to about 10 mg/kg of body weight per dosage of a compound of the invention; preferably, from about 0.1 mg to about 5 mg/kg of body weight per dosage. For example, for administration to a 70 kg person, the dosage range would be approximately 0.7 mg to about 750 mg per dosage of a compound of the invention, preferably from about 7.0 mg to about 350 mg per dosage. Some degree of routine dose optimization may be required to determine an optimal dosing level and pattern. The active ingredient may be administered from 1 to 6 times a day.

General Administration and Pharmaceutical Compositions

When used as pharmaceuticals, the compounds of the invention are typically administered in the form of a pharmaceutical composition. Such compositions can be prepared using procedures well known in the pharmaceutical art and comprise at least one compound of the invention. The compounds of the invention may also be administered alone or in combination with adjuvants that enhance stability of the compounds of the invention, facilitate administration of pharmaceutical compositions containing them in certain embodiments, provide increased dissolution or dispersion, increased antagonist activity, provide adjunct therapy, and the like. The compounds according to the invention may be used on their own or in conjunction with other active substances according to the invention, optionally also in conjunction with other pharmacologically active substances. In general, the compounds of this invention are administered in a therapeutically or pharmaceutically effective amount, but may be administered in lower amounts for diagnostic or other purposes.

Administration of the compounds of the invention, in pure form or in an appropriate pharmaceutical composition, can be carried out using any of the accepted modes of administration of pharmaceutical compositions. Thus, administration can be, for example, orally, buccally (e.g., sublingually), nasally, parenterally, topically, transdermally, vaginally, or rectally, in the form of solid, semi-solid, lyophilized powder, or liquid dosage forms, such as, for example, tablets, suppositories, pills, soft elastic and hard gelatin capsules, powders, solutions, suspensions, or aerosols, or the like, preferably in unit dosage forms suitable for simple administration of precise dosages. The pharmaceutical compositions will generally include a conventional pharmaceutical carrier or excipient and a compound of the invention as the/an active agent, and, in addition, may include other medicinal agents, pharmaceutical agents, carriers, adjuvants, diluents, vehicles, or combinations thereof. Such pharmaceutically acceptable excipients, carriers, or additives as well as methods of making pharmaceutical compositions for various modes or administration are well-known to those of skill in the art. The state of the art is evidenced, e.g., by Remington: The Science and Practice of Pharmacy, 20th Edition, A. Gennaro (ed.), Lippincott Williams & Wilkins, 2000; Handbook of Pharmaceutical Additives, Michael & Irene Ash (eds.), Gower, 1995; Handbook of Pharmaceutical Excipients, A. H. Kibbe (ed.), American Pharmaceutical Ass'n, 2000; H. C. Ansel and N. G. Popovish, Pharmaceutical Dosage Forms and Drug Delivery Systems, 5th ed., Lea and Febiger, 1990; each of which is incorporated herein by reference in their entireties to better describe the state of the art. As one of skill in the art would expect, the forms of the compounds of the invention utilized in a particular pharmaceutical formulation will be selected (e.g., salts) that possess suitable physical characteristics (e.g., water solubility) that are required for the formulation to be efficacious.

All patent and non-patent documents or literature cited in this application are herein incorporated by reference in their entirety.

The invention claimed is:
1. A compound of formula (I)

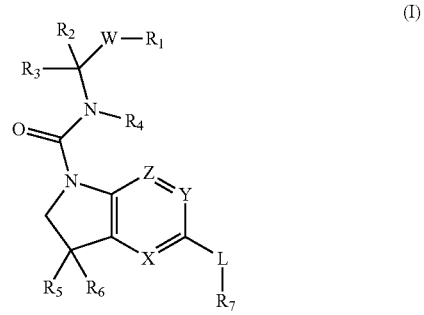

$R_1$ is:
—CN,
—S(O)$_m$C$_{1-6}$alkyl,
—S(O)$_m$C$_{1-6}$cyanoalkyl,
—S(O)$_m$C$_{1-6}$haloalkyl,
—S(O)$_m$C$_{3-6}$cycloalkyl,
—S(O)$_m$C$_{1-6}$ hydroxyalkyl,
—S(O)$_m$C$_{1-6}$alkyloxy,
—SO$_2$NR$_a$R$_b$,
—NR$_a$S(O)$_m$C$_{1-6}$alkyl,
—NR$_a$S(O)$_m$C$_{3-6}$cycloalkyl,
—S(O)(NRc) C$_{1-6}$alkyl,
—S(O)(NRc) C$_{3-6}$cycloalkyl or
—S(O)(NRc) NR$_a$R$_b$ wherein R$_a$ and R$_b$ are each independently H, C$_{1-6}$alkyl, C$_{3-6}$cycloalkyl, C$_{1-6}$haloalkyl, C$_{1-6}$cyanoalkyl, or C$_{1-6}$alkyloxy; or R$_a$ and R$_b$ taken together with the nitrogen to which they are attached form a C$_{2-6}$ heterocyclic ring optionally containing 1-4 additional groups selected from NH, O and S;

R$_c$ is each independently H, C$_{1-6}$alkyl, C$_{3-6}$cycloalkyl, or C$_{1-6}$alkyloxy;

W is:
C$_{6-14}$ aryl,
a C$_{2-10}$ heteroaryl containing 1-4 groups selected from N, NH, O and S,
saturated and partially saturated C$_{2-10}$ heterocyclyl containing 1-4 groups selected from N, NH, O and S, or
saturated and partially saturated C$_{3-12}$ cycloalkyl ring,
wherein each W is optionally substituted with 0-4 substituents selected from the group consisting of cyano, halo, hydroxy, C$_{1-6}$alkyl, C$_{1-6}$ haloalkyl, C$_{1-6}$ hydroxyalkyl, C$_{2-6}$ alkenyl, C$_{2-6}$ haloalkenyl, C$_{2-6}$ alkynyl, C$_{2-6}$ haloalkynyl, C$_{3-6}$ cycloalkyl, C$_{3-6}$ heterocycle containing 1-4 groups selected from NH, O and S, C$_{1-6}$ alkoxy, C$_{3-6}$ cycloalkyl-oxy, —S(O)$_m$C$_{1-6}$ alkyl, —S(O)$_m$C$_{3-6}$ cycloalkyl, CN, —C(O)—NR$_c$R$_d$, —C(O)—OR$_c$, —NR$_c$R$_d$, NR$_c$R$_d$—C$_{1-6}$alkyl-, and R$_c$O—C$_{1-6}$alkoxy NR$_c$R$_d$—C$_{1-6}$alkoxy-,
wherein R$_c$ and R$_d$ is each independently H, C$_{1-6}$ alkyl, C$_{2-6}$ alkenyl, C$_{2-6}$ alkynyl, C$_{3-12}$ cycloalkyl, C$_{6-14}$ aryl, C$_{2-6}$ heterocycle containing 1-4 groups selected from NH, O and S, or a C$_{2-10}$heteroaryl containing 1-4 groups selected from N, NH, O and S,
or Rc and R$_d$ taken together with the nitrogen to which they are attached form a C$_{2-6}$ heterocyclic ring optionally containing 1-4 additional groups selected from NH, O and S;

R$_2$ is:
—C$_{1-6}$alkyl,
—C$_{3-6}$cycloalkyl,
—C$_{1-6}$alkyloxy,
—C$_{1-6}$ hydroxyalkyl,
—C$_{1-6}$haloalkyl,
—H, or
—C(O)OR$_e$, or —C(O)NR$_e$R$_f$, wherein R$_e$ and R$_f$ is each independently H or C$_{1-6}$ alkyl;

R$_3$ is:
—C$_{1-6}$alkyl,
—C$_{3-6}$cycloalkyl,
—C$_{1-6}$alkyloxy;
—H,
—C(O)OR$_e$, or C(O)NR$_e$R$_f$, wherein R$_e$ and R$_f$ is each independently H or C$_{1-6}$ alkyl;
or R$_2$ and R$_3$ taken together with the carbon to which they are attached form a C$_{3-12}$ carbocyclic ring or a C$_{2-10}$ heterocyclic containing 1-4 groups selected from NH, O and S;

R$_4$ is:
—H,
—C$_{1-6}$alkyl,
—C$_{1-6}$alkyloxy, or
—C$_{3-6}$cycloalkyl;

X, Y and Z are chosen independently from N and CR$_e$ wherein one and only one of X, Y and Z is N and R$_e$ is:
—H,
-halo,
—C$_{1-6}$alkyl,
—C$_{1-6}$ haloalkyl,
C$_{2-6}$ haloalkenyl,
C$_{2-6}$ haloalkynyl,
—C$_{3-6}$ cycloalkyl,
—C$_{1-6}$ alkoxy,
—C$_{3-6}$ cycloalkyloxy,
—O C$_{1-6}$alkyl,
—O C$_{3-6}$ cycloalkyl,
—S(O)$_m$C$_{1-6}$ alkyl,
—S(O)$_m$C$_{3-6}$ cycloalkyl,
CN,
—C(O)—NR$_f$R$_g$, —C(O)—OR$_f$, or —NR$_f$R$_g$, wherein R$_f$ and R$_g$ is each independently H or —C$_{1-6}$ alkyl;
C$_{2-6}$ alkenyl,
C$_{2-6}$ alkynyl,
C$_{3-12}$ cycloalkyl, C$_{6-14}$ aryl, C$_{3-6}$ heterocycle containing 1-4 groups selected from N, NH, O and S, or a C$_{2-10}$ heteroaryl containing 1-4 groups selected from N, NH, O and S;

R$_5$ is:
—H
-halo,
—C$_{1-6}$ alkyl,
—C$_{2-6}$ alkenyl,
—C$_{1-6}$ alkoxy,
—S(O)$_m$C$_{1-6}$alkyl,
—C$_{6-14}$ aryl,
—C$_{2-10}$ heterocyclyl containing 1-4 groups selected from N, NH, O and S,
—C$_{2-10}$ heteroaryl containing 1-4 groups selected from N, NH, O and S,
—CN,
—C$_3$-C$_6$cycloalkyl, or
—C$_{1-6}$haloalkyl,
wherein R$_5$ is optionally substituted with 0-5 halo, C$_{1-6}$ alkyl, C$_{1-6}$ alkoxy, —S(O)$_m$C$_{1-6}$alkyl, C$_{6-14}$ aryl, C$_{2-10}$ heterocyclyl containing 1-4 groups selected from N, NH, O and S, or a C$_{2-10}$ heteroaryl containing 1-4 groups selected from N, NH, O and S, CN, C$_3$-C$_6$cycloalkyl, OH or —C(O)—NR$_a$R$_b$, R$_6$ is:
-halo,
—C$_{1-6}$ alkyl,
C$_{2-6}$ alkenyl,
—C$_{1-6}$ alkoxy,
—S(O)$_m$C$_{1-6}$alkyl,
—C$_{6-14}$ aryl,
—C$_{2-10}$ heterocyclyl containing 1-4 groups selected from N, NH, O and S,
—C$_{2-10}$ heteroaryl containing 1-4 groups selected from N, NH, O and S,
—H,
—CN,
—C$_3$-C$_6$cycloalkyl, or
—C$_{1-6}$haloalkyl,
wherein R$_6$ is optionally substituted with 0-5 halo, C$_{1-6}$ alkyl, C$_{1-6}$ alkoxy, —S(O)$_m$C$_{1-6}$alkyl, C$_{6-14}$ aryl, C$_{2-10}$ heterocyclyl containing 1-4 groups selected from N, NH, O and S, or a C$_{2-10}$ heteroaryl containing 1-4 groups selected from N, NH, O and S, CN, C$_3$-C$_6$cycloalkyl, OH or —C(O)—NR$_a$R$_b$,
or R$_5$ and R$_6$ taken together with the carbon to which they attached form a C$_{3-12}$ carbocyclic ring or a C$_{2-10}$ heterocyclic containing 1-4 groups selected from N, NH, O and S;

L is:
a direct bond,
—C=C—

—C≡C—,

—S(O)$_m$—,
—NR$_a$S(O)$_m$,
—S(O)$_m$NR$_a$—
—O—,
—C(O)—,
—(CH$_2$)$_n$—,
—O—(CH$_2$)$_n$—,
—N(R$_a$)—,
—N(R$_a$)—(CH$_2$)$_n$—,
—(CH$_2$)$_n$—N(R$_a$)—,
—C(O)—N(R$_a$)—,
—C(O)—N(R$_a$)—(CH$_2$)$_n$— or
—N(R$_a$)—C(O)—N(R$_b$)—;
wherein R$_a$ and R$_b$ is each independently H or C$_{1-3}$ alkyl;

$R_7$ is:

halo, cycloalkyl, cycloalkenyl,

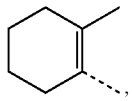

—$C_{6-14}$ aryl,

—$C_{2-10}$ heterocyclyl containing 1-4 groups selected from N, NH, O and S,

—$C_{2-10}$ heteroaryl containing 1-4 groups selected from N, NH, O and S, wherein $R_7$ is optionally substituted with 0-5 substituents selected from the group consisting of halogen, hydroxy, $C_{1-6}$alkyl, $C_{1-6}$ haloalkyl, $C_{1-6}$ hydroxyalkyl, $C_{2-6}$ haloalkenyl, $C_{2-6}$ haloalkynyl, $C_{3-6}$ cycloalkyl, $C_{3-7}$ heterocycle containing 1-4 groups selected from N, NH, O and S, $C_{6-14}$ aryl, $C_{2-10}$ heteroaryl containing 1-4 groups selected from N, NH, O and S, $C_{1-6}$ alkoxy, $C_{1-6}$ haloalkoxy, $C_{3-6}$ cycloalkyloxy, —$S(O)_m C_{1-6}$ alkyl, —$S(O)_m C_{3-6}$ cycloalkyl, CN, —C(O)—$NR_c R_d$, —C(O)—$OR_c$, $NR_c R_d$ and $NR_c R_d C_{1-6}$alkyl-, wherein $R_c$ and $R_d$ is each independently H, $C_{1-6}$ alkyl, $C_{2-6}$ alkenyl, $C_{2-6}$ alkynyl, cycloalkyl, —$C_{6-14}$ aryl, $C_{2-10}$ heterocyclyl containing 1-4 groups selected from N, NH, O and S, or a $C_{2-10}$ heteroaryl containing 1-4 groups selected from N, NH, O and S, wherein each heterocyclyl, aryl or heteroaryl is optionally substituted by $C_{1-6}$ alkyl, $C_{1-6}$ alkoxy; or Rc and Rd-together with the nitrogen to which they are attached form a $C_{2-6}$ heterocyclic ring optionally containing 1-4 additional groups selected from N, NH, O and S, wherein the heterocyclic ring is optionally substituted by $C_{1-6}$ alkyl, hydroxy or $C_{1-6}$ alkoxy;

each n is independently 1-4; each m is independently 0-2;

or a pharmaceutically acceptable salt thereof.

2. A compound of formula (I) according to claim 1, wherein:

$R_1$ is:

—$S(O)_m C_{1-6}$alkyl,

—$S(O)_m C_{1-6}$haloalkyl,

—$S(O)_m C_{3-6}$cycloalkyl,

—$SO_2 NR_a R_b$, wherein $R_a$ and $R_b$ are each independently H, $C_{1-6}$alkyl, $C_{3-6}$cycloalkyl, or $C_{1-6}$alkyloxy, or $R_a$ and $R_b$ taken together with the nitrogen to which they are attached form a $C_{2-6}$ heterocyclic ring optionally containing 1-4 additional groups selected from NH, O and S;

—S(O)(NRc) $C_{1-6}$alkyl,

—S(O)(NRc) $C_{3-6}$cycloalkyl, wherein $R_c$ is each independently H, $C_{1-6}$alkyl, $C_{3-6}$cycloalkyl, or $C_{1-6}$alkyloxy, or

—CN;

and each m is independently 0-2;

or a pharmaceutically acceptable salt thereof.

3. A compound of formula (I) according to claim 1, wherein:

W is:

$C_{6-14}$ aryl, $C_{2-10}$ heteroaryl containing 1-4 groups selected from N, NH, O and S, or bicyclo [1.1.1] pentane, wherein each W is optionally substituted with 0-4 substituents selected from the group consisting of halo, hydroxy, $C_{1-6}$alkyl, $C_{1-6}$ haloalkyl, $C_{2-6}$ haloalkenyl, $C_{2-6}$ haloalkynyl, $C_{3-6}$ cycloalkyl, $C_{1-6}$ alkoxy, $C_{3-6}$ cycloalkyloxy, —$S(O)_m C_{1-6}$ alkyl, —$S(O)_m C_{3-6}$ cycloalkyl, CN, —C(O)—$NR_c R_d$, —C(O)—$OR_c$, and $NR_c R_d$ wherein $R_c$ and $R_d$ is each independently H, $C_{1-6}$ alkyl, $C_{2-6}$ alkenyl, $C_{2-6}$ alkynyl, $C_{3-12}$ cycloalkyl, —$C_{6-14}$ aryl, $C_{2-10}$ heterocyclyl containing 1-4 groups selected from NH, O and S, or a $C_{2-10}$ heteroaryl containing 1-4 groups selected from N, NH, O and S;

or a pharmaceutically acceptable salt thereof.

4. A compound of formula (I) according to claim 1, wherein:

$R_2$ is:

H, or $C_{1-6}$alkyl; and $R_3$ is:

H, or $C_{1-6}$alkyl;

or $R_2$ and $R_3$ taken together form a cyclopropane ring or a pharmaceutically acceptable salt thereof.

5. A compound of formula (I) according to claim 1, wherein:

$R_4$ is:

H, or $C_{1-6}$alkyl;

or a pharmaceutically acceptable salt thereof.

6. A compound of formula (I) according to claim 1, wherein:

X is N, and both Y and Z are chosen independently from $CR_e$ and $R_e$ is as defined in claim 1;

or a pharmaceutically acceptable salt thereof.

7. A compound of formula (I) according to claim 1, wherein:

Y is N and both X and Z are chosen independently from $CR_e$ and $R_e$ is as defined in claim 1;

or a pharmaceutically acceptable salt thereof.

8. A compound of formula (I) according to claim 1, wherein:

$R_5$ is:

H;

$C_{1-6}$ alkyl, or $C_3$-$C_6$cycloalkyl;

wherein $R_5$ is optionally substituted with 0-5 halo, $C_{1-6}$ alkyl, $C_{1-6}$ alkoxy, —$S(O)_m C_{1-6}$alkyl, $C_{6-14}$ aryl, $C_{2-10}$ heterocyclyl containing 1-4 groups selected from NH, O and S, $C_{2-10}$ heteroaryl containing 1-4 groups selected from N, NH, O and S, CN, or $C_3$-$C_6$cycloalkyl;

$R_6$ is:

H;

$C_{1-6}$ alkyl, or $C_3$-$C_6$cycloalkyl;

wherein $R_6$ is optionally substituted with 0-5 substituents selected from the group consisting of halogen, $C_{3-6}$ cycloalkyl, $C_{1-6}$ alkoxy, —$S(O)_m C_{1-6}$ alkyl, —CN, $C_{1-6}$ alkyl, $C_{6-14}$ aryl, $C_{2-10}$ heterocyclyl containing 1-4 groups selected from NH, O and S, $C_{2-10}$ heteroaryl containing 1-4 groups selected from N, NH, O and S;

or $R_5$ and $R_6$ taken together with the carbon to which they attached form a $C_{3-12}$ carbocyclic ring or a $C_{2-10}$ heterocyclic ring containing 1-4 groups selected from NH, O and S;

or a pharmaceutically acceptable salt thereof.

9. A compound of formula (I) according to claim 1, wherein:

L is:
a bond,
—O— or
—O—CH$_2$—;
or a pharmaceutically acceptable salt thereof.

10. A compound of formula (I) according to claim 1, wherein:

R$_7$ is:
halo, or
C$_{6-14}$ aryl or C$_{2-10}$ heteroaryl containing 1-4 groups selected from N, NH, O and S;
wherein R$_7$ is optionally substituted with 0-5 substituents selected from the group consisting of halogen, hydroxy, C$_{1-6}$ alkyl, C$_{1-6}$ haloalkyl, C$_{1-6}$ hydroxyalkyl, C$_{2-6}$ haloalkenyl, C$_{2-6}$ haloalkynyl, C$_{3-6}$ cycloalkyl, C$_{1-6}$ alkoxy, C$_{1-6}$ haloalkoxy, C$_{3-6}$ cycloalkyloxy, —S(O)$_m$C$_{1-6}$ alkyl, —S(O)$_m$C$_{3-6}$ cycloalkyl, —CN, —C(O)—NR$_c$R$_d$, —C(O)—OR$_c$, and NR$_c$R$_d$, wherein R$_c$ and R$_d$ is H, C$_{1-6}$ alkyl, C$_{2-6}$ alkenyl, C$_{2-6}$ alkynyl, C$_{3-12}$ cycloalkyl, C$_{6-14}$ aryl, C$_{2-6}$ heterocycle containing 1-4 groups selected from NH, O and S, or a C$_{2-10}$ heteroaryl containing 1-4 groups selected from N, NH, O and S;
each m is independently 0-2;
or a pharmaceutically acceptable salt thereof.

11. A compound of formula (I) according to claim 1, wherein:

R$_1$ is:
—S(O)$_m$C$_{1-6}$alkyl,
—S(O)$_m$C$_{3-6}$cycloalkyl, or
—SO$_2$NR$_a$R$_b$
wherein R$_a$ and R$_b$ are each independently H, C$_{1-6}$alkyl, C$_{3-6}$cycloalkyl, or C$_{1-6}$alkyloxy, or
R$_a$ and R$_b$ taken together with the nitrogen to which they are attached form a C$_{2-6}$ heterocyclic ring optionally containing 1-4 additional groups selected from NH, O and S;
or
—CN;

W is:
C$_{6-14}$ aryl or a C$_{2-10}$ heteroaryl containing 1-4 groups selected from N, NH, O and S,
wherein each W is optionally substituted with 0-4 substituents selected from the group consisting of halo, hydroxy, C$_{1-6}$alkyl, C$_{1-6}$ haloalkyl, C$_{2-6}$ haloalkenyl, C$_{2-6}$ haloalkynyl, C$_{3-6}$ cycloalkyl, C$_{1-6}$ alkoxy, C$_{3-6}$ cycloalkyloxy, —S(O)$_m$C$_{1-6}$ alkyl, —S(O)$_m$C$_{3-6}$ cycloalkyl, CN, —C(O)—NR$_c$R$_d$, —C(O)—OR$_c$, and NR$_c$R$_d$ wherein R$_d$ and R$_d$ is each independently H, C$_{1-6}$ alkyl, C$_{2-6}$ alkenyl, C$_{2-6}$ alkynyl, C$_{3-12}$ cycloalkyl, C$_{6-14}$ aryl, C$_{2-6}$ heterocycle containing 1-4 groups selected from NH, O and S, or a C$_{2-10}$ heteroaryl containing 1-4 groups selected from N, NH, O and S;

R$_2$ is:
H, or
C$_{1-6}$alkyl;

R$_3$ is:
H, or
C$_{1-6}$alkyl;

R$_4$ is:
H, or
C$_{1-6}$alkyl;

X is N, and both Y and Z are chosen independently from CR$_e$;
or Y is N and both X and Z are chosen independently from CR$_e$;

and R$_e$ is:
H,
halo,
C$_{1-6}$alkyl,
C$_{1-6}$ haloalkyl,
C$_{2-6}$ haloalkenyl,
C$_{2-6}$ haloalkynyl,
C$_{3-6}$ cycloalkyl,
C$_{1-6}$ alkoxy,
C$_{3-6}$ cycloalkyloxy,
—S(O)$_m$C$_{1-6}$ alkyl,
—S(O)$_m$C$_{3-6}$ cycloalkyl,
—CN,
—C(O)—NR$_f$R$_g$, —C(O)—OR$_f$, or —NR$_f$R$_g$, wherein R$_f$ and R$_g$ is H or C$_{1-6}$ alkyl,
—C$_{2-6}$ alkenyl,
—C$_{2-6}$ alkynyl, or
—C$_{3-12}$ cycloalkyl;

R$_5$ is:
H;
C$_{1-6}$ alkyl, or
C$_3$-C$_6$cycloalkyl;
wherein R$_5$ is optionally substituted with 0-5 halo, C$_{1-6}$ alkyl, C$_{1-6}$ alkoxy, —S(O)$_m$C$_{1-6}$alkyl, —S(O)$_m$C$_{1-6}$ alkyl, —C$_{6-14}$ aryl,
C$_{2-10}$ heterocyclyl containing 1-4 groups selected from NH, O and S, C$_{2-10}$ heteroaryl containing 1-4 groups selected from N, NH, O and S, CN, or C$_3$-C$_6$cycloalkyl;

R$_6$ is:
H;
C$_{1-6}$ alkyl, or
C$_3$-C$_6$cycloalkyl;
wherein R$_6$ is optionally substituted with 0-5 substituents selected from the group consisting of halogen, C$_{3-6}$ cycloalkyl, C$_{1-6}$ alkoxy, —S(O)$_m$C$_{1-6}$ alkyl, —CN, C$_{1-6}$ alkyl C$_{6-14}$ aryl, C$_{2-6}$ heterocycle containing 1-4 groups selected from NH, O and S, or a C$_{2-10}$ heteroaryl containing 1-4 groups selected from N, NH, O and S;
or R$_5$ and R$_6$ taken together with the carbon to which they attached form a C$_{3-12}$ carbocyclic ring;

L is:
a bond,
—O— or
—O—(CH$_2$)$_n$—;

R$_7$ is:
halo, C$_{6-14}$ aryl or C$_{2-10}$ heteroaryl containing 1-4 groups selected from N, NH, O and S;
wherein R$_7$ is optionally substituted with 0-5 substituents selected from the group consisting of halogen, hydroxy, C$_{1-6}$ alkyl, C$_{1-6}$ haloalkyl, C$_{1-6}$ hydroxyalkyl, C$_{2-6}$ haloalkenyl, C$_{2-6}$ haloalkynyl, C$_{3-6}$ cycloalkyl, C$_{1-6}$ alkoxy, C$_{1-6}$ haloalkoxy, C$_{3-6}$ cycloalkyloxy, —S(O)$_m$C$_{1-6}$ alkyl, —S(O)$_m$C$_{3-6}$ cycloalkyl, —CN, —C(O)—NR$_c$R$_d$, —C(O)—OR$_c$, and NR$_c$R$_d$, wherein R$_c$ and R$_d$ is H, C$_{1-6}$ alkyl, C$_{2-6}$ alkenyl, C$_{2-6}$ alkynyl, C$_{3-12}$ cycloalkyl, C$_{6-14}$ aryl, C$_{2-6}$ heterocycle containing 1-4 groups selected from NH, O and S, or a C$_{2-10}$ heteroaryl containing 1-4 groups selected from N, NH, O and S;
each m is independently 0-2;
or a pharmaceutically acceptable salt thereof.

12. A compound selected from the compounds in the following table:

| Example | Structure |
|---|---|
| 1 | 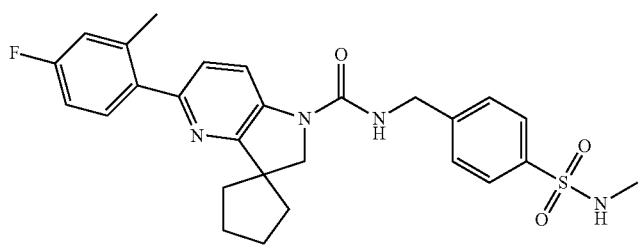 [SMILES: CNS(=O)(=O)c1ccc(CNC(=O)N2CC3(CCCC3)c3nc(-c4ccc(F)cc4C)ccc32)cc1] |
| 2 | 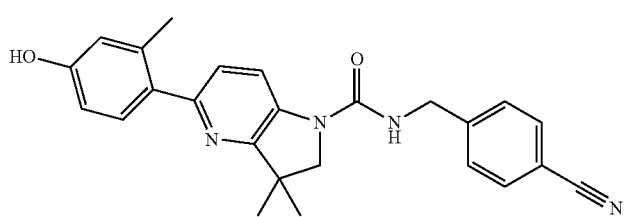 [SMILES: Cc1cc(O)ccc1-c1ccc2c(n1)C(C)(C)CN2C(=O)NCc1ccc(C#N)cc1] |
| 3 | 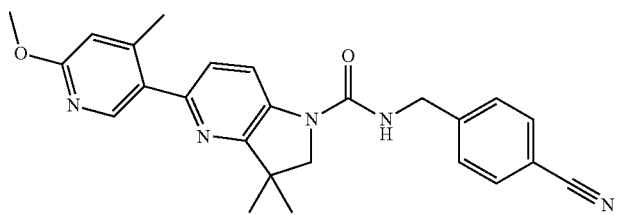 [SMILES: COc1cc(C)c(-c2ccc3c(n2)C(C)(C)CN3C(=O)NCc2ccc(C#N)cc2)cn1] |
| 4 | 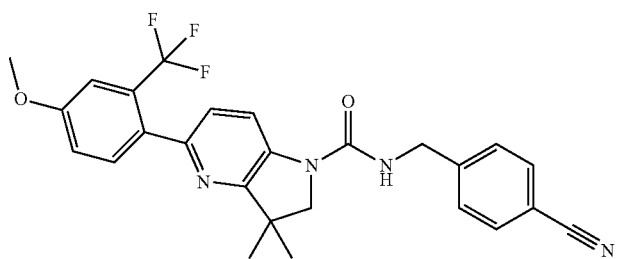 [SMILES: COc1ccc(-c2ccc3c(n2)C(C)(C)CN3C(=O)NCc2ccc(C#N)cc2)c(C(F)(F)F)c1] |
| 5 | 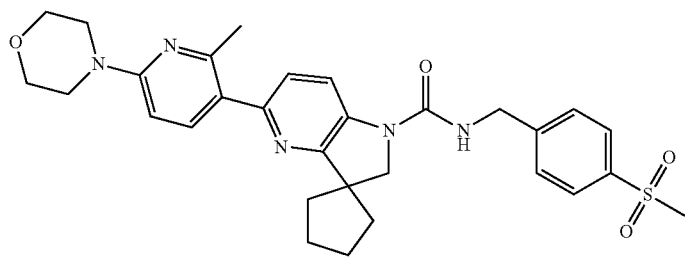 [SMILES: Cc1nc(N2CCOCC2)ccc1-c1ccc2c(n1)C1(CCCC1)CN2C(=O)NCc1ccc(S(C)(=O)=O)cc1] |
| 6 | 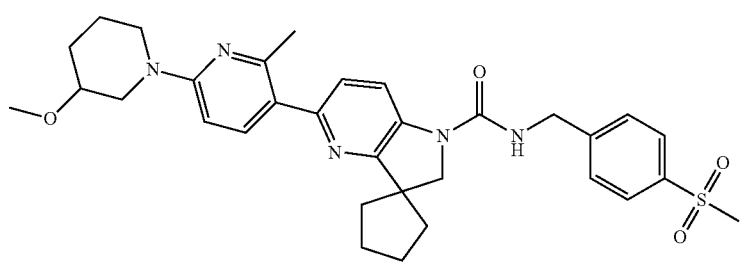 |

-continued
| Example | Structure |
|---|---|
| 7 | 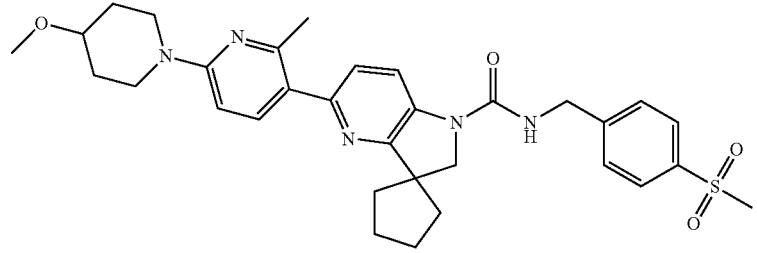 |
| 8 | 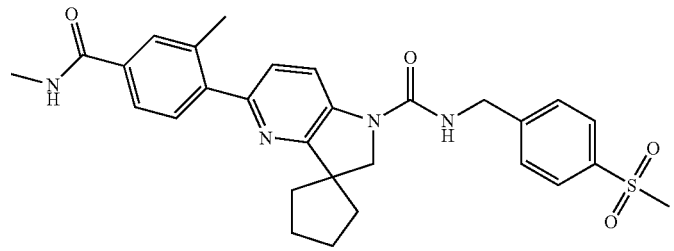 |
| 9 | 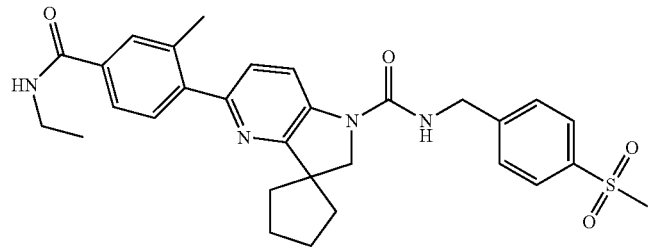 [SMILES: CCNC(=O)c1ccc(-c2ccc3c(n2)C2(CCCC2)CN3C(=O)NCc2ccc(S(C)(=O)=O)cc2)c(C)c1] |
| 10 | 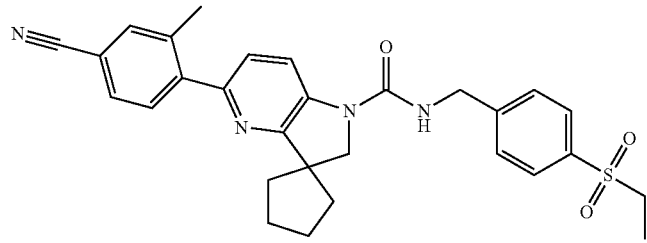 [SMILES: CCS(=O)(=O)c1ccc(CNC(=O)N2CC3(CCCC3)c3nc(-c4ccc(C#N)cc4C)ccc32)cc1] |
| 11 | 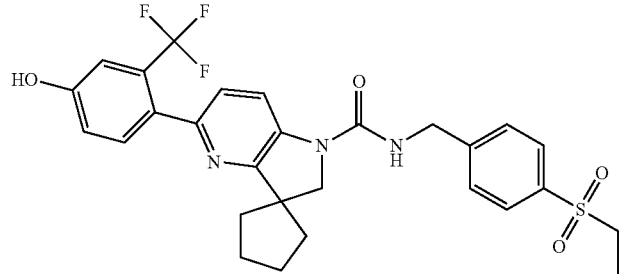 [SMILES: CCS(=O)(=O)c1ccc(CNC(=O)N2CC3(CCCC3)c3nc(-c4ccc(O)cc4C(F)(F)F)ccc32)cc1] |
| 12 | 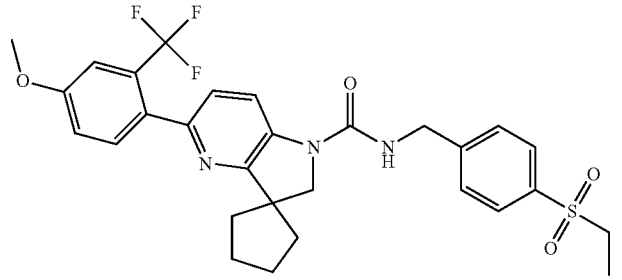 [SMILES: CCS(=O)(=O)c1ccc(CNC(=O)N2CC3(CCCC3)c3nc(-c4ccc(OC)cc4C(F)(F)F)ccc32)cc1] |

| Example | Structure |
|---------|-----------|
| 13 | 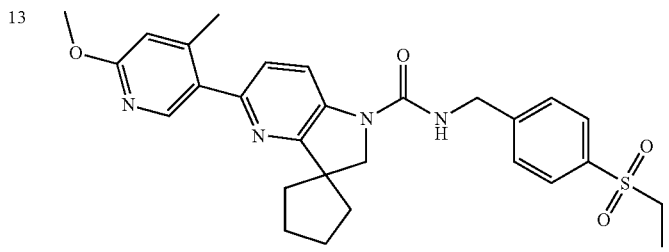 |
| 14 | 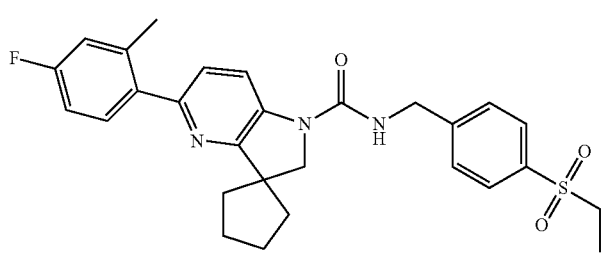 [SMILES: CCS(=O)(=O)c1ccc(CNC(=O)N2CC3(CCCC3)c3nc(-c4ccc(F)cc4C)ccc32)cc1] |
| 15 | 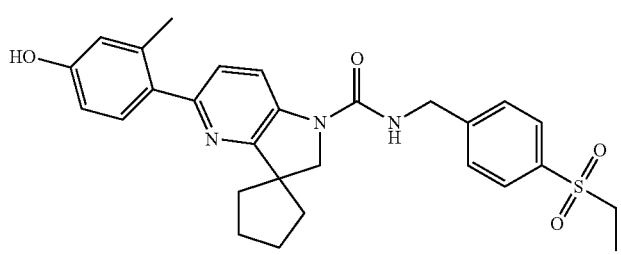 [SMILES: CCS(=O)(=O)c1ccc(CNC(=O)N2CC3(CCCC3)c3nc(-c4ccc(O)cc4C)ccc32)cc1] |
| 16 | 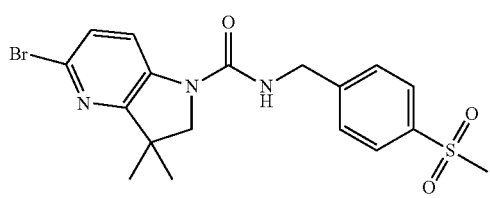 [SMILES: CC1(C)CN(C(=O)NCc2ccc(S(C)(=O)=O)cc2)c2ccc(Br)nc21] |
| 17 | 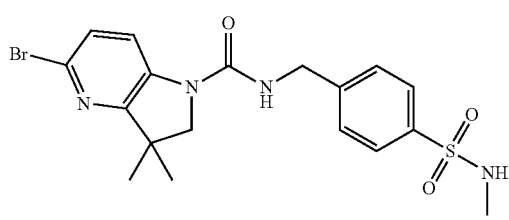 [SMILES: CNS(=O)(=O)c1ccc(CNC(=O)N2CC(C)(C)c3nc(Br)ccc32)cc1] |
| 18 | 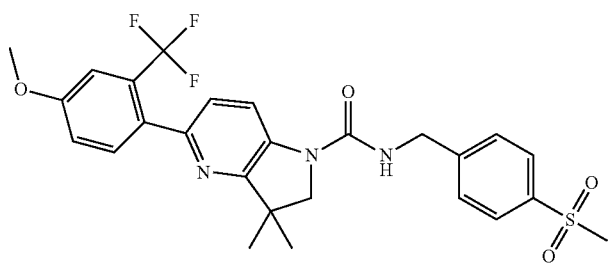 |

| Example | Structure |
|---|---|
| 19 | 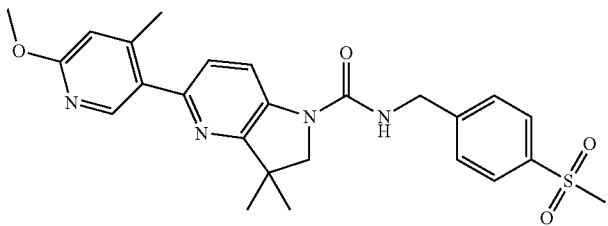 |
| 20 | 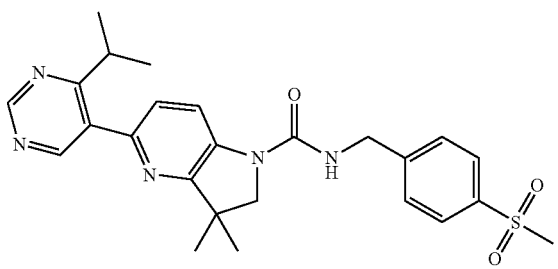 |
| 21 | 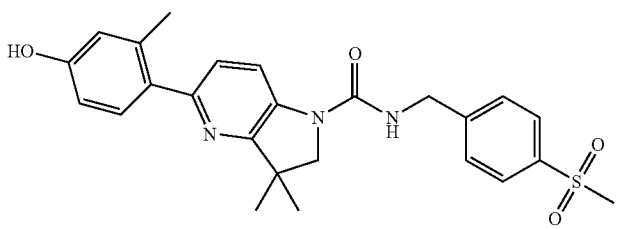 [SMILES: Cc1cc(O)ccc1-c1ccc2c(n1)C(C)(C)CN2C(=O)NCc1ccc(S(C)(=O)=O)cc1] |
| 22 | 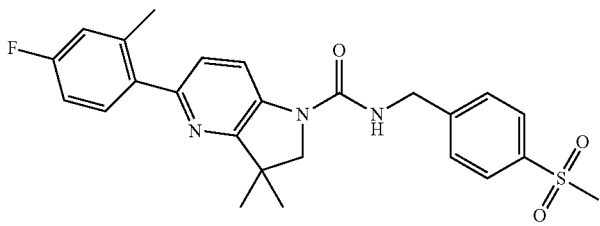 [SMILES: Cc1cc(F)ccc1-c1ccc2c(n1)C(C)(C)CN2C(=O)NCc1ccc(S(C)(=O)=O)cc1] |
| 23 | 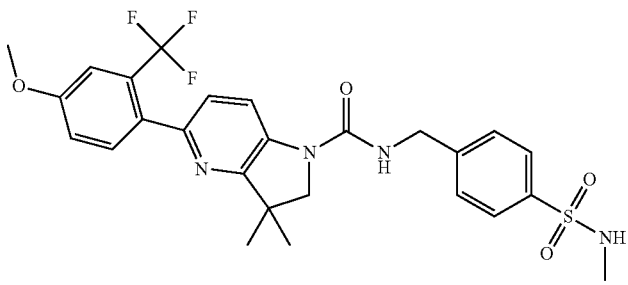 |
| 24 | 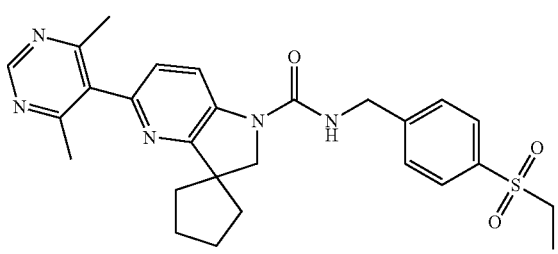 [SMILES: CCS(=O)(=O)c1ccc(CNC(=O)N2CC3(CCCC3)c3nc(-c4c(C)ncnc4C)ccc32)cc1] |

| Example | Structure |
|---|---|
| 25 | 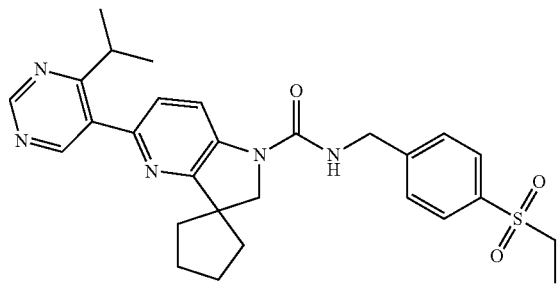 [SMILES: CCS(=O)(=O)c1ccc(CNC(=O)N2CC3(CCCC3)c3nc(-c4cncnc4C(C)C)ccc32)cc1] |
| 26 | 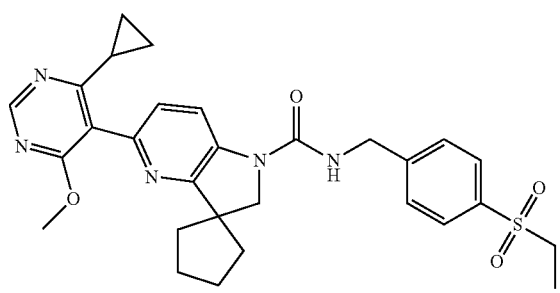 [SMILES: CCS(=O)(=O)c1ccc(CNC(=O)N2CC3(CCCC3)c3nc(-c4c(OC)ncnc4C4CC4)ccc32)cc1] |
| 27 | 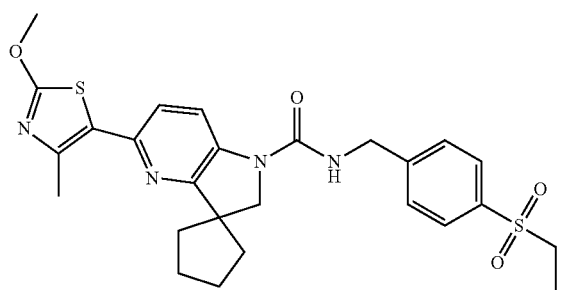 [SMILES: CCS(=O)(=O)c1ccc(CNC(=O)N2CC3(CCCC3)c3nc(-c4sc(OC)nc4C)ccc32)cc1] |
| 28 | 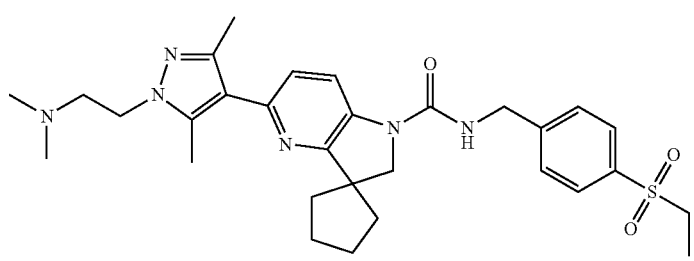 [SMILES: CCS(=O)(=O)c1ccc(CNC(=O)N2CC3(CCCC3)c3nc(-c4c(C)nn(CCN(C)C)c4C)ccc32)cc1] |
| 29 | 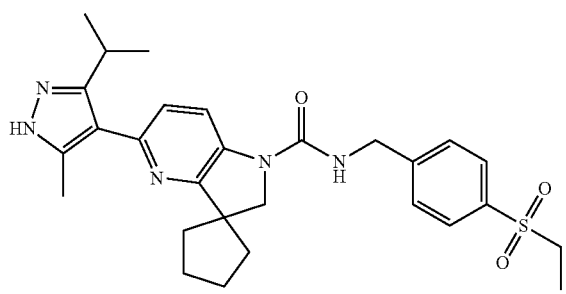 [SMILES: CCS(=O)(=O)c1ccc(CNC(=O)N2CC3(CCCC3)c3nc(-c4c(C(C)C)n[nH]c4C)ccc32)cc1] |

| Example | Structure |
|---|---|
| 30 | 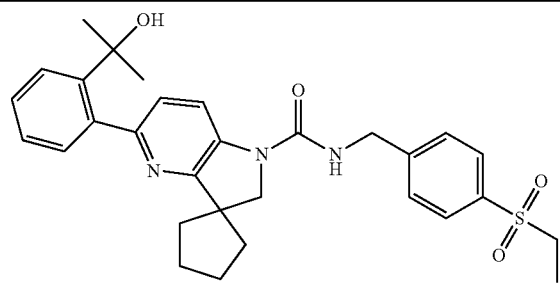 |
| 31 | 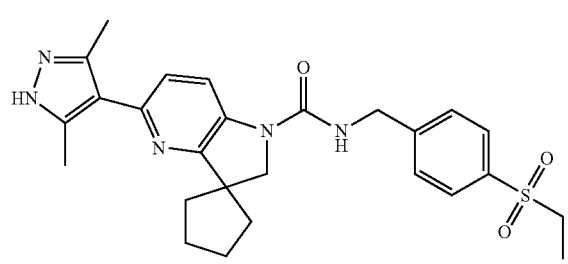 [SMILES: CCS(=O)(=O)c1ccc(CNC(=O)N2CC3(CCCC3)c3nc(-c4c(C)n[nH]c4C)ccc32)cc1] |
| 32 | 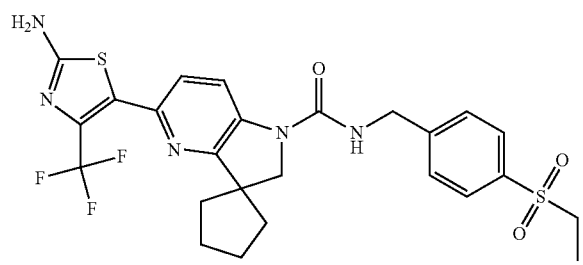 [SMILES: CCS(=O)(=O)c1ccc(CNC(=O)N2CC3(CCCC3)c3nc(-c4sc(N)nc4C(F)(F)F)ccc32)cc1] |
| 33 | 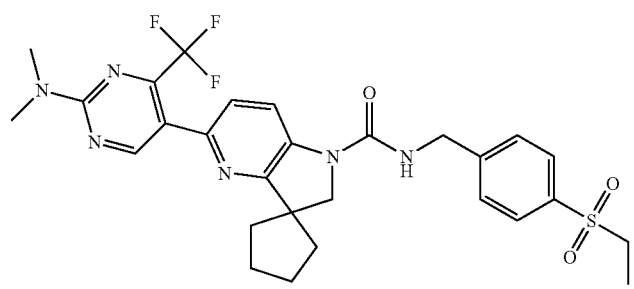 [SMILES: CCS(=O)(=O)c1ccc(CNC(=O)N2CC3(CCCC3)c3nc(-c4cnc(N(C)C)nc4C(F)(F)F)ccc32)cc1] |
| 34 | 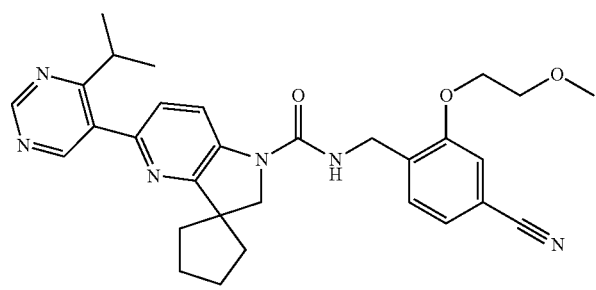 [SMILES: COCCOc1cc(C#N)ccc1CNC(=O)N1CC2(CCCC2)c2nc(-c3cncnc3C(C)C)ccc21] |

| Example | Structure |
|---|---|
| 35 | 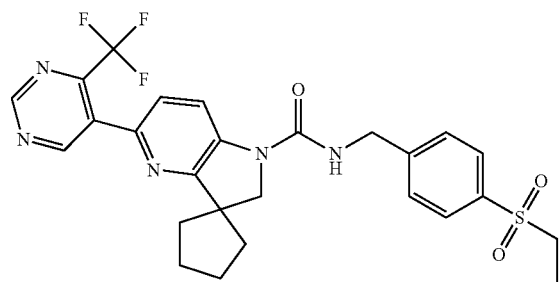 [SMILES: CCS(=O)(=O)c1ccc(CNC(=O)N2CC3(CCCC3)c3nc(-c4cncnc4C(F)(F)F)ccc32)cc1] |
| 36 | 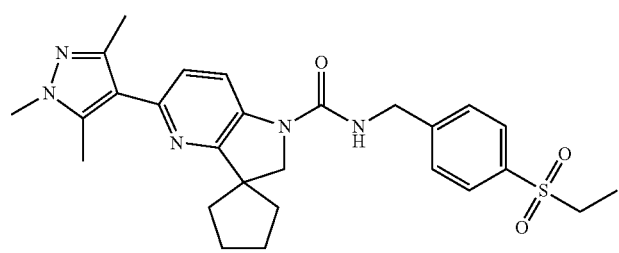 [SMILES: CCS(=O)(=O)c1ccc(CNC(=O)N2CC3(CCCC3)c3nc(-c4c(C)nn(C)c4C)ccc32)cc1] |
| 37 | 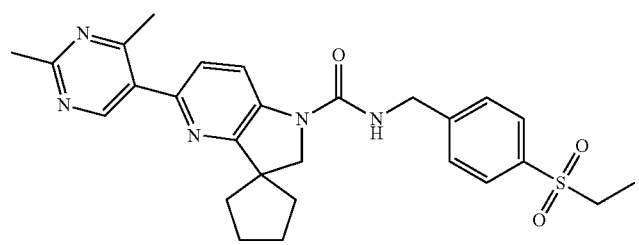 |
| 38 | 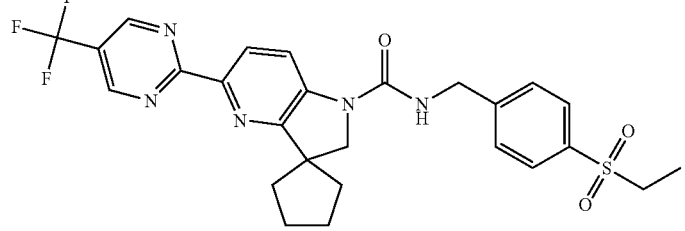 |
| 39 | 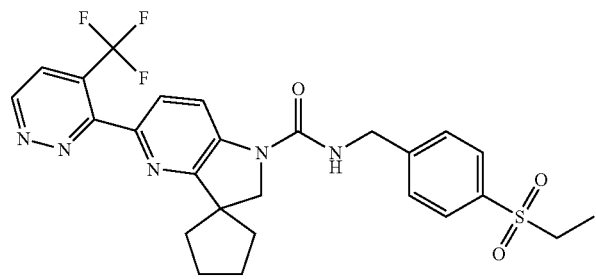 [SMILES: CCS(=O)(=O)c1ccc(CNC(=O)N2CC3(CCCC3)c3nc(-c4nnccc4C(F)(F)F)ccc32)cc1] |
| 40 | 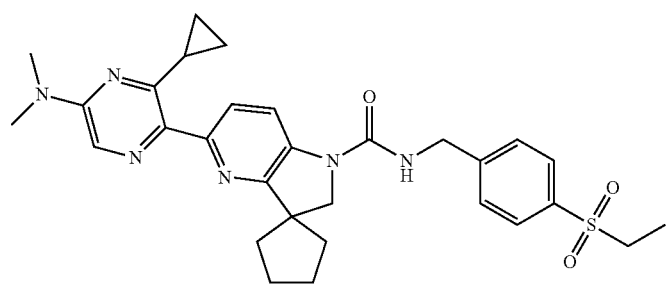 [SMILES: CCS(=O)(=O)c1ccc(CNC(=O)N2CC3(CCCC3)c3nc(-c4ncc(N(C)C)nc4C4CC4)ccc32)cc1] |

-continued
| Example | Structure |
|---|---|
| 41 | 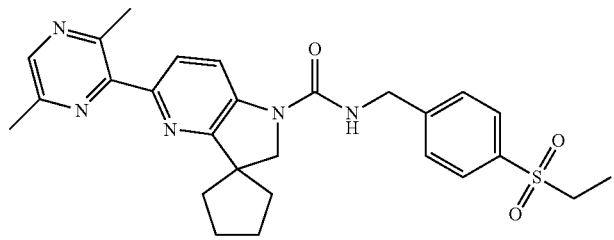 [SMILES: CCS(=O)(=O)c1ccc(CNC(=O)N2CC3(CCCC3)c3nc(-c4nc(C)cnc4C)ccc32)cc1] |
| 42 | 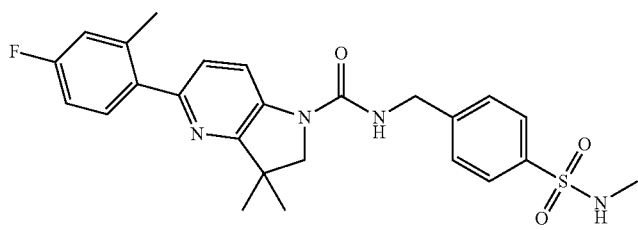 [SMILES: CNS(=O)(=O)c1ccc(CNC(=O)N2CC(C)(C)c3nc(-c4ccc(F)cc4C)ccc32)cc1] |
| 43 | 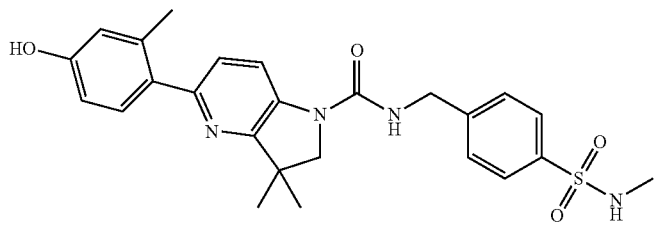 [SMILES: CNS(=O)(=O)c1ccc(CNC(=O)N2CC(C)(C)c3nc(-c4ccc(O)cc4C)ccc32)cc1] |
| 44 | 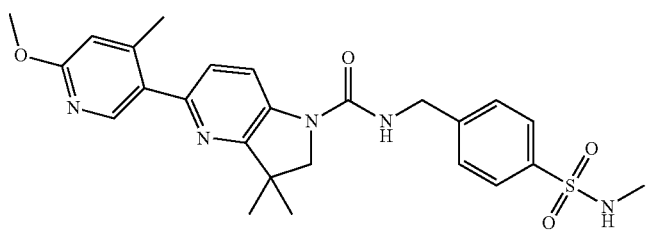 |
| 45 | 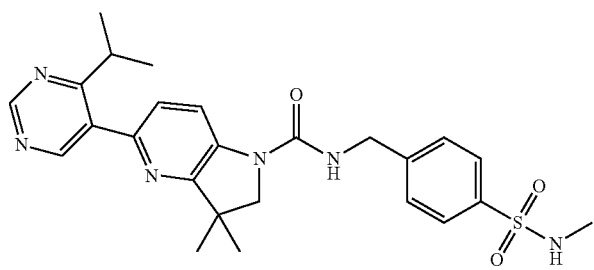 [SMILES: CNS(=O)(=O)c1ccc(CNC(=O)N2CC(C)(C)c3nc(-c4cncnc4C(C)C)ccc32)cc1] |
| 46 | 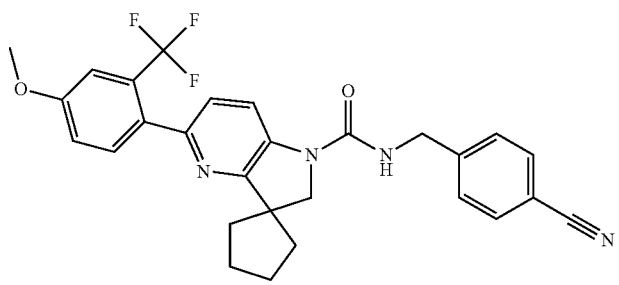 [SMILES: COc1ccc(-c2ccc3c(n2)C2(CCCC2)CN3C(=O)NCc2ccc(C#N)cc2)c(C(F)(F)F)c1] |

-continued
| Example | Structure |
|---|---|
| 47 | 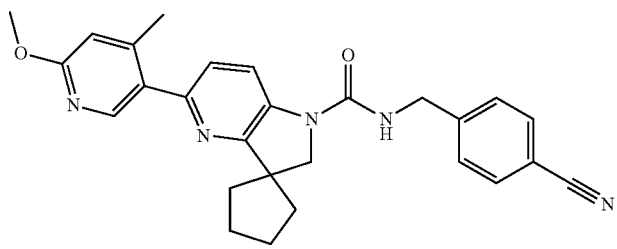 [SMILES: COc1cc(C)c(-c2ccc3c(n2)C2(CCCC2)CN3C(=O)NCc2ccc(C#N)cc2)cn1] |
| 48 | 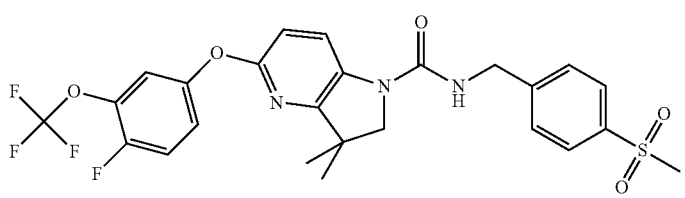 [SMILES: CC1(C)CN(C(=O)NCc2ccc(S(C)(=O)=O)cc2)c2ccc(Oc3ccc(F)c(OC(F)(F)F)c3)nc21] |
| 49 | 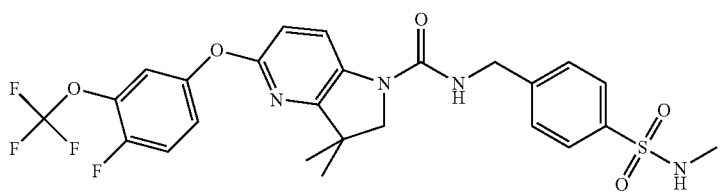 [SMILES: CNS(=O)(=O)c1ccc(CNC(=O)N2CC(C)(C)c3nc(Oc4ccc(F)c(OC(F)(F)F)c4)ccc32)cc1] |
| 50 | 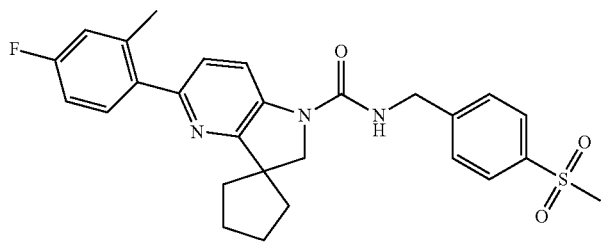 [SMILES: Cc1cc(F)ccc1-c1ccc2c(n1)C1(CCCC1)CN2C(=O)NCc1ccc(S(C)(=O)=O)cc1] |
| 51 | 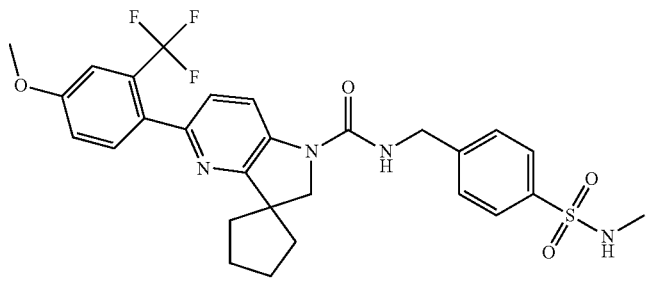 |
| 52 | 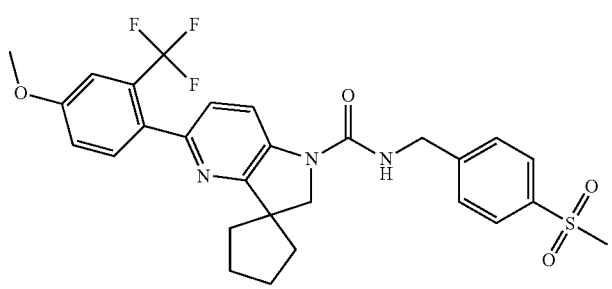 |

-continued
| Example | Structure |
|---|---|
| 53 | 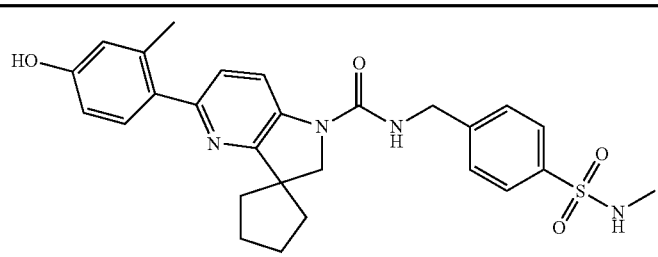 |
| 54 | 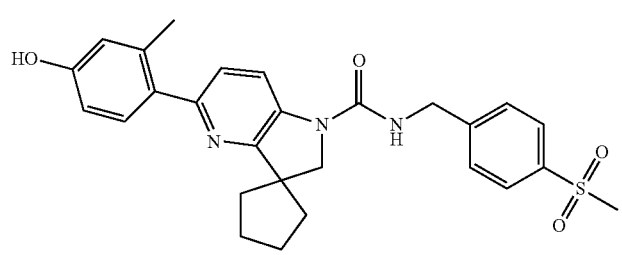 [SMILES: Cc1cc(O)ccc1-c1ccc2c(n1)C1(CCCC1)CN2C(=O)NCc1ccc(S(C)(=O)=O)cc1] |
| 55 | 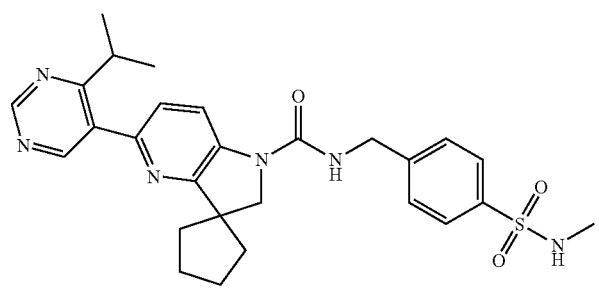 [SMILES: CNS(=O)(=O)c1ccc(CNC(=O)N2CC3(CCCC3)c3nc(-c4cncnc4C(C)C)ccc32)cc1] |
| 56 | 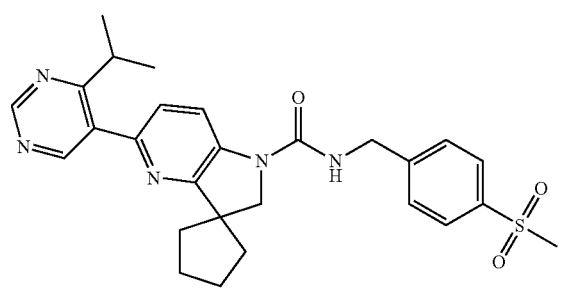 [SMILES: CC(C)c1ncncc1-c1ccc2c(n1)C1(CCCC1)CN2C(=O)NCc1ccc(S(C)(=O)=O)cc1] |
| 57 | 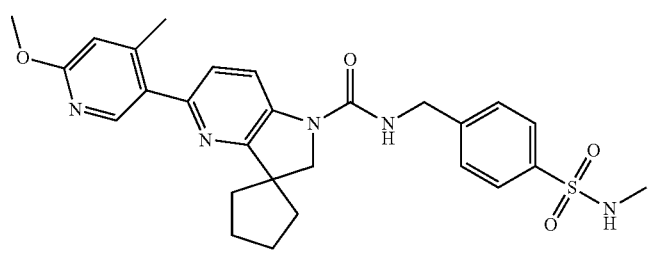 |
| 58 | 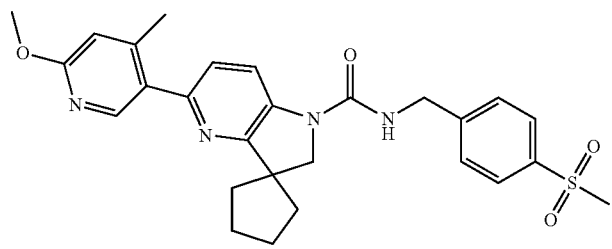 |

-continued
| Example | Structure |
|---|---|
| 59 | 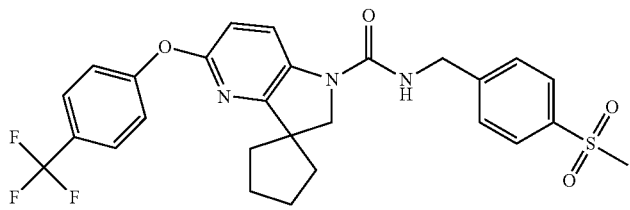 |
| 60 | 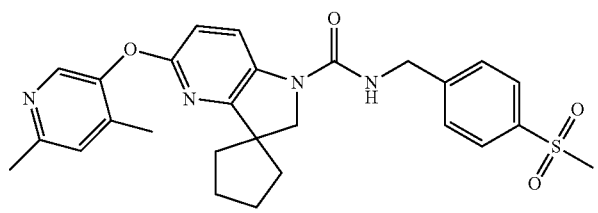 |
| 61 | 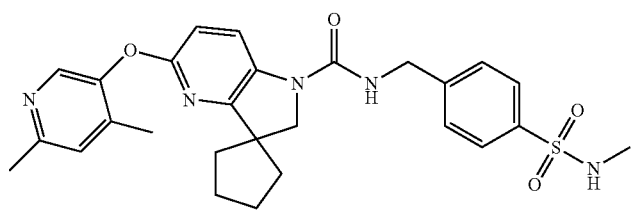 |
| 62 | 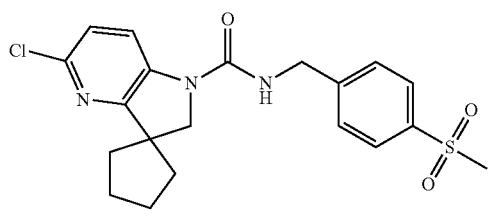 [SMILES: CS(=O)(=O)c1ccc(CNC(=O)N2CC3(CCCC3)c3nc(Cl)ccc32)cc1] |
| 63 | 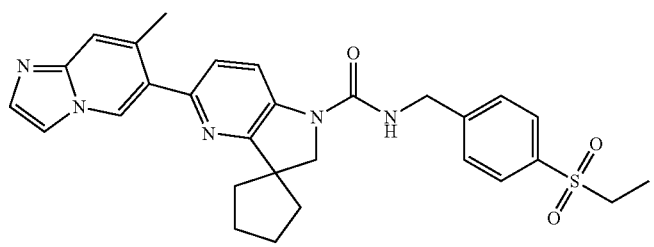 [SMILES: CCS(=O)(=O)c1ccc(CNC(=O)N2CC3(CCCC3)c3nc(-c4cn5ccnc5cc4C)ccc32)cc1] |
| 64 | 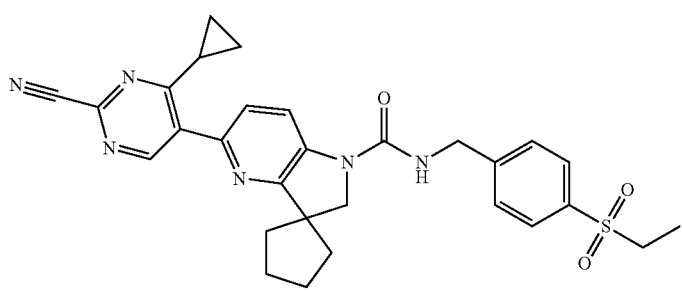 [SMILES: CCS(=O)(=O)c1ccc(CNC(=O)N2CC3(CCCC3)c3nc(-c4cnc(C#N)nc4C4CC4)ccc32)cc1] |

| Example | Structure |
|---|---|
| 65 | 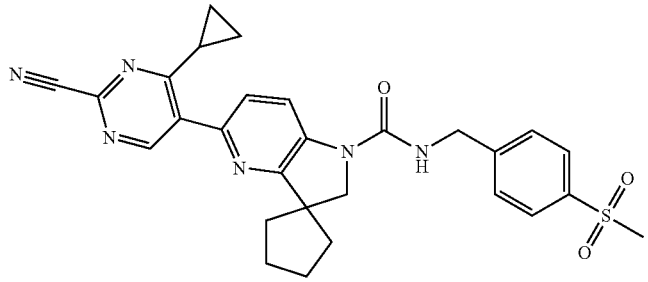 [SMILES: CS(=O)(=O)c1ccc(CNC(=O)N2CC3(CCCC3)c3nc(-c4cnc(C#N)nc4C4CC4)ccc32)cc1] |
| 66 | 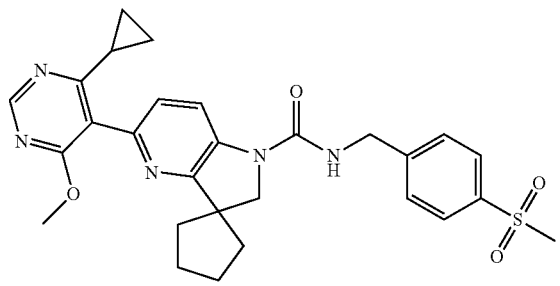 |
| 67 | 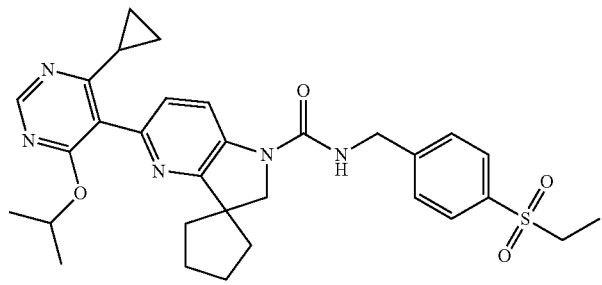 [SMILES: CCS(=O)(=O)c1ccc(CNC(=O)N2CC3(CCCC3)c3nc(-c4c(OC(C)C)ncnc4C4CC4)ccc32)cc1] |
| 68 | 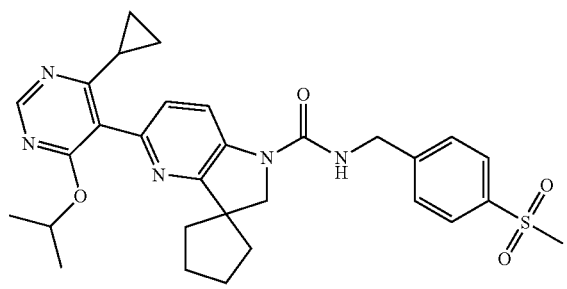 [SMILES: CC(C)Oc1ncnc(C2CC2)c1-c1ccc2c(n1)C1(CCCC1)CN2C(=O)NCc1ccc(S(C)(=O)=O)cc1] |
| 69 | 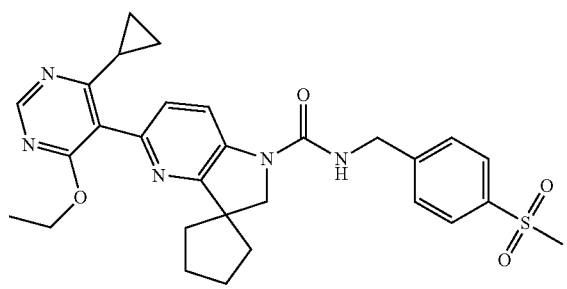 [SMILES: CCOc1ncnc(C2CC2)c1-c1ccc2c(n1)C1(CCCC1)CN2C(=O)NCc1ccc(S(C)(=O)=O)cc1] |

| Example | Structure |
|---|---|
| 70 | 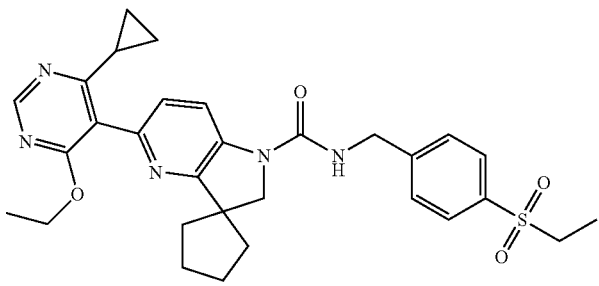 [SMILES: CCOc1ncnc(C2CC2)c1-c1ccc2c(n1)C1(CCCC1)CN2C(=O)NCc1ccc(S(=O)(=O)CC)cc1] |
| 71 | 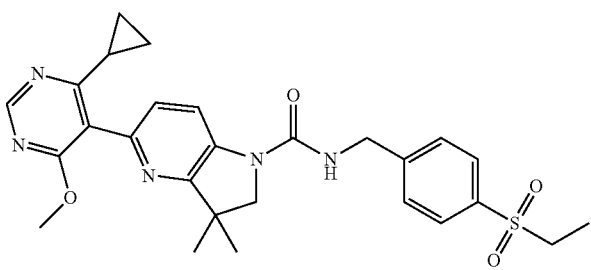 [SMILES: CCS(=O)(=O)c1ccc(CNC(=O)N2CC(C)(C)c3nc(-c4c(OC)ncnc4C4CC4)ccc32)cc1] |
| 72 | 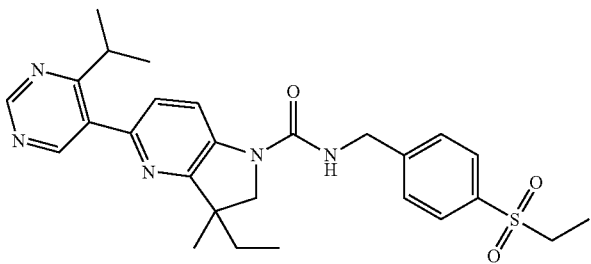 [SMILES: CCC1(C)CN(C(=O)NCc2ccc(S(=O)(=O)CC)cc2)c2ccc(-c3cncnc3C(C)C)nc21] |
| 73 | 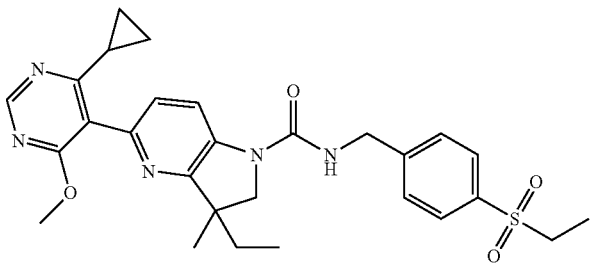 [SMILES: CCC1(C)CN(C(=O)NCc2ccc(S(=O)(=O)CC)cc2)c2ccc(-c3c(OC)ncnc3C3CC3)nc21] |
| 74 | 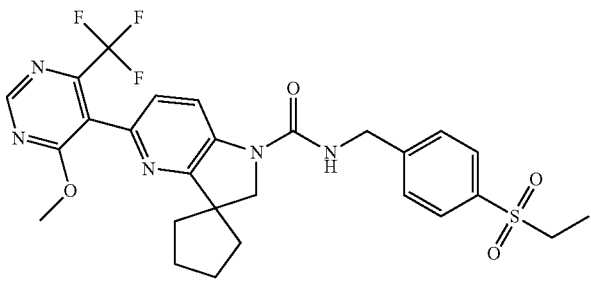 [SMILES: CCS(=O)(=O)c1ccc(CNC(=O)N2CC3(CCCC3)c3nc(-c4c(OC)ncnc4C(F)(F)F)ccc32)cc1] |

| Example | Structure |
|---|---|
| 75 | 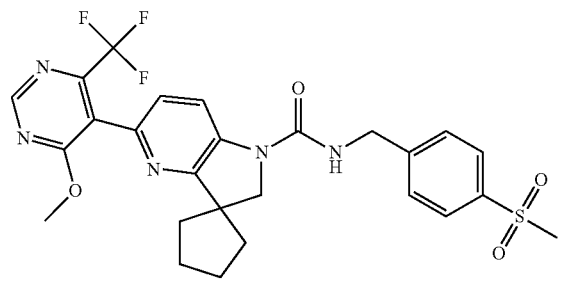 [SMILES: COc1ncnc(C(F)(F)F)c1-c1ccc2c(n1)C1(CCCC1)CN2C(=O)NCc1ccc(S(C)(=O)=O)cc1] |
| 76 | 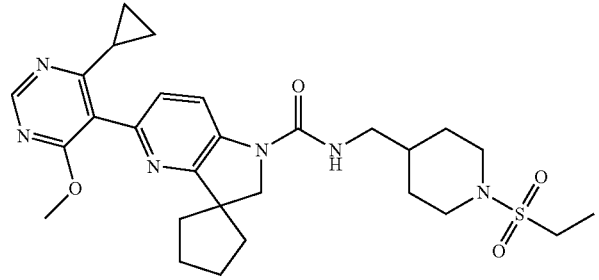 [SMILES: CCS(=O)(=O)N1CCC(CNC(=O)N2CC3(CCCC3)c3nc(-c4c(OC)ncnc4C4CC4)ccc32)CC1] |
| 77 | 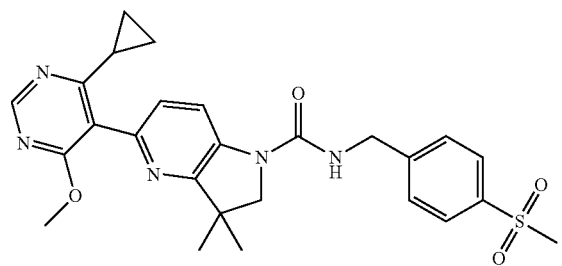 [SMILES: COc1ncnc(C2CC2)c1-c1ccc2c(n1)C(C)(C)CN2C(=O)NCc1ccc(S(C)(=O)=O)cc1] |
| 78 | 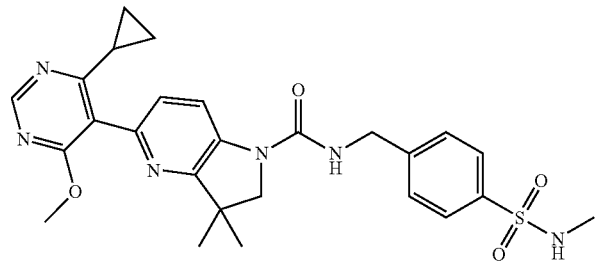 [SMILES: CNS(=O)(=O)c1ccc(CNC(=O)N2CC(C)(C)c3nc(-c4c(OC)ncnc4C4CC4)ccc32)cc1] |
| 79 | 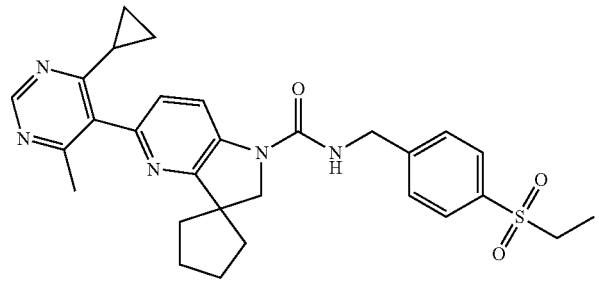 [SMILES: CCS(=O)(=O)c1ccc(CNC(=O)N2CC3(CCCC3)c3nc(-c4c(C)ncnc4C4CC4)ccc32)cc1] |

| Example | Structure |
|---|---|
| 80 | 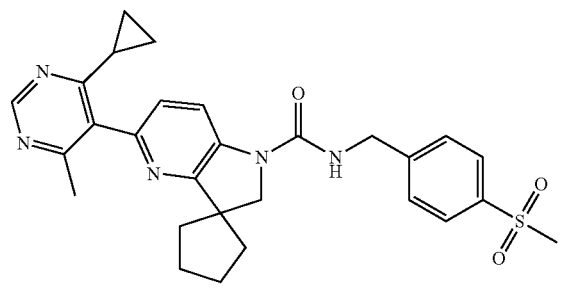 [SMILES: Cc1ncnc(C2CC2)c1-c1ccc2c(n1)C1(CCCC1)CN2C(=O)NCc1ccc(S(C)(=O)=O)cc1] |
| 81 | 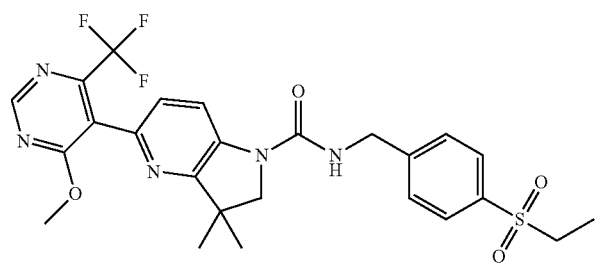 [SMILES: CCS(=O)(=O)c1ccc(CNC(=O)N2CC(C)(C)c3nc(-c4c(OC)ncnc4C(F)(F)F)ccc32)cc1] |
| 82 | 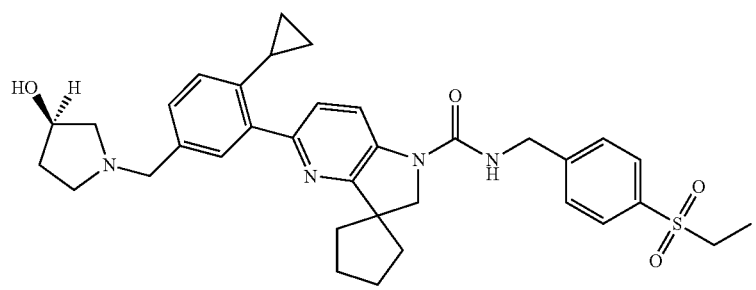 [SMILES: CCS(=O)(=O)c1ccc(CNC(=O)N2CC3(CCCC3)c3nc(-c4cc(CN5CC[C@@H](O)C5)ccc4C4CC4)ccc32)cc1] |
| 83 | 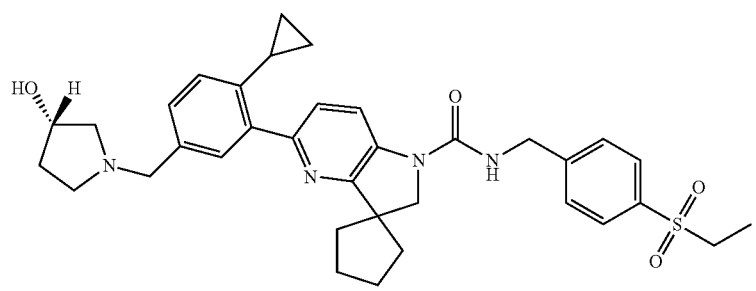 [SMILES: CCS(=O)(=O)c1ccc(CNC(=O)N2CC3(CCCC3)c3nc(-c4cc(CN5CC[C@H](O)C5)ccc4C4CC4)ccc32)cc1] |
| 84 | 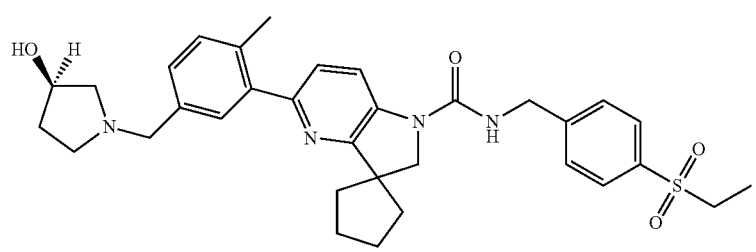 [SMILES: CCS(=O)(=O)c1ccc(CNC(=O)N2CC3(CCCC3)c3nc(-c4cc(CN5CC[C@@H](O)C5)ccc4C)ccc32)cc1] |

| Example | Structure |
|---|---|
| 85 | 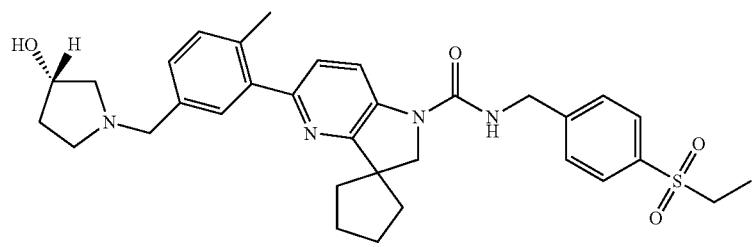 [SMILES: CCS(=O)(=O)c1ccc(CNC(=O)N2CC3(CCCC3)c3nc(-c4cc(CN5CC[C@H](O)C5)ccc4C)ccc32)cc1] |
| 86 | 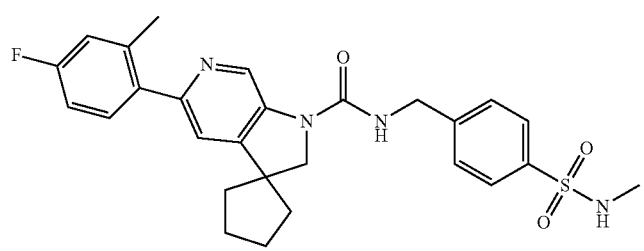 [SMILES: CNS(=O)(=O)c1ccc(CNC(=O)N2CC3(CCCC3)c3cc(-c4ccc(F)cc4C)ncc32)cc1] |
| 87 | 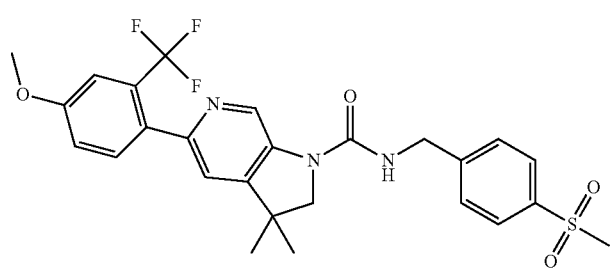 |
| 88 | 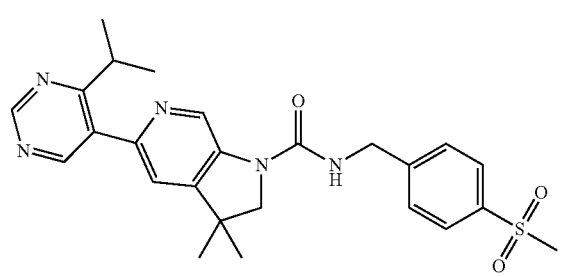 [SMILES: CC(C)c1ncncc1-c1cc2c(cn1)N(C(=O)NCc1ccc(S(C)(=O)=O)cc1)CC2(C)C] |
| 89 | 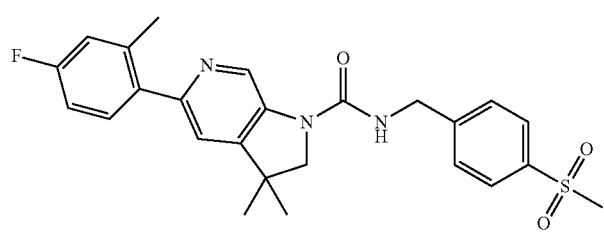 |
| 90 | 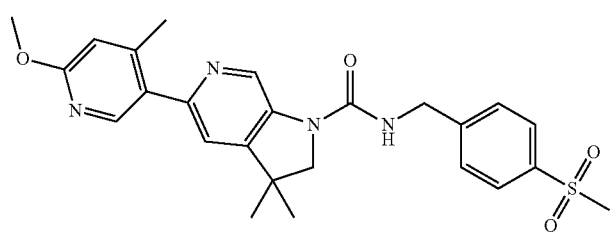 |

-continued
| Example | Structure |
|---------|-----------|
| 91 | 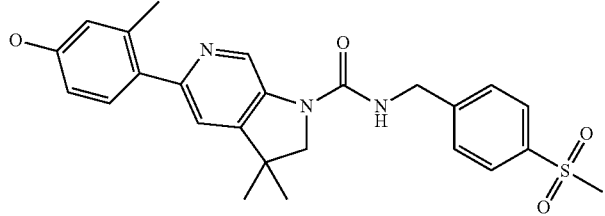 [SMILES: Cc1cc(F)ccc1-c1cc2c(cn1)N(C(=O)NCc1ccc(S(C)(=O)=O)cc1)CC2(C)C] |
| 92 | 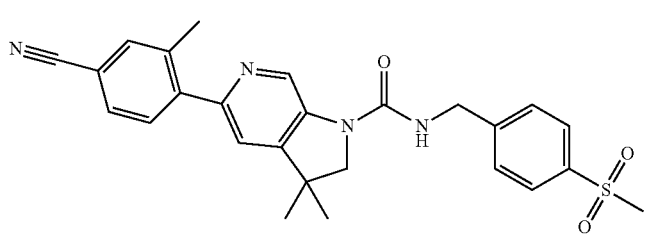 [SMILES: Cc1cc(C#N)ccc1-c1cc2c(cn1)N(C(=O)NCc1ccc(S(C)(=O)=O)cc1)CC2(C)C] |
| 93 | 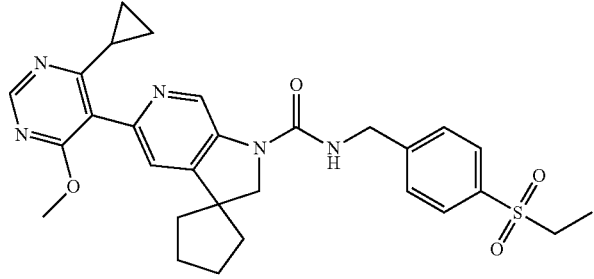 [SMILES: CCS(=O)(=O)c1ccc(CNC(=O)N2CC3(CCCC3)c3cc(-c4c(OC)ncnc4C4CC4)ncc32)cc1] |
| 94 | 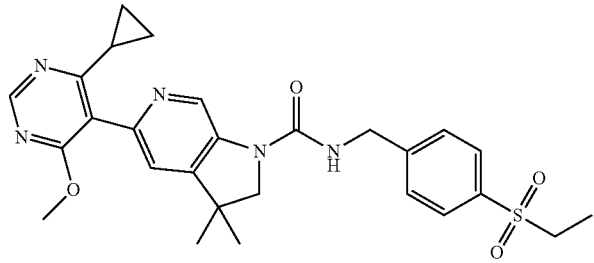 [SMILES: CCS(=O)(=O)c1ccc(CNC(=O)N2CC(C)(C)c3cc(-c4c(OC)ncnc4C4CC4)ncc32)cc1] |
| 95 | 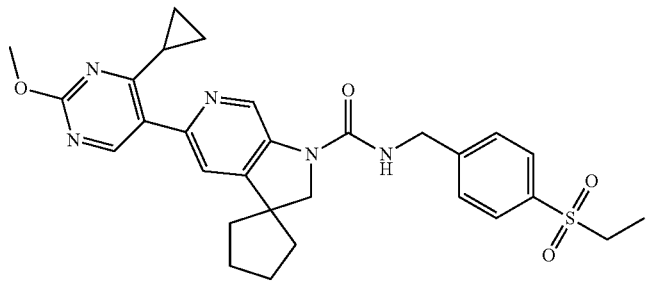 [SMILES: CCS(=O)(=O)c1ccc(CNC(=O)N2CC3(CCCC3)c3cc(-c4cnc(OC)nc4C4CC4)ncc32)cc1] |
| 96 | 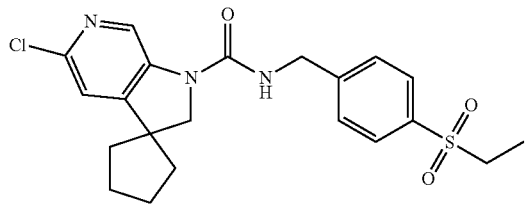 [SMILES: CCS(=O)(=O)c1ccc(CNC(=O)N2CC3(CCCC3)c3cc(Cl)ncc32)cc1] |

| Example | Structure |
|---------|-----------|
| 97 | 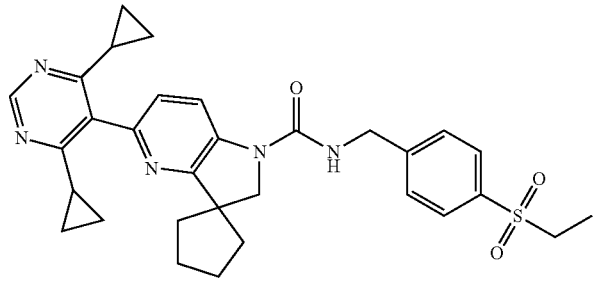 [SMILES: CCS(=O)(=O)c1ccc(CNC(=O)N2CC3(CCCC3)c3nc(-c4c(C5CC5)ncnc4C4CC4)ccc32)cc1] |
| 98 | 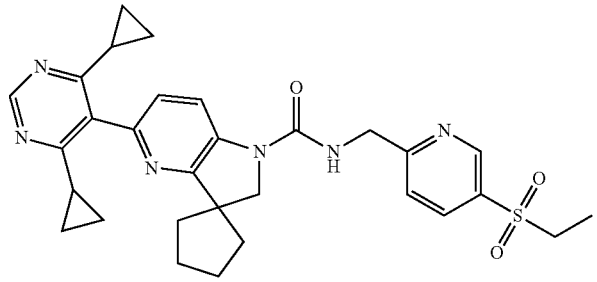 [SMILES: CCS(=O)(=O)c1ccc(CNC(=O)N2CC3(CCCC3)c3nc(-c4c(C5CC5)ncnc4C4CC4)ccc32)nc1] |
| 99 | 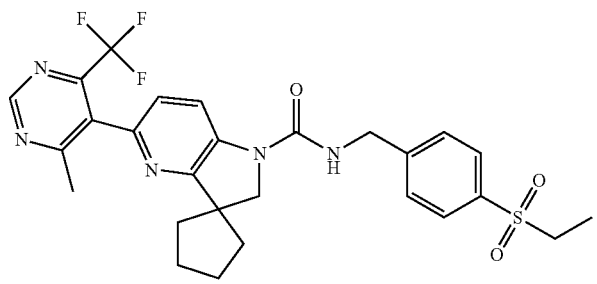 [SMILES: CCS(=O)(=O)c1ccc(CNC(=O)N2CC3(CCCC3)c3nc(-c4c(C)ncnc4C(F)(F)F)ccc32)cc1] |
| 100 | 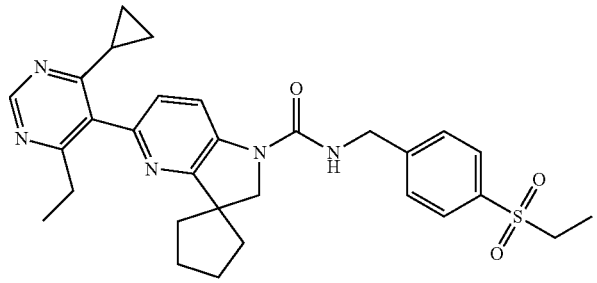 |
| 101 | 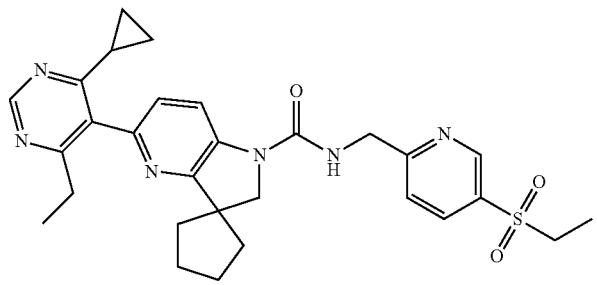 [SMILES: CCc1ncnc(C2CC2)c1-c1ccc2c(n1)C1(CCCC1)CN2C(=O)NCc1ccc(S(=O)(=O)CC)cn1] |

| Example | Structure |
|---|---|
| 102 | 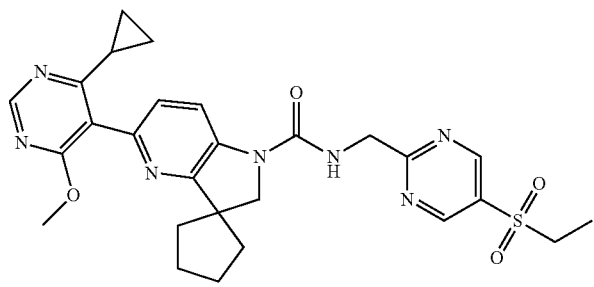 [SMILES: CCS(=O)(=O)c1cnc(CNC(=O)N2CC3(CCCC3)c3nc(-c4c(OC)ncnc4C4CC4)ccc32)nc1] |
or a pharmaceutically acceptable salt thereof.
13. A pharmaceutical composition comprising a compound of formula (I) according to claim 1, or a pharmaceutically acceptable salt thereof, and at least one pharmaceutically acceptable carrier.
* * * * *